(12) United States Patent
Miller et al.

(10) Patent No.: US 11,324,398 B2
(45) Date of Patent: May 10, 2022

(54) OPHTHALMOSCOPY METHOD

(71) Applicant: Indiana University Research and Technology Corporation, Indianapolis, IN (US)

(72) Inventors: Donald Thomas Miller, Bloomington, IN (US); Zhuolin Liu, North Potomac, MD (US); Kazuhiro Suzuki, Bloomington, IN (US); Furu Zhang, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 316 days.

(21) Appl. No.: 16/522,183

(22) Filed: Jul. 25, 2019

(65) Prior Publication Data
US 2020/0022575 A1    Jan. 23, 2020

Related U.S. Application Data

(63) Continuation-in-part of application No. PCT/US2018/015256, filed on Jan. 25, 2018.
(Continued)

(51) Int. Cl.
*A61B 3/00*     (2006.01)
*A61B 3/10*     (2006.01)
(Continued)

(52) U.S. Cl.
CPC .......... *A61B 3/0025* (2013.01); *A61B 3/102* (2013.01); *A61B 3/1225* (2013.01); *A61B 3/13* (2013.01); *A61B 3/14* (2013.01)

(58) Field of Classification Search
CPC ..... A61B 3/0025; A61B 3/102; A61B 3/1225; A61B 3/13; A61B 3/14; G06K 9/0014;
(Continued)

(56) References Cited

U.S. PATENT DOCUMENTS 9,662,407 B2 *   5/2017   Boyd ................... A61B 3/1241
2010/0238401 A1 *   9/2010   Kunath-Fandrei ....... A61B 3/14
351/206

(Continued)

FOREIGN PATENT DOCUMENTS

WO    2013/165614 A1    11/2013

OTHER PUBLICATIONS

International Preliminary Report on Patentability received for PCT Patent Application No. PCT/US2018/015256, dated Aug. 8, 2019, 6 pages.
(Continued)

*Primary Examiner* — Mohammed A Hasan
(74) *Attorney, Agent, or Firm* — Faegre Drinker Biddle & Reath LLP

(57) ABSTRACT

A method is provided for observing structure and function of individual cells in a living human eye, comprising: using an adaptive optics optical coherence tomography (AO-OCT) system to image a volume of a retinal patch including numerous cells of different types, as for example, ganglion cells; using 3D subcellular image registration to correct for eye motion, including digitally dissecting the imaged volume; and using organelle motility inside the cell to increase cell contrast and to measure cell temporal dynamics.

28 Claims, 71 Drawing Sheets

Related U.S. Application Data

(60) Provisional application No. 62/450,161, filed on Jan. 25, 2017.

(51) Int. Cl.
*A61B 3/12* (2006.01)
*A61B 3/13* (2006.01)
*A61B 3/14* (2006.01)

(58) Field of Classification Search
CPC ............ G06K 9/00147; G01B 9/02034; G01B 9/02091; G01B 9/02041
USPC ........................................................ 351/206
See application file for complete search history.

(56) References Cited

U.S. PATENT DOCUMENTS

2013/0058553 A1   3/2013   Yonezawa et al.
2013/0208245 A1*  8/2013   Campbell .............. A61B 3/102
                                                                351/246

OTHER PUBLICATIONS

International Search Report and Written Opinion received for PCT Patent Application No. PCT/US2018/015256, dated Apr. 16, 2018, 6 pages.

Kurokawa et al., Three-dimensional retinal and choroidal capillary imaging by power Doppler optical coherence angiography with adaptive optics. Optical Society of America vol. 20, No. 20, Sep. 20, 2012.

Liu et al., 3D Imaging of Retinal Pigment Epithelial Colic in the Living human Retinal. Investigative Ophthalmology & Visual Science vol. 57 No. 9, Aug. 31, 2016.

* cited by examiner

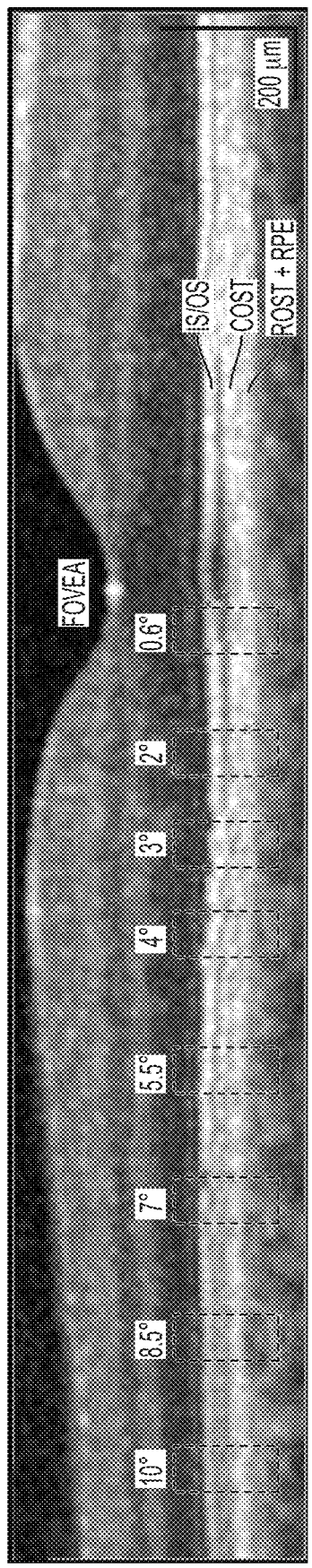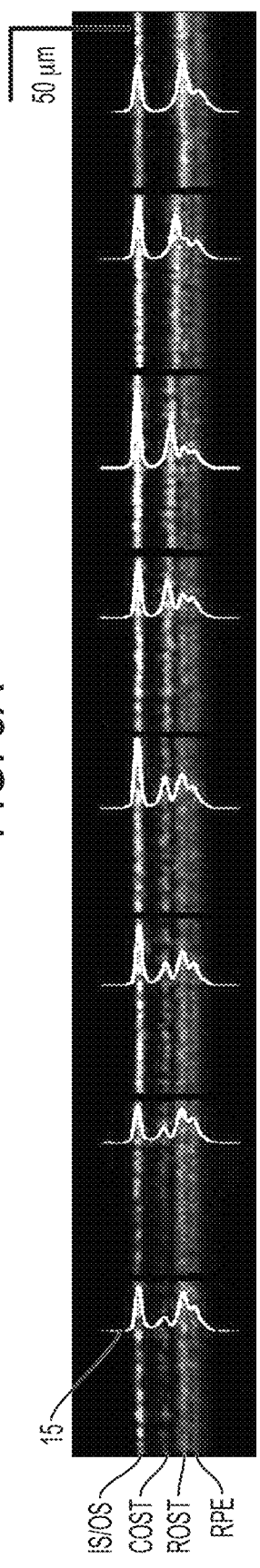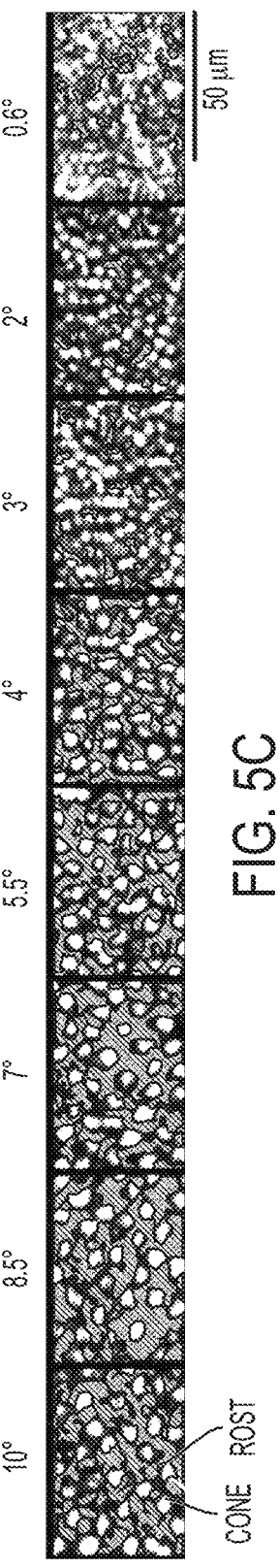
FIG. 5A
FIG. 5B
FIG. 5C

TI=12.9 s (N=39)

TI=0.2 s (N=39)

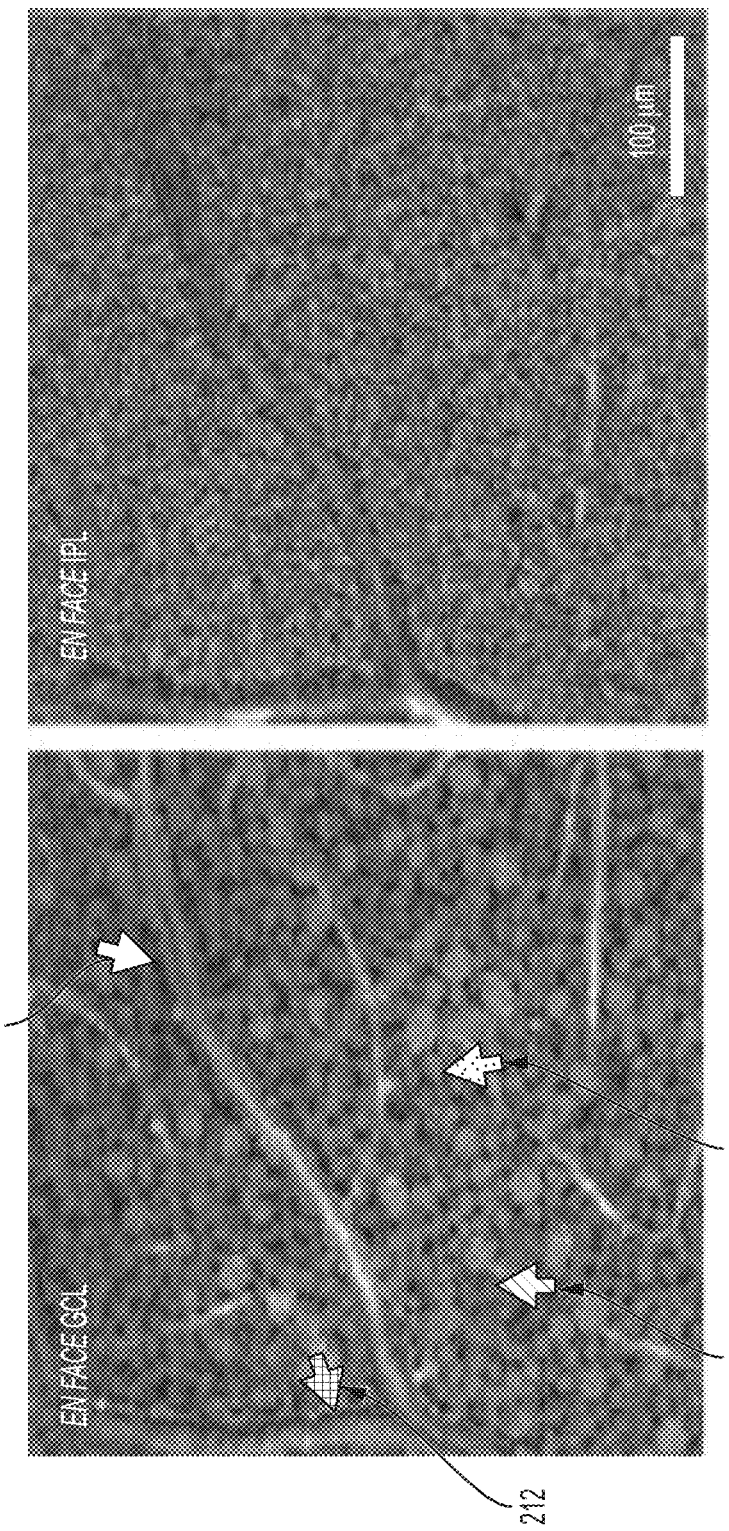

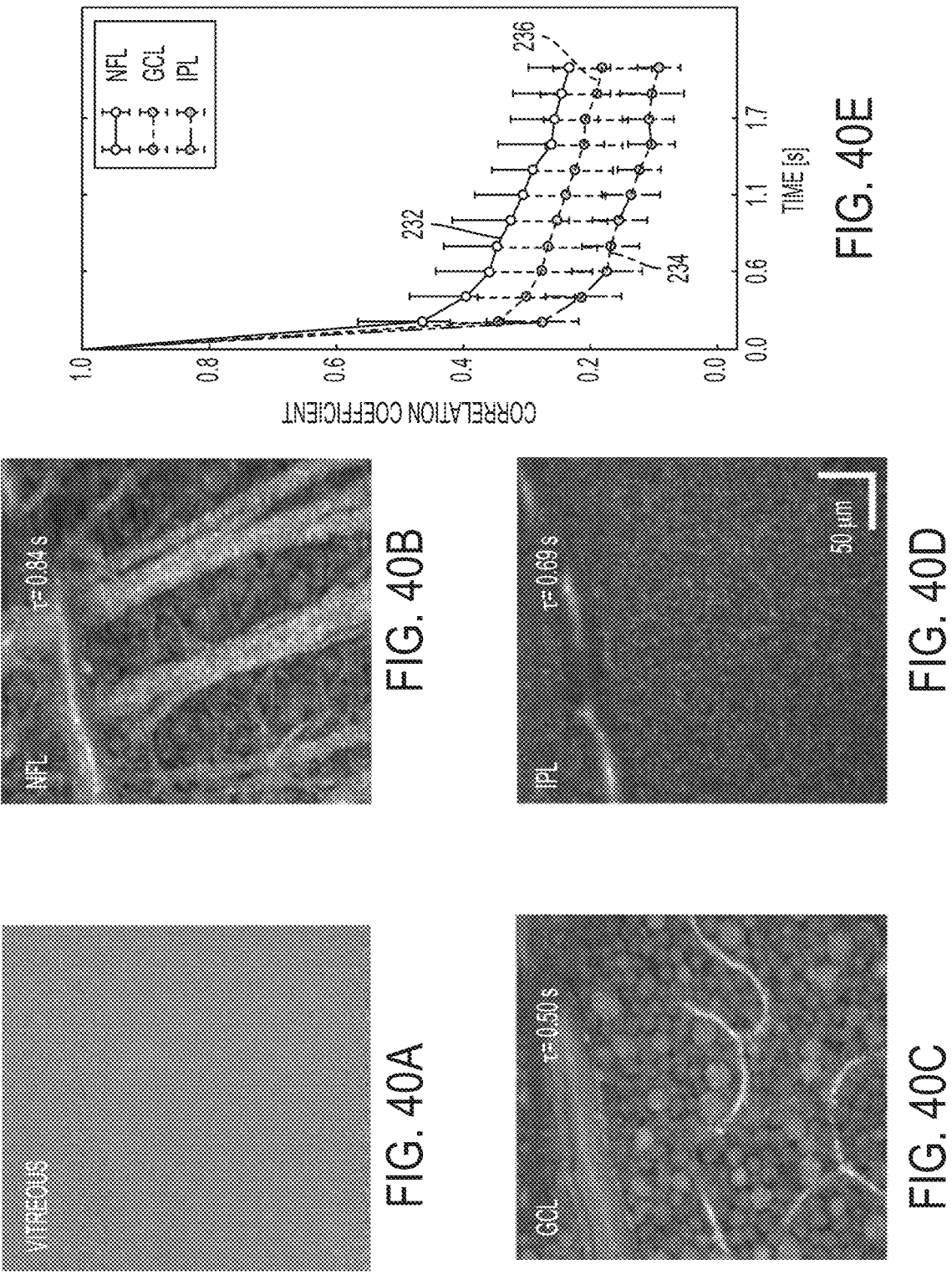

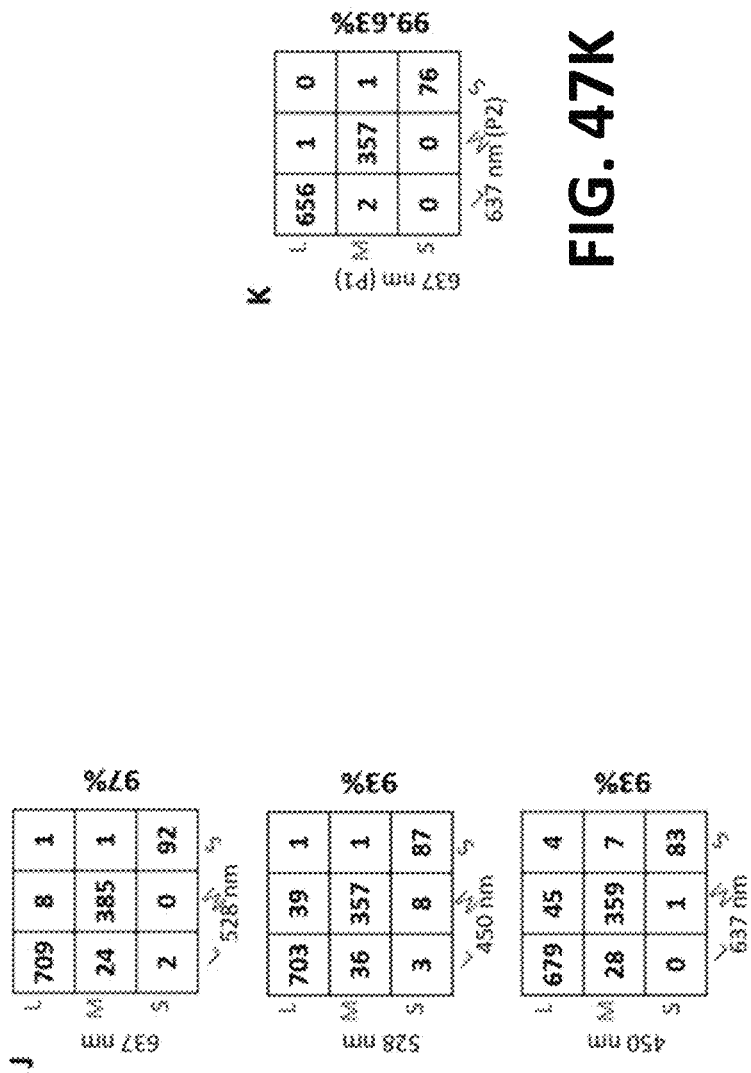

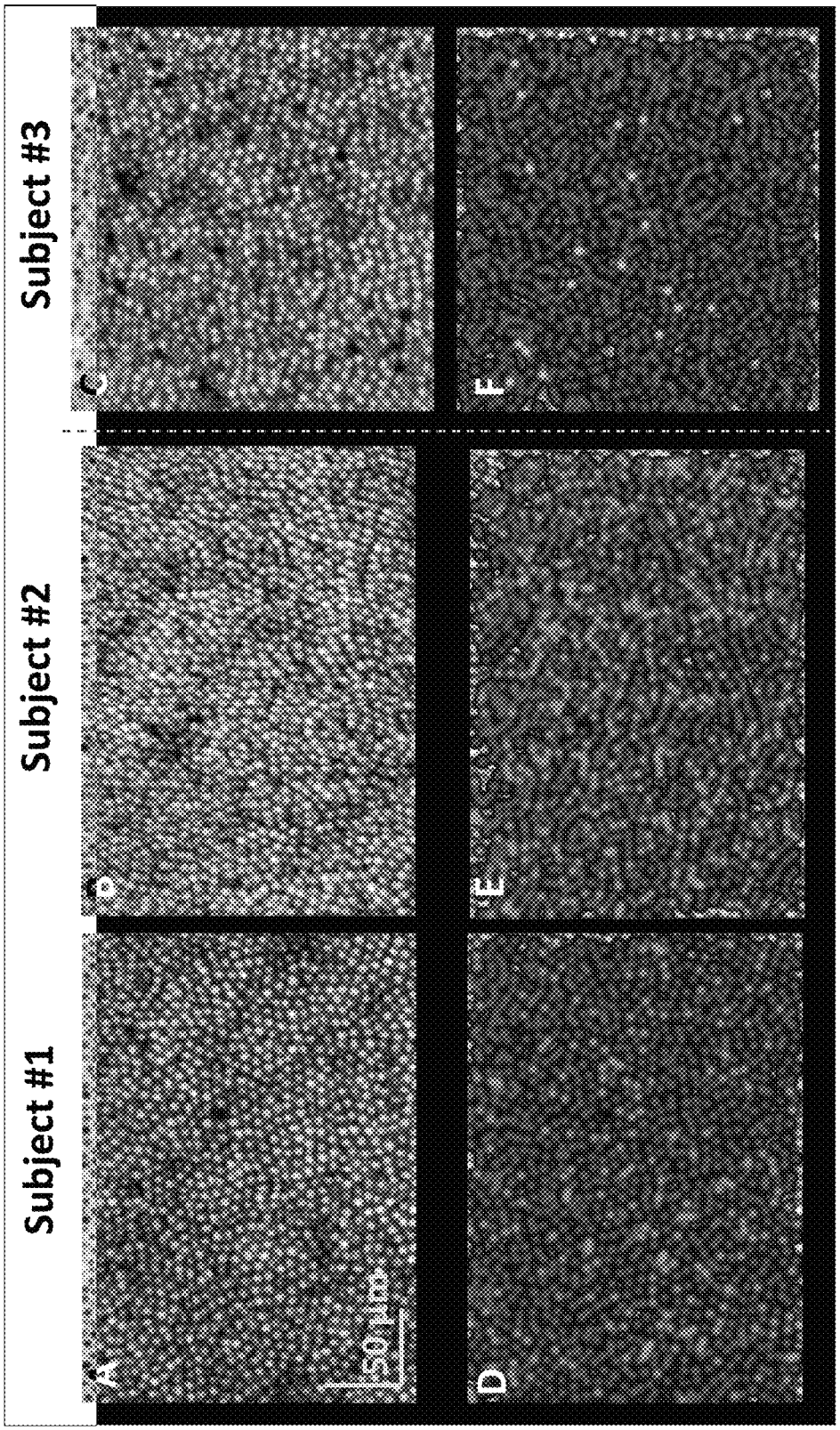

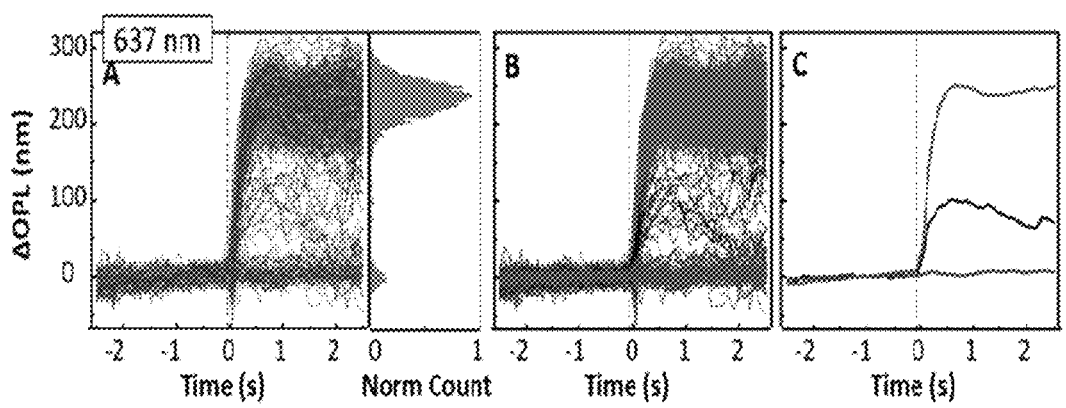
FIG. 52A          FIG. 52B          FIG. 52C
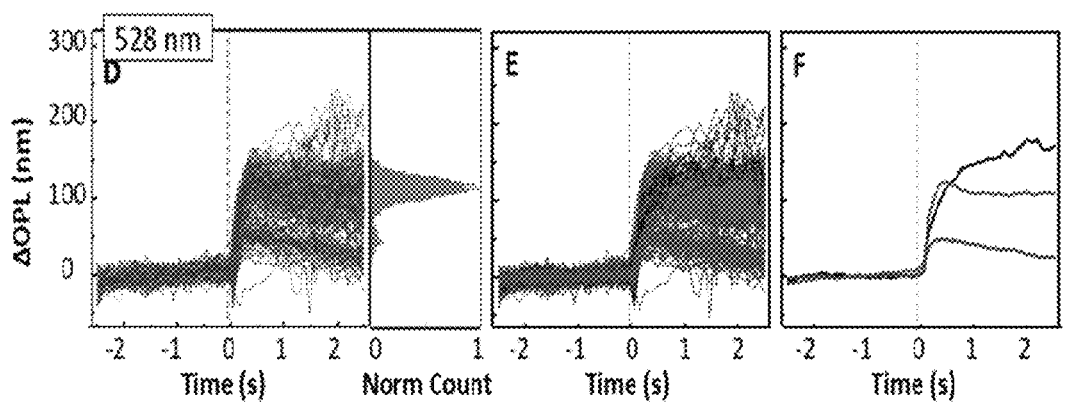
FIG. 52D          FIG. 52E          FIG. 52F
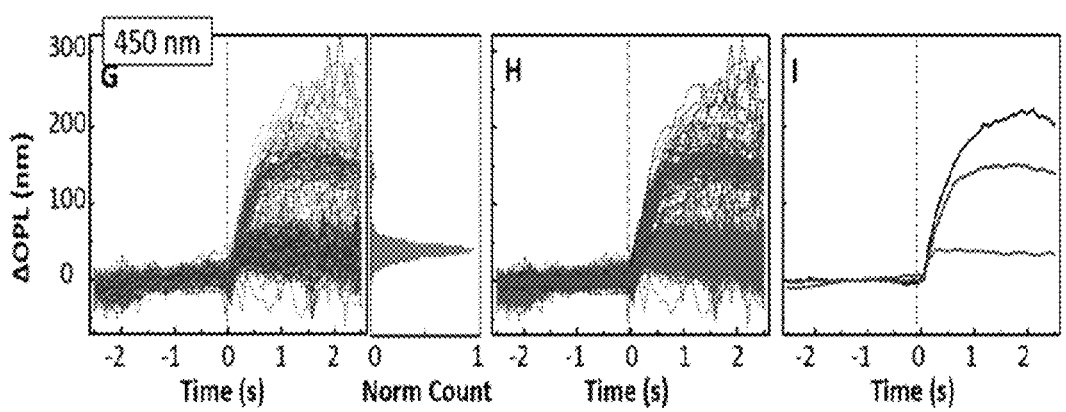
FIG. 52G          FIG. 52H          FIG. 52I

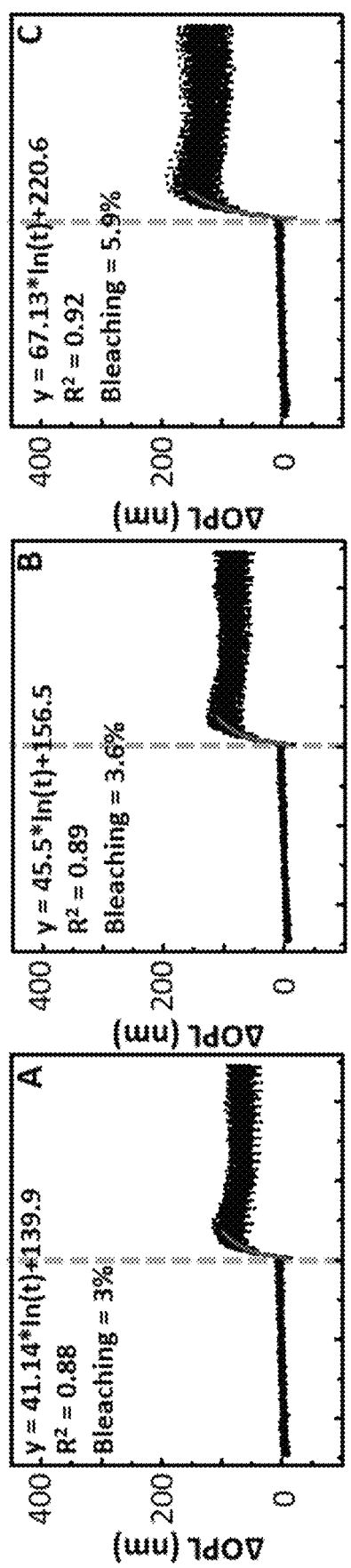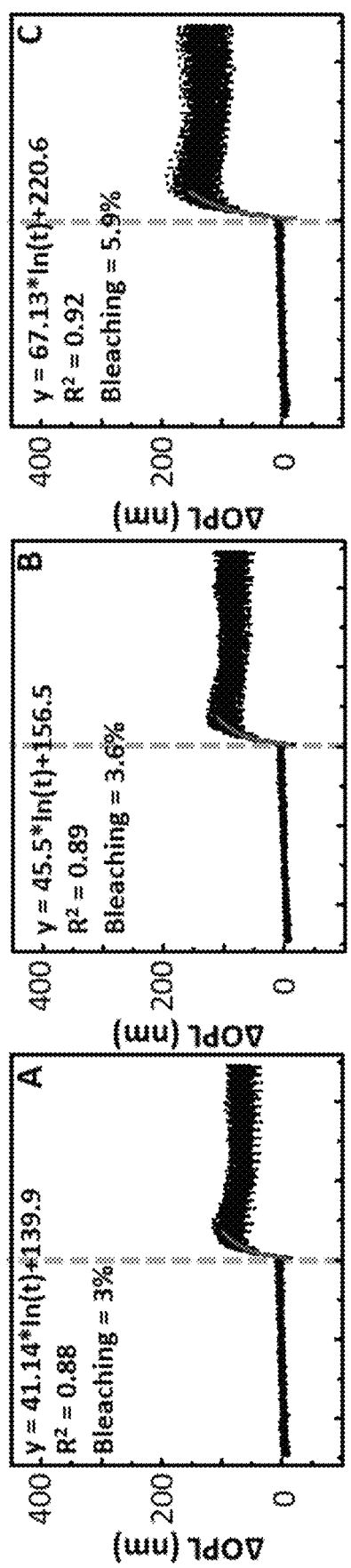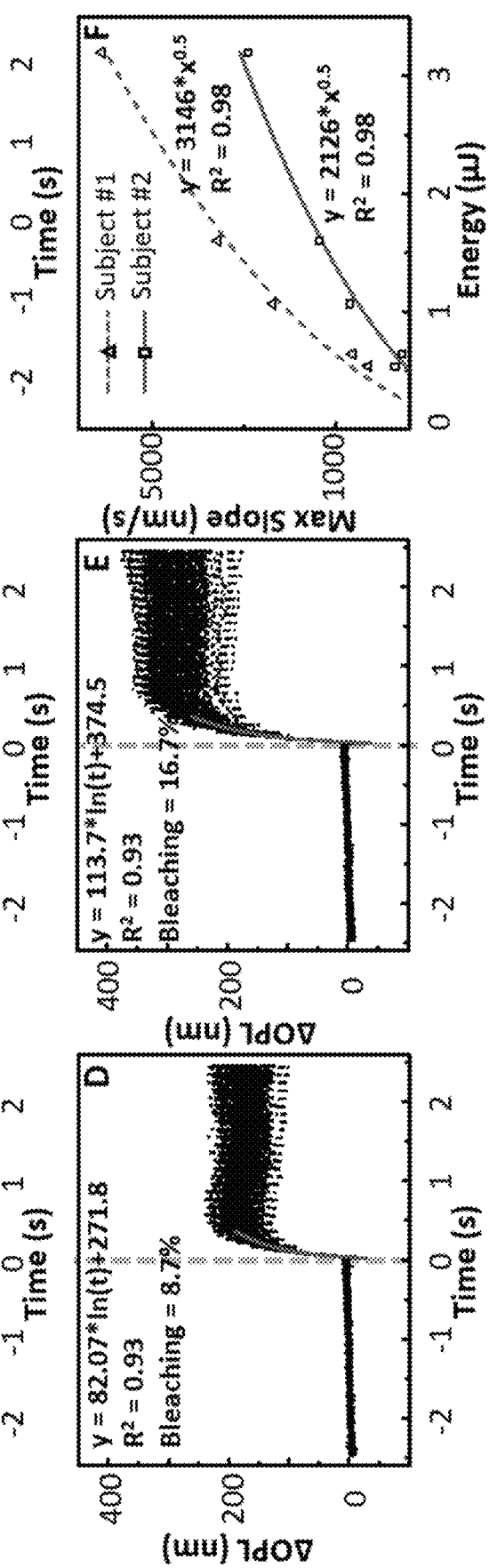

OPHTHALMOSCOPY METHOD

CROSS-REFERENCE TO RELATED APPLICATIONS

This application is a continuation-in-part application of PCT Application No. PCT/US2018/015256, entitled "OPHTHALMOSCOPY METHOD," filed on Jan. 25, 2018, which is based on and claims priority to U.S. Provisional Patent Application Ser. 62/450,161, entitled "OPHTHALMOSCOPY METHOD," filed on Jan. 25, 2017, the entire contents of which being hereby expressly incorporated herein by reference.

GOVERNMENT SUPPORT CLAUSE

This invention was made with government support under EY018339 awarded by the National Institutes of Health. The Government has certain rights in the invention.

TECHNICAL FIELD

The present invention relates generally to ophthalmoscopy methods and systems, and more particularly to ophthalmoscopy methods and systems that achieve the necessary resolution and sensitivity to noninvasively visualize a large fraction of cell types and cellular structures in the retina in human subjects.

BACKGROUND

Human vision starts in the eye, the primary site of almost all vision-related dystrophies. Many of the leading causes of blindness occur in the retina and include three high-priority eye diseases as defined by the World Health Organization: diabetic retinopathy, glaucoma, and age-related macular degeneration. One of the high-priority eye diseases, glaucoma, is a neurodegenerative disorder characterized by the progressive loss of retinal ganglion cells (RGC) and is a leading cause of blindness worldwide. While effective therapeutics exist, early detection of RGC loss has remained elusive regardless of method.

Histopathological studies have shown that disease onset in the retina begins at the level of individual cells and thus understanding abnormal structure and function requires visualization of changes in the microscopic realm. Translating this to eye care practice, the greatest promise for improved diagnosis, intervention, and treatment will be realized when detection and monitoring of retinal changes and assessing therapeutics occur at the cellular level. Translating to scientific discovery, the greatest promise for understanding the mechanisms of normal vision as well as dysfunctional vision will be realized when the associated retinal changes can also be detected and monitored at the cellular level.

Current clinical/commercial instrumentation have limited 3D spatial resolution and sensitivity, and while continuing to improve are still unable to image cellular details, where the greatest impact of eye care will occur. New optical modalities that are rapid, specific, and non-invasive hold the promise of greatly expanding our capability to monitor more accurately and completely the cellular retina. Today, a major effort is underway in the ophthalmologic research field to develop systems that address these limitations.

Recent developments in next-generation research-grade ophthalmoscopes take advantage of unique adaptive optics ("AO") and optical coherence tomography ("OCT") instrumentation in combination with sophisticated post processing algorithms that correct eye motion artifacts (image registration) and segment retinal layers of interest with subcellular accuracy, and then visualize and data mine the results (e.g., cell counts, densities, distributions). The recent developments have applications in a wide range of scientific and clinical uses that would benefit from visualizing the many cell types that compose the human retina (cell structure) and detecting their temporal dynamics (cell function). Different embodiments of the ophthalmoscopy method are described below for imaging cells of different type and for imaging cell structure and function. The first embodiment starts with imaging retinal pigment epithelial ("RPE") cells.

The RPE is a monolayer of cuboidal cells that lie immediately posterior to and in direct contact with photoreceptors. Retinal pigment epithelium has a fundamental role in the support and maintenance of photoreceptors and choriocapillaris. Its role is diverse, including nutrient and waste transport, reisomerization of all-trans-retinal, phagocytosis of shed photoreceptor outer segments, ion stabilization of the subretinal space, secretion of growth factors, and light absorption. It long has been recognized that dysfunction of any one of these can lead to photoreceptor degeneration and the progression of retinal disease, most notably age-related macular degeneration, but also Best's disease, Stargardt's disease, retinitis pigmentosa, and others. Much of what is known about the RPE and its interaction with photoreceptors comes either from in vitro studies using cultured RPE or animal models. While these studies use powerful methods, they are invasive, ultimately destroying the tissue, and require extrapolation to not only the in vivo case, but to the human eye. Over the last three decades, noninvasive optical imaging methods have been established to probe properties of the RPE in the living human eye using autofluorescence, multiply scattered light, and thickness segmentation.

The above-mentioned recent developments in high-resolution AO imaging systems have advanced RPE imaging to the single cell level, providing the first observations of individual RPE cells and cell distributions in the living human eye. Such observations hold considerable promise to elucidating age and disease related changes in RPE cell structure and density, both of which remain poorly understood. The ability to measure the same tissue repeatedly in longitudinal studies makes AO imaging systems attractive for assessing disease progression and treatment efficacy at the cellular level. Despite this potential and early success, however, RPE imaging remains challenging and has been largely confined to imaging select retinal locations of young, healthy subjects.

Regardless of the AO imaging modality used, two fundamental properties of the retina inhibit RPE imaging: the waveguide nature of photoreceptors that obscure spatial details of the underlying RPE mosaic and the low intrinsic contrast of RPE cells. Direct imaging of RPE cells with AO scanning laser ophthalmoscopy ("AO-SLO") has been demonstrated under restricted conditions where the photoreceptors are absent, as for example in localized regions of diseased retina, and in the scleral crescent in the normal retina. For the rest of the retina, other more advanced techniques are required. A dual-beam AO-SLO has been used with autofluorescence of lipofuscin to enhance RPE cell contrast, providing the most detailed study to date of the RPE mosaic in the living primate eye. Extension of this method to more clinical studies, however, remains challenged by the intrinsically weak autofluorescent signal and difficulty to image near the fovea owing to the strong excitation light that bleaches photopigment, causes subject discomfort, and is absorbed by the macular pigment. Researchers have demonstrated direct resolution of the RPE mosaic using dark-field AO-SLO with near-infrared light, though leakage from adjacent choroid and photoreceptors reflections could not be eliminated.

Adaptive optics optical coherence tomography ("AO-OCT") also has been investigated in large part because of its micrometer-level axial resolution that can section the narrow RPE band and avoid reflections from other retinal layers. However, speckle noise intrinsic to OCT masks retinal structures of low contrast, for example, RPE cells. Attempts to minimize this noise have included bandpass filters centered about the expected fundamental frequency of the RPE mosaic. These first AO-OCT approaches revealed the complexity of the problem and the need for improvements.

SUMMARY

The present disclosure provides, among other things, new methods based on AO-OCT approach that permits visualization of individual RPE cells, RGCs and many other retinal cells in vivo and thus provides the potential for direct detection of cell loss. Additionally, the present disclosure uses singly scattered light and produces images of unprecedented clarity of translucent retinal tissue. This permits morphometry of GCL somas across the living human retina. Among other things, the present disclosure overcomes the aforementioned obstacles by combining AO and OCT (AO-OCT) to achieve high lateral and axial resolution and high sensitivity, using 3D subcellular image registration to correct eye motion, and using organelle motility inside GCL somas to increase cell contrast. This imaging modality enables light microscopy of the living human retina, a tool for fundamental studies linking anatomical structure with visual function. High-resolution images of retinal neurons in living eyes also promise improved diagnosis and treatment monitoring of GC and axonal loss in diseases of the optic nerve such as glaucoma and other neurodegenerative disorders such as Alzheimer's disease, Parkinson's disease, and multiple sclerosis.

According to one embodiment, the present disclosure provides an ophthalmoscopy method, comprising: providing an adaptive optics optical coherence tomography (AO-OCT) system; imaging retinal locations of a living subject using the AO-OCT system; for each retinal location, acquiring AO-OCT video using the AO-OCT system focused at a retinal depth at which cells are to be imaged; registering volumes in three dimensions; averaging registered volumes across time points spaced such that natural motion of soma organelles enhances contrast between somas in retinal cells; using spatial coordinates of the somas to determine soma stack depth, density and diameter; and determining cell density measurements. In one aspect of this embodiment, the cells to be imaged are ganglion cells in the retinal ganglion cell (RGC) layer. In another aspect, the retinal locations included locations across a posterior pole of a human eye. In another aspect, using spatial coordinates of the somas includes determining at least one of soma size, density, reflectance and cell type.

In another embodiment, an ophthalmoscopy method is provided, comprising: segmenting contributions of RPE cells from rod outer segment tips; averaging a registered RPE signal across time points spaced such that natural motion of cell organelles enhances cell contrast; and characterizing a three-dimensional reflectance profile of individual RPE cells. In one aspect of this embodiment, characterizing a three-dimensional reflectance profile of individual RPE cells comprises characterizing a contribution of rod outer segment tips, RPE cell packing geometry, and a spatial relation to overlying cone photoreceptors In yet another embodiment, the present disclosure provides an ophthalmoscopy system, comprising: an optical coherence tomography camera equipped with adaptive optics; a controller comprising registration software to correct eye motion to sub-cellular accuracy for stabilizing and tracking of cells in 4D, a parallel computing module for real-time reconstruction and display of retinal volumes, and at least one algorithm for visualizing and quantifying cells and cellular structures, including extracting biomarkers that reflect cell morphology and physiology.

In still another embodiment, the present disclosure provides a method for observing ganglion cells in a living human eye, comprising: using an adaptive optics optical coherence tomography (AO-OCT) system to image a volume of a retinal patch including a ganglion cell layer (GCL); using 3D subcellular image registration to correct for eye motion, including digitally dissecting the imaged volume; and using organelle motility inside GCL somas to increase cell contrast. In one aspect of this embodiment, a 3D resolution of the AO-OCT system is at least 2.4×2.4×4.7 µm3 in retinal tissue. In another aspect, using organelle motility includes averaging images of the digitally dissected imaged volume to reduce speckle noise of the images. In a variant of this aspect, averaging images includes averaging images from more than 100 volumes of the retinal patch to increase clarity of the GCL somas. In yet another aspect, the GCL somas are one of stacked on each other, laying beneath a nerve fiber layer (NFL), or aggregated at a foveal rim of a macula. In still another aspect, the volume covers a 1.5°×1.5° field of view of a retina. In another aspect of this embodiment, using 3D subcellular image registration includes obtaining videos of the volume over a time period and generating cross-sectional scans of the volume by sampling the video.

In another embodiment, the present disclosure provides a system for observing ganglion cells in a living human eye, comprising: an adaptive optics optical coherence tomography (AO-OCT) system configured to image a volume of a retinal patch including a ganglion cell layer (GCL); and an image post-processor configured to provide 3D subcellular image registration to correct for eye motion, including by digitally dissecting the imaged volume; the image post-processor being further configured to use organelle motility inside GCL somas to increase cell contrast. In one aspect of this embodiment, a 3D resolution of the AO-OCT system is at least 2.4×2.4×4.7 µm3 in retinal tissue. In another aspect, the image post-processor is configured to average images of the digitally dissected imaged volume to reduce speckle noise of the images. In a variant of this aspect, the image post-processor averages images from more than 100 volumes of the retinal patch to increase clarity of the GCL somas. In another aspect of this embodiment, the GCL somas are one of stacked on each other, laying beneath a nerve fiber layer (NFL), or aggregated at a foveal rim of a macula. In another aspect, the volume covers a 1.5°×1.5° field of view of a retina. In still another aspect, the 3D subcellular image registration includes obtaining videos of the volume over a time period and generating cross-sectional scans of the volume by sampling the video.

In yet another embodiment, a method of classifying cone photoreceptors in the living human eye from photostimulation-induced phase dynamics is provided, comprising: measuring optical path length changes occurring inside cone photoreceptors during photoactivation to identify cone spectral types; wherein measuring optical path length changes includes measuring optical path length changes in terms of an equivalent phase change by combining adaptive optics (AO) and phase sensitive optical coherence tomography (OCT) to reveal individual cone reflections in 3D. One aspect of this embodiment further comprises using a single superluminescent diode with a central wavelength of about 790 nm and a bandwidth of about 42 nm for AO-OCT imaging. Another aspect further comprises using three fiber-based LED sources with spectra of 450±8 nm, 528±12 nm, and 637±12 nm, respectively, for stimulating cone photoreceptors. A variant of this aspect further comprises estimating a proportion of photopigment bleached by the stimulation of the cone photoreceptors according to the equation:

$$-\frac{dp}{dt} = \frac{Ip}{Q_e} - \frac{1-p}{t_0}$$

wherein p is the proportion of unbleached photopigment, I is the retinal illuminance, $Q_e$ is a constant that denotes the flash energy required to bleach p from 1 to $e^{-1}$, and $t_0$ is the time constant of pigment regeneration. Another aspect of this embodiment further comprises classifying cone spectral type using slow dynamics of the cone photoreceptors by computing an average response for each cone. Another aspect further comprises classifying cone spectral type using fast dynamics of the cone photoreceptors by computing an average response over individual B-scans from a volume containing light stimulation for each cone.

In still another embodiment, the present disclosure provides a method for measuring temporal dynamics of cells, comprising: using an adaptive optics optical coherence tomography (AO-OCT) system operated at a center wavelength of about 790 nm to acquire volume videos at a location temporal to a fovea; registering the volume videos to a reference volume to reduce motion artifacts; characterizing fast temporal dynamics using an auto-correlation analysis to determine time constants for at least one of a nerve fiber layer, a ganglion cell layer and an inner plexiform layer; and characterizing slow temporal dynamics using temporal speckle contrast on pixels of the volume videos, wherein the temporal speckle contrast includes determining a standard deviation of a reflectance amplitude and dividing the standard deviation by a mean of the reflectance amplitude.

According to the present disclosure, instrumentation and algorithm advances are disclosed to allow use of organelle motility intrinsic to the retinal tissue as a novel contrast mechanism. By doing so, it has been discovered that highly transparent cells in the retina can now be visualized in three dimensions in human subjects. This is achieved with the combinatory use of AO-OCT (to provide the necessary 3D optical resolution), organelle motility (to provide the necessary image contrast), post processing (to correct eye motion and increase method sensitivity), and visualization (to count and characterize the cells in 3D). This finding has exciting potential as most cell types in the retina are transparent.

In summary, a new ophthalmoscopy method is provided that achieves the necessary resolution and sensitivity to noninvasively visualize a large fraction of cell types and cellular structures in the retina in human subjects. Cell types and cellular structures successfully visualized to date include: microglial cells, retinal ganglion cell soma and axon bundles (and perhaps individual axons), amacrine cell soma, bipolar cell soma, horizontal cell soma, cone and rod photoreceptor segments, photoreceptor somas, photoreceptor axon bundles, retinal pigment epithelium cells, and cells that compose blood in the retinal and choroidal vasculature. Other cell types and cellular structures that will likely be seen using the teachings of the present disclosure include glial cells (Müeller cells, microglia, and astrocytes), choroidal melanocytes, etc.

While the new ophthalmoscopy methods of the present disclosure have been primarily used to study cell anatomy, recently the methods have also been shown useful for visualizing and quantifying cell physiology, which may ultimately hold the greatest promise for assessing cell health. The fundamental mechanisms of renewal and shedding of cone photoreceptors and organelle motility in RPE cells have been visualized and quantified. The organelle motility measurements while directed to RPE cells, are readily applicable to essentially any cell in the retina. Blood flow dynamics in the retinal vasculature and choriocapillaris have also been measured.

As described below, the present disclosure combines AO-OCT with subcellular registration and segmentation. First, this enables segmentation of contributions of RPE cells from rod outer segment tips (ROST), which for conventional OCT are unresolved and identified as a single band by the International Nomenclature for Optical Coherence Tomography Panel. Second, it enables averaging of the registered RPE signal across time points sufficiently spaced that the natural motion of cell organelles enhanced cell contrast. With these methods, the three-dimensional (3D) reflectance profile of individual RPE cells may be characterized, including the contribution of ROST, as well as RPE cell packing geometry, and spatial relation to the overlying cone photoreceptors.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The above-mentioned and other features of this disclosure and the manner of obtaining them will become more apparent and the disclosure itself will be better understood by reference to the following description of embodiments of the present disclosure taken in conjunction with the accompanying drawings, wherein:

FIGS. 5A-C provides adaptive optics OCT cross-sectional and en face images extracted from the photoreceptor-RPE complex of a 48-year-old subject at eight retinal eccentricities;

FIG. 29F is an image of GCL somas;

FIG. 29G is an image of an IPL;

FIG. 40A-E provide en face images of the vitreous, NFL, GCL and IPL and a plot of correlation coefficients versus time;

FIG. 47J depicts the percent agreement of each matrix to the left of FIG. 47J;

FIG. 47K depicts the repeatability error quantified by comparing classification results of two independent subsets of videos (P1 and P2) obtained with the 637 nm stimulus, wherein each subset contains 7 videos;

FIGS. 49A-C are en face intensity images showing the mosaics of cone cells of three subjects, wherein the intensity images do not contain information that would allow the spectral type of the cone cells to be identified;

FIGS. 49D-F show the spectral type of the cone cells in FIGS. 49A-C as identified with an ophthalmoscopy method according to the present disclosure, wherein the cones are color coded on the basis of their spectral type (S=blue; M=green; L=red; Unidentified (U)=yellow);

FIGS. 52A-C are response traces for individual cones in a deuteranope for stimulation at 637 nm and 1.6 µJ;

FIGS. 52D-F are response traces for individual cones in a deuteranope for stimulation at 528 nm and 0.5 µJ;

FIGS. 52G-I are response traces for individual cones in a deuteranope for stimulation at 450 nm and 1.0 µJ;

FIGS. 57A-F are graphs depicting the phase response of cones shown in FIG. 44A reanalyzed to capture temporal dynamics up to the 3 KHz rate of the fast B-scans, wherein the flash energy used was 0.53 µJ (FIG. 57A), 0.64 µJ (FIG. 57B), 1.07 µJ (FIG. 57C), 1.60 µJ (FIG. 57D), and 3.20 µJ (FIG. 57E).

Figure 1A:
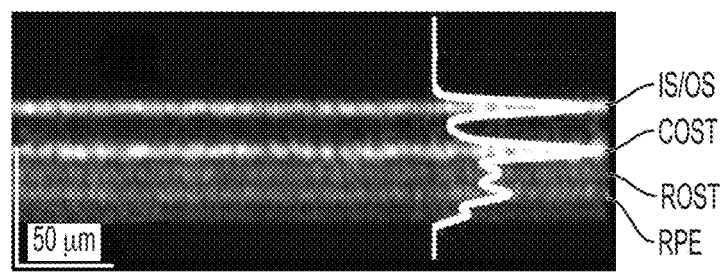
FIGS. 1A-E provide adaptive optics OCT cross-sectional and en face images extracted from the photoreceptor-RPE complex in a 25-year-old subject at 7° temporal retina.

While the present disclosure is amenable to various modifications and alternative forms, specific embodiments have been shown by way of example in the drawings and are described in detail below. The present disclosure, however, is not to limit the particular embodiments described. On the contrary, the present disclosure is intended to cover all modifications, equivalents, and alternatives falling within the scope of the appended claims.

DETAILED DESCRIPTION

One of ordinary skill in the art will realize that the embodiments provided can be implemented in hardware, software, firmware, and/or a combination thereof. Programming code according to the embodiments can be implemented in any viable programming language such as C, C++, Python, HTML, XTML, JAVA or any other viable high-level programming language, or a combination of a high-level programming language and a lower level programming language.

As used herein, the modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range "from about 2 to about 4" also discloses the range "from 2 to 4."

The design of ophthalmoscopic cameras for cellular-level imaging of the retina is truly challenging since the instrument must satisfy demanding criteria in the areas of (1) lateral resolution, (2) penetration through absorbers and scatterers in the eye, (3) optical sectioning (equivalently depth resolution), (4) speed, (5) sensitivity with a limited light budget for safety, and (6) contrast generation through selected imaging modalities. Successful visualization of individual retinal cells requires that the camera meet specific criteria in each of these six areas. In addition there are practical requirements as for example the need for real-time feedback to visualize, locate and track cells during patient imaging.

The present disclosure meets these camera criteria by using (1) optical coherence tomography equipped with adaptive optics, (2) custom registration software to correct eye motion to sub-cellular accuracy for stabilizing and tracking of cells in 4D, (3) parallel computing for real-time reconstruction and display of retinal volumes, and (4) algorithms and methods for visualizing and quantifying cells and cellular structures, including extracting biomarkers that reflect cell morphology and physiology. Details of these steps for visualizing and characterizing retinal pigment epithelium and photoreceptor cells are described in Liu Z, Kocaoglu O P, Miller D T. 3*D Imaging of Retinal Pigment Epithelial Cells in the Living Human Retina*. Invest Ophthalmol Vis Sci. 2016; 57(9):OCT533-43. doi:10.1167/iovs.16-19106, the entire contents of which are incorporated herein by reference. Details of these steps for visualizing and characterizing retinal ganglion cells and other inner retinal cells (microglial cells, displaced amacrine cells, displace retinal ganglion cells, and bipolar cells) are described in Liu, Z., Kurokawa, K., Zhang, F., Lee, J. J., & Miller, D. T. (2017), Imaging and quantifying ganglion cells and other transparent neurons in the living human retina, Proceedings of the National Academy of Sciences of the United States of America, 114(48), 12691-12695. https://doi.org/10.1073/pnas.1711734114.

The retinal pigment epithelial (RPE) is a monolayer of cuboidal cells that lies immediately posterior to and in direct contact with photoreceptors. Retinal pigment epithelium has a fundamental role in the support and maintenance of photoreceptors and choriocapillaris. Its role is diverse, including nutrient and waste transport, reisomerization of all-trans-retinal, phagocytosis of shed photoreceptor outer segments, ion stabilization of the subretinal space, secretion of growth factors, and light absorption. It long has been recognized that dysfunction of any one of these can lead to photoreceptor degeneration and the progression of retinal disease, most notably age-related macular degeneration, but also Best's disease, Stargardt's disease, retinitis pigmentosa, and others.

Much of what is known about the RPE and its interaction with photoreceptors comes either from in vitro studies using cultured RPE or animal models. While these studies use powerful methods, they are invasive, ultimately destroying the tissue, and require extrapolation to not only the in vivo case, but to the human eye. Over the last three decades, noninvasive optical imaging methods have been established to probe properties of the RPE in the living human eye using autofluorescence, multiplied scattered light, and thickness segmentation.

In recent years, high-resolution adaptive optics (AO) imaging systems have advanced RPE imaging to the single cell level, providing first observations of individual RPE cells and cell distributions in the living human eye. Such observations hold considerable promise to elucidating age and disease related changes in RPE cell structure and density, both of which remain poorly understood. The ability to measure the same tissue repeatedly in longitudinal studies makes AO imaging systems attractive for assessing disease progression and treatment efficacy at the cellular level. Despite this potential and early success, however, RPE imaging remains challenging and has been largely confined to imaging select retinal locations of young, healthy subjects.

Regardless of the AO imaging modality used, two fundamental properties of the retina inhibit RPE imaging: the waveguide nature of photoreceptors that obscure spatial details of the underlying RPE mosaic and the low intrinsic contrast of RPE cells. Direct imaging of RPE cells with AO scanning laser ophthalmoscopy (AO-SLO) has been demonstrated under restricted conditions where the photoreceptors are absent, as for example in localized regions of diseased retina, and in the scleral crescent in the normal retina. For the rest of the retina, other more advanced techniques are required. A dual-beam AOSLO has been used with autofluorescence of lipofuscin to enhance RPE cell contrast, providing the most detailed study to date of the RPE mosaic in the living primate eye. Extension of this method to more clinical studies, however, remains challenged by the intrinsically weak autofluorescent signal and difficulty to image near the fovea owing to the strong excitation light that bleaches photopigment, causes subject discomfort, and is absorbed by the macular pigment. More recently, researchers demonstrated direct resolution of the RPE mosaic using dark-field AO-SLO with near-infrared light, though leakage from adjacent choroid and photoreceptors reflections could not be eliminated.

Adaptive optics optical coherence tomography (AO-OCT) also has been investigated in large part because of its micrometer-level axial resolution that can section the narrow RPE band and avoid reflections from other retinal layers. However, speckle noise intrinsic to OCT masks retinal structures of low contrast, for example, RPE cells. Attempts to minimize this noise have included bandpass filters centered about the expected fundamental frequency of the RPE mosaic. These first AO-OCT approaches revealed the complexity of the problem and the need for improvements.

According to the present disclosure, a solution was to combine AO-OCT with subcellular registration and segmentation. As indicated above, this enables segmentation of contributions of RPE cells from rod outer segment tips (ROST), which for conventional OCT are unresolved and identified as a single band by the International Nomenclature for Optical Coherence Tomography Panel. It also enables averaging of the registered RPE signal across time points sufficiently spaced that the natural motion of cell organelles enhanced cell contrast. This permits characterization of the three-dimensional (3D) reflectance profile of individual RPE cells, including the contribution of ROST, as well as RPE cell packing geometry, and spatial relation to the overlying cone photoreceptors.

Description of AO-OCT Imaging System

The AO-OCT system used in the study described below has been described at various levels of advancements in the following three publications:

(a) Liu Z, Kocaoglu O P, Miller D T, In-the-plane design of an off-axis ophthalmic adaptive optics system using toroidal mirrors, Biomed Opt Express. 2013; 4:3007-3029, (b) Kocaoglu O P, Turner T L, Liu Z and Miller D T, Adaptive optics optical coherence tomography at 1 MHz. Biomedical Optics Express, 2014; 5(12): 4186-4200, and (c) Liu Z, Kurokawa K, Zhang F, Lee J J, and Miller D T, Imaging and quantifying ganglion cells and other transparent neurons in the living human retina, 2017; 114(48): 12803-12808, the entire disclosure of which being expressly incorporated herein by reference. The AO-OCT system used a single light source, a superluminescent diode with central wavelength of 790 nm and bandwidth of 42 nm, for AO-OCT imaging and wavefront sensing. Nominal axial resolution of the system in retinal tissue (n=1.38) was 4.7 micron with axial pixel sampling at 0.93 micron/px. The systems acquired A-scans at a rate of 250 KHz. The data stream from the system was processed and displayed using custom CUDA software developed for parallel processing by an NVIDIA Titan Z general purpose graphic processing unit. Real-time visualization of A-scans, fast and slow B-scans, and C-scan (en face) projection views of the retinal layers of interest occurred at 20 frames per second.

Experimental Design and Subjects

In one embodiment of the present disclosure, six subjects, ranging in age from 25 to 61 years (S1=25, S2=31, S3=35, S4=36, S5=48, and S6=61 years old) and free of ocular disease, were recruited for the study. All subjects had best corrected visual acuity of 20/20 or better. Eye lengths ranged from 23.56 to 26.07 mm (S1=24.04, S2=23.73, S3=24.96, S4=26.07, S5=25.4, and S6=23.56 mm) as measured with the IOLMaster (Zeiss, Oberkochen, Germany) and were used to correct for axial length differences in scaling of the retinal images following the method described in Bennett A G, Rudnicka A R, Edgar D F, *Improvements on Littmann method of determining the size of retinal features by fundus photography*, Graefes Arch Clin Exp Ophthalmol. 1994; 232:361-367, the entire disclosure of which being expressly incorporated herein by reference.

Intensity of the AO-OCT beam was measured at 400 µW at the cornea and below the safe limits established by the American National Standards Institute (ANSI) for the retinal illumination pattern used and length of the experiment (details below). The right eye was cyclopleged and dilated with one drop of tropicamide 0.5% for imaging and maintained with an additional drop every hour thereafter. The eye and head were aligned and stabilized using a bite bar mounted to a motorized XYZ translation stage.

Adaptive optics OCT volumes were acquired at two retinal locations, 3° and 7° temporal to the fovea, on all subjects. These locations were selected as the RPE is known to have different concentrations of melanin and lipofuscin, and, thus, may provide a means to differentiate light scatter contributions from the two organelles. Concentrations follow an inverse relation with melanin peaking in the fovea and lipofuscin in the periphery, generally at 7° or beyond. This inverse relation is largely age-independent albeit the overall concentrations of melanin and lipofuscin are age-sensitive with melanin decreasing and lipofuscin increasing. While imaging the foveal center would have maximized the difference in melanin concentration with that at 7°, AO-OCT images at 3° are easier to process because the AO-OCT scan pattern is less distracting to the subject and results in fewer eye motion artifacts. For each retinal location, 30 to 35 AO-OCT videos (each ~4 seconds in duration) were acquired at 3-minute intervals over approximately 90 minutes. For one subject (S5), the 90-minute experiment was repeated 2 days later resulting in a total of 64 AO-OCT videos for that subject's 3° location. Each video consisted of 10 volumes acquired at a rate of 2.8 Hz. Volumes were 1°×1° at the retina and A-scans sampled at 1 µm/px in both lateral dimensions. A fast B-scan rate of 833 Hz reduced, but did not eliminate, eye motion artifacts.

Before collection of the AO-OCT volumes, system focus was adjusted to optimize cone image quality, determined by visual inspection of cones in en face images that were projected axially through the portion of the AO-OCT volume that contained the cone inner/outer segment junction (IS/OS; also called the ellipsoid zone) and cone outer segment tip (COST) reflectance bands.

3D Image Registration and Data Analysis

Three-dimensional registration was applied to the entire AO-OCT volume, followed by layer segmentation and data analysis to the following four principle reflections: IS/OS, COST, ROST, and RPE. These three processing steps were realized with custom algorithms developed in MATLAB (Mathworks, Natick, Mass., USA). Registration and segmentation were based upon registration algorithms described in Jonnal R S, Kocaoglu O P, Wang Q, Lee S, Miller D T, *Phase sensitive imaging of the outer retina using optical coherence tomography and adaptive optics*, Biomed Opt Express. 2012; 3: 104-124 and Kocaoglu O P, Ferguson R D, Jonnal R S, et al. *Adaptive optics optical coherence tomography with dynamic retinal tracking*, Biomed Opt Express. 2014; 5:2262-2284 ("the registration and segmentation publications"), the entire disclosures of which being expressly incorporated herein by reference. The data analysis algorithms were new for this study.

The best AO-OCT volume of each 10-volume video was selected based on the criteria of cone visibility in the en face projection, minimal eye motion artifacts, and common overlap with the other volumes selected for the same retinal location. For some time points imaged, the selection criteria could not be met and therefore, volumes were not selected for these points. This selection resulted in 24 to 35 volumes for each retinal location with subject S5 having 64 volumes for 3° because of the additional imaging session. All further processing was applied to these selected volumes.

Part of the method to individuate RPE cells was correction of eye motion artifacts in all three dimensions as these can be many times larger than the cellular features to be extracted from the volumes. For axial segmentation, each A-scan in the AO-OCT volume was first registered using a two-step iterative cross-correlation method. Next, the IS/OS, COST, ROST, and RPE layers were identified in each A-scan using an automated algorithm based on multiple one-dimensional cross-correlations.

Next, lateral eye motion was corrected using the stripe-wise registration algorithm disclosed in the registration and segmentation publications mentioned above. Because all pixels along an A-scan are acquired simultaneously, eye motion is the same along the entire A-scan. Thus, registration of the ROST and RPE images entailed stripe-wise registration of the projected cone layers (IS/OS+COST) from which registration coordinates then were applied directly to the underlying ROST and RPE layers. In principle, the stripe-wise registration could have been applied directly to ROST and RPE, but lack of robust image features in either case make this difficult and there is little benefit to do so.

Figures 1B, 1C, 1D:
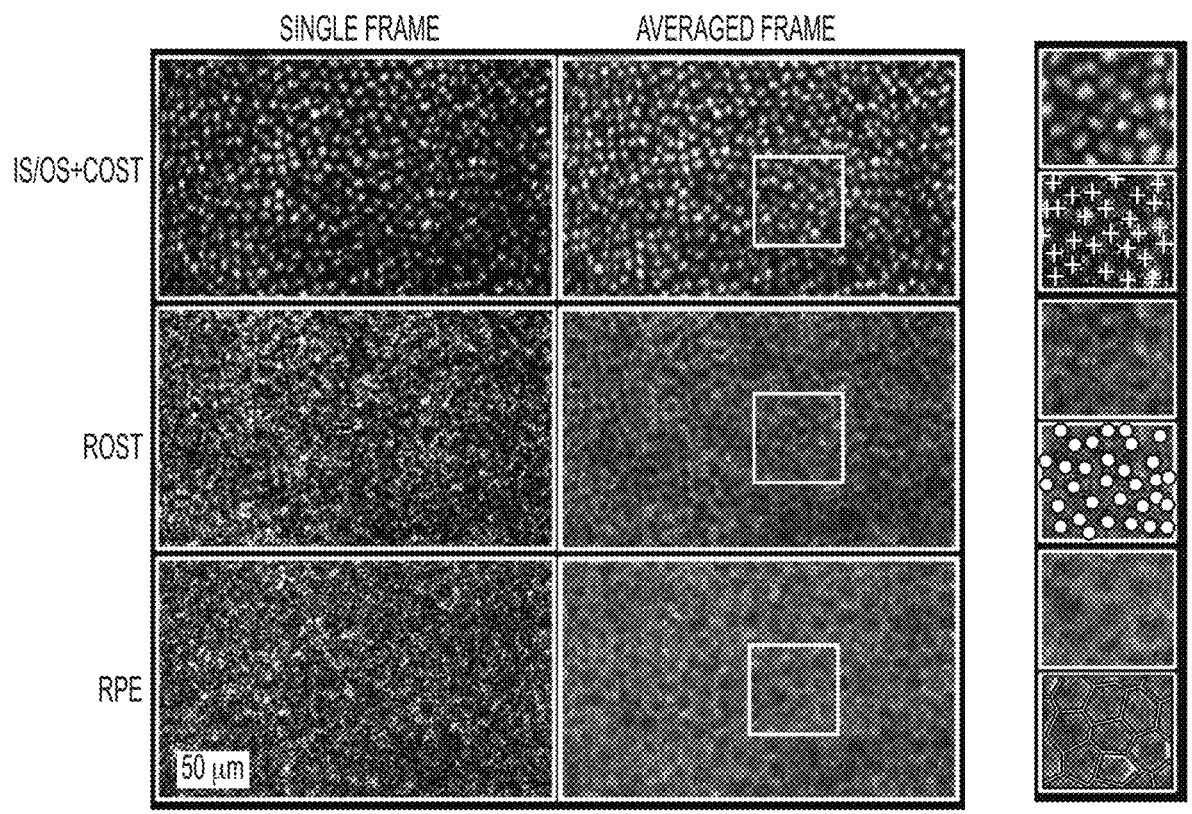

Finally, the motion-corrected cone (IS/OS+COST), ROST, and RPE images were averaged across the selected volumes to generate averaged, registered en face images for cone, ROST, and RPE, an example of which is given in FIGS. 1B-C. For reference purposes, the depth at which the en face images were extracted was measured relative to the IS/OS layer (zero location). The IS/OS was selected as the reference depth owing to its strong reflectance and narrow axial extent.

The geometric arrangement of cone and RPE cells was analyzed using Voronoi maps, a mathematical construct frequently used for quantifying cell association in retina tissue. Voronoi maps were generated using cone cell centers that were identified automatically in the AO-OCT images using previously described MATLAB code. Retinal pigment epithelial cell centers were selected manually. From these maps the following metrics were computed: Nearest neighbor distance (NND), number of nearest neighbors, mean of Voronoi side lengths, mean standard deviation of Voronoi side lengths, Voronoi cell area, cell density, and cone-to-RPE ratio. Cell density was defined as the ratio of total number of RPE cells (selected cells in the Voronoi maps) to total area of RPE cells (summation of the selected cell areas). Cone-to-RPE ratio was defined as the ratio of cone to RPE cell densities.

Two-dimensional (2D) power spectra were computed of the cone, ROST, and RPE en face images and served three purposes: to compare frequency content of the three layers, quantify average RPE cell spacing and density, and determine signal-to-noise ratio (SNR) of the RPE signal in the images. Cell spacing was determined from the radius of the ring of concentrated energy in the power spectra corresponding to the cone and RPE mosaic fundamental frequencies. All conversions to row-to-row spacing assumed triangular packing. The SNR was defined as the RPE peak signal (cusp of concentrated energy) divided by the average noise floor in the power spectrum, and was calculated for different numbers of images averaged (1, 10, 24, and maximum images registered).

Additional 3D Data Analysis

To further characterize the ROST reflectance and axial separation of IS/OS, COST, ROST, and RPE with retinal eccentricity, AO-OCT data from a previously reported experiment (described in Liu Z, Kocaoglu O P, Turner T L, Miller D T, *Modal content of living human cone photoreceptors*, Biomed Opt Express. 2015; 6:3378-3404, the entire contents of which being expressly incorporated herein by reference) were reanalyzed for subject S5. In that study, AO-OCT volumes were acquired at eight retinal eccentricities along the temporal horizontal meridian (0.6°, 2°, 3°, 4°, 5.5°, 7°, 8.5°, and 10°). The additional retinal eccentricities (eight instead of two) and finer A-scan sampling (0.6 instead of 1.0 µm/px) provided better assessment of rod presence with eccentricity (including the rod-free zone) and individuation of rods. Best focus was placed at the photoreceptor layer. Note that because volume videos were acquired at effectively only one time point for each retinal location, the RPE cell mosaic could not be assessed.

At each retinal location, 10 AO-OCT volumes of the same video were axially registered and then from each an averaged A-scan and projected fast B-scan computed. For each A-scan, the IS/OS, COST, ROST, and RPE peak locations were identified manually and their depth location determined relative to IS/OS. Depth location was averaged over the 10 volumes. From the best volume (least apparent motion artifacts), en face images were extracted of cone and ROST layers, and then superimposed as a false-color image denoting depth.

Results

3D Imaging of Photoreceptor-RPE Complex

Volumetric patches of retina were successfully imaged and registered in all six subjects and two retinal eccentricities. Representative single and averaged, registered images acquired at 7° retinal eccentricity in one subject are shown in FIGS. 1A-E. The averaged B-scan and averaged A-scan profile in FIG. 1A reveal distinct reflectance bands within the photoreceptor-RPE complex. These are labeled IS/OS, COST, ROST, and RPE with their corresponding single-frame en face projections shown in FIG. 1B. As expected, the single en face frame (top of FIG. 1B) reveals a regular pattern of bright punctate reflections, each originating from an individual cone cell and consistent with that reported previously with AO-OCT. Unlike the cone reflection, a regular pattern is not evident in single-frame images of the ROST (middle of FIG. 1B) and RPE layers (bottom of FIG. 1B). However, a pattern emerges when registered images of the same patch are averaged. This is illustrated in FIG. 1C (middle and bottom images) for the averaging of 26 frames. Rod outer segment tips and RPE layers reveal a regular pattern, but with reflectance inverted from that of cones, that is, darkened punctate reflections in a bright surround. The ROST and RPE appear similar, not unexpected given they originate within the conventional RPE reflectance band and are separated in depth by just 10 µm.

Figure 1E:
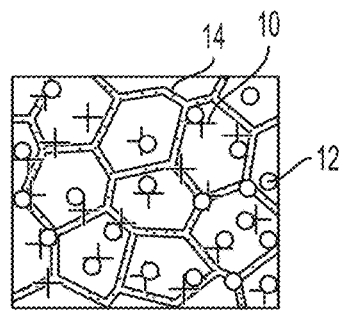

However, on closer inspection, the two mosaic patterns are spatially distinct, in terms of the location and spacing of the darkened punctate reflections. These differences, as well as those with the overlying cone mosaic pattern, are evident in FIGS. 1D-E. To aid the comparison, the bright spots in the cone projection and dark spots in the ROST and RPE layers (see FIG. 1D) are manually marked. FIG. 1E demonstrates the one-to-one correspondence between cones (crosses 10) and darkened spots (dots 12) in the ROST, with a pseudo-shadow typically forming underneath each cone. In contrast, no correspondence is apparent between cones (or equivalently their pseudo-shadow locations in ROST) and RPE (Voronoi map 14). In fact, for the magnified view shown, there are approximately two times more cones (bright spots) than dark spots in RPE.

Figure 2:
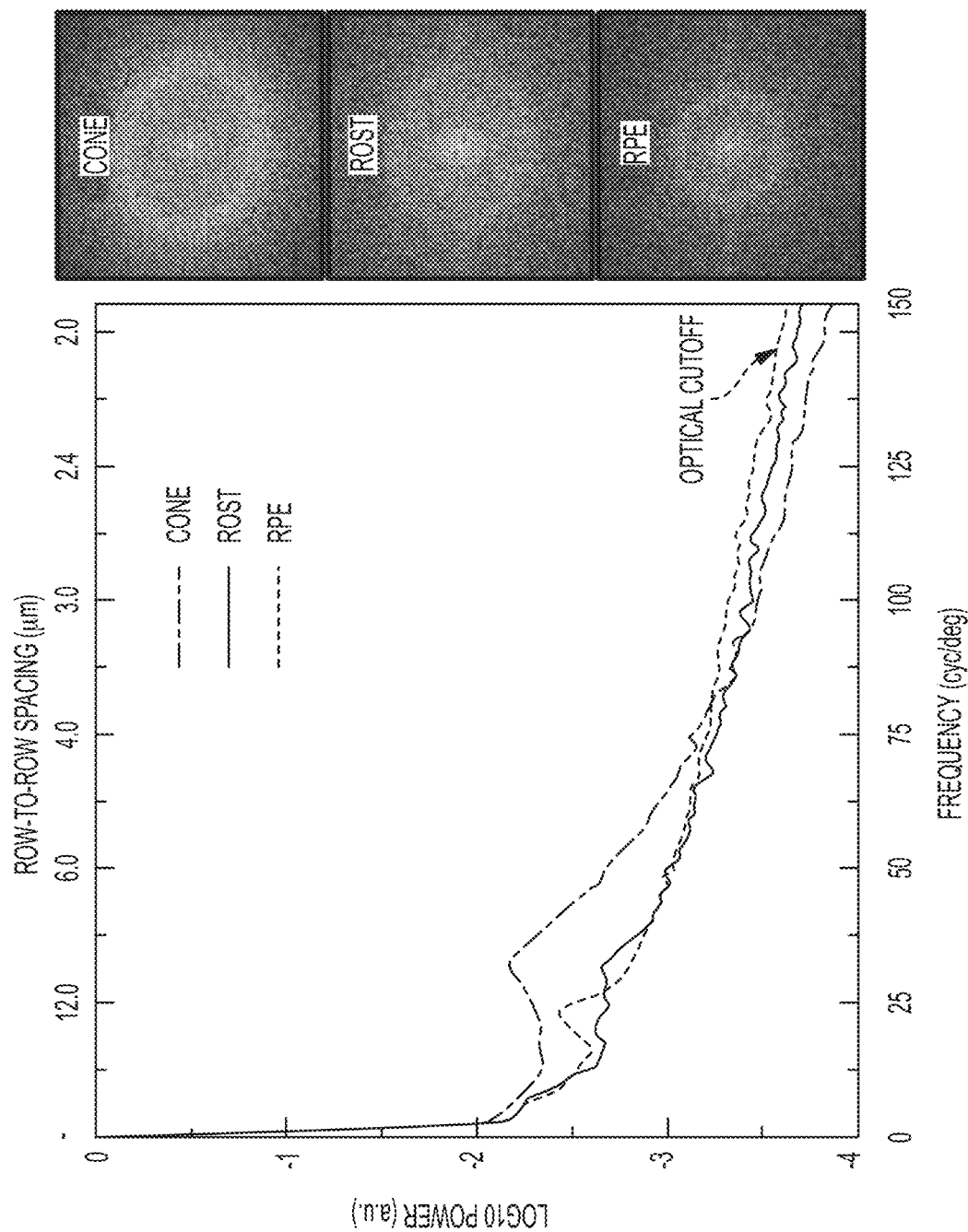
FIG. 2 is a graph of power spectra of en face images of a subject at 7° temporal retina.

FIG. 2 shows power spectra of the en face images in FIGS. 1B-C (cone projection, ROST, and RPE layers). Rings of concentrated energy are evident in the three power spectra, substantiating the observation of regular mosaics in the en face images of FIG. 1C. However, the rings of ROST and RPE locate at different frequencies in the power spectra, supporting the observation of different spatial cell arrangements in the two layers. The circumferential-averaged power spectra of cone and ROST (which has a less distinct cusp of energy) have local maxima at 31.8 cyc/deg (row-to-row spacing of 9.4 µm assuming triangular packing), while that of RPE has a local maxima at 23.4 cyc/deg (row-to-row spacing of 12.8 µm).

Figure 3:
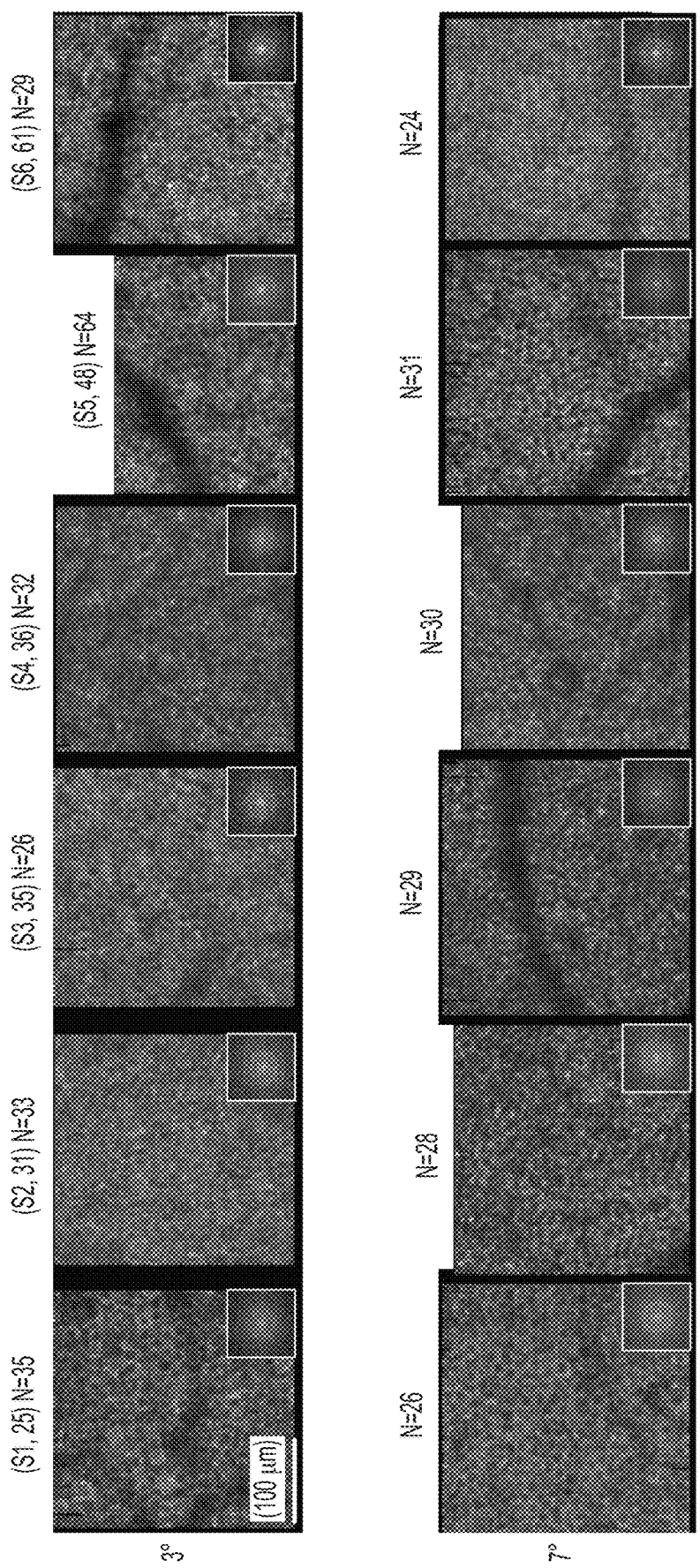
FIG. 3 provides averaged, registered RPE images for subjects imaged at 3° and 7° temporal to fovea.
Figure 4:
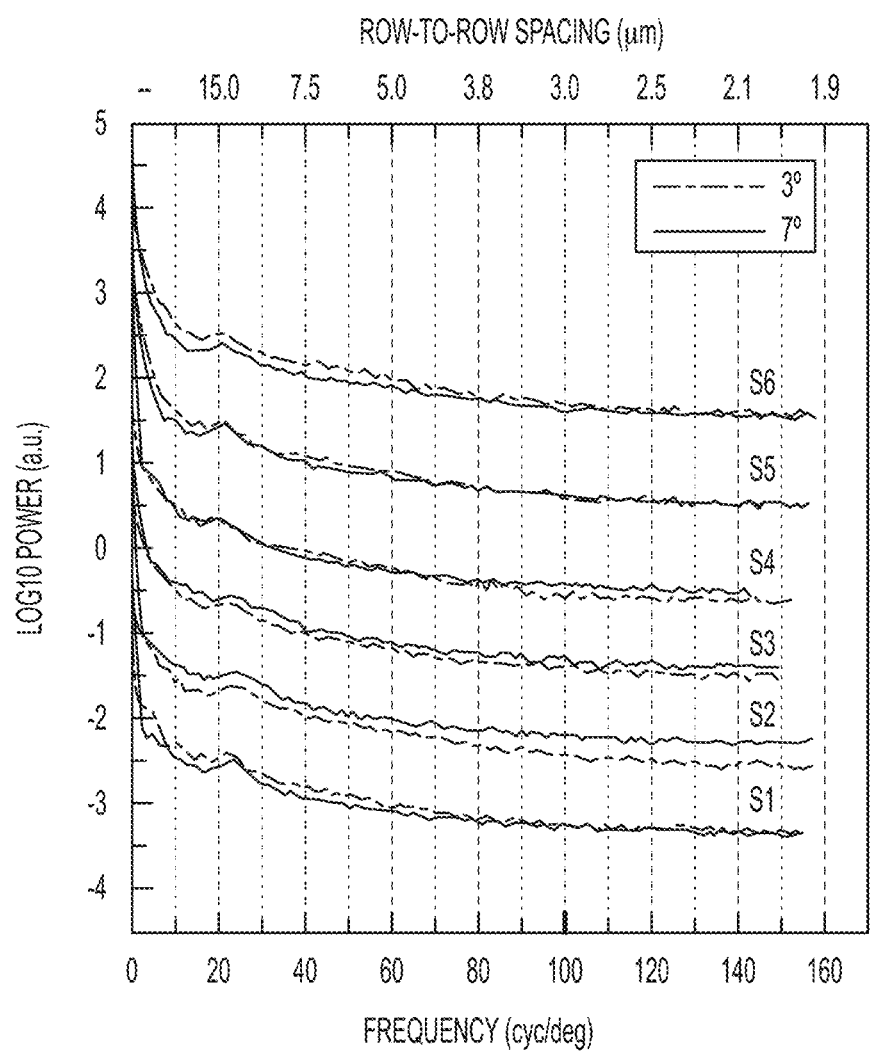
FIG. 4 is a graph of circumferential averages of the twelve 2D power spectra of FIG. 3.

Averaged, registered RPE images from all six subjects and at both retinal eccentricities are displayed in FIG. 3. While faint, a regular pattern of darkened spots is present in the 12 RPE images along with a concentrated ring of energy in the corresponding 2D power spectra. A more quantitative view of the power spectra is shown in FIG. 4, plotted as circumferential-averaged power with intersection of the ring evident as a cusp in the trace. Assuming triangular spacing, Table 1 below converts these peak (fundamental) frequencies to row-to-row spacings resulting in 13.8+/−1.1 (3°) and 13.7+/−0.7 (7°) µm for the six subjects.

TABLE 1

Measured Row-To-Row Spacing
Based on Analysis of Power Spectra in FIG. 4

|  | S1 | S2 | S3 | S4 | S5 | S6 | Mean +/− SD |
|---|---|---|---|---|---|---|---|
| 3°, µm | 13.4 | 12.2 | 13.3 | 15.5 | 14.4 | 14.0 | 13.8 +/− 1.1 |
| 7°, µm | 12.8 | 13.0 | 13.4 | 14.6 | 14.0 | 14.3 | 13.7 +/− 0.7 |

These spacings are consistent with that expected of the RPE cell mosaic. Given that no other cellular structure are known at this depth in the retina with this regularity, the mosaic is interpreted to be the RPE cell mosaic and each darkened spot in the mosaic to be an individual RPE cell. To better characterize the retinal eccentricity dependence of ROST and RPE, FIGS. 5A-C present reanalysis of previously reported AO-OCT data on subject S5. Across the eight retinal eccentricities imaged, clear and systematic differences in ROST reflectance and axial separation of the layers are evident in cross-section (averaged A-scan and B-scan) and en face views.

Voronoi Analysis of RPE Layer

Figure 6E:
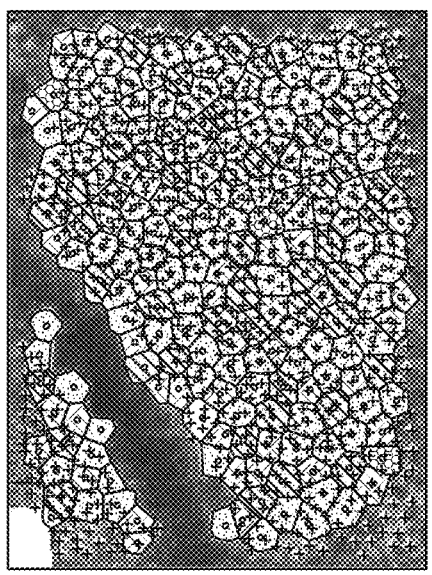
FIGS. 6A-F depicts direct spatial comparison on a cell-by-cell basis for the spatial arrangement of cone photoreceptors relative to the underlying RPE cells for a subject.
Figure 6C:
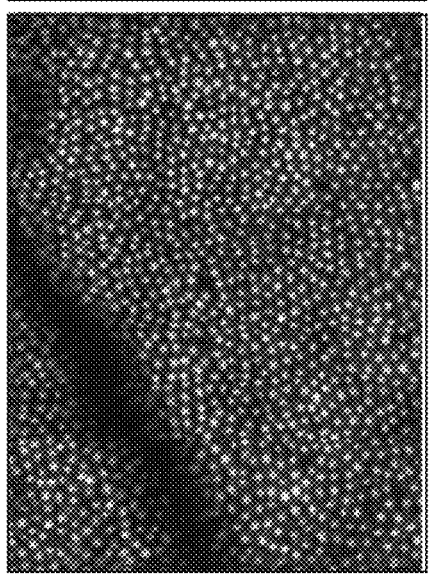
Figure 6A:
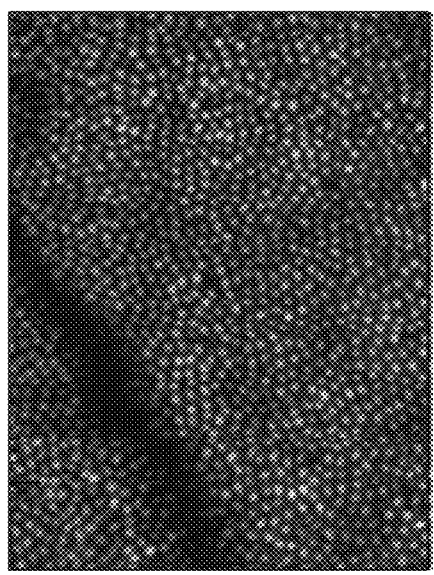
Figure 6F:
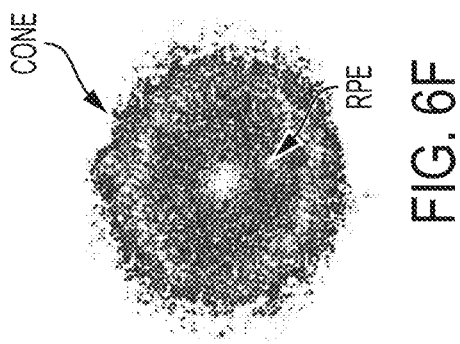
Figure 6D:
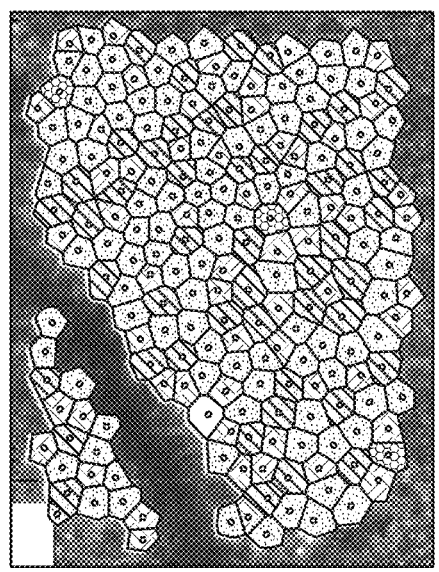
Figure 6B:
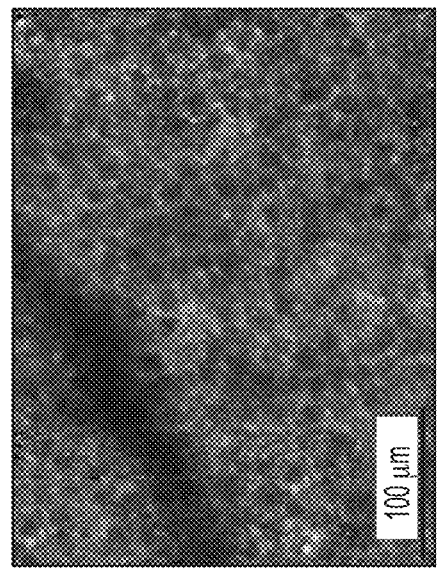

Voronoi analysis was applied to the RPE images to determine packing properties of the RPE cell mosaic. To illustrate, FIGS. 6A-D shows the cone and RPE cell mosaics from the same averaged, registered AO-OCT volume acquired 3° temporal to fovea of Subject 5. The photoreceptor and RPE cell mosaics are shown in FIGS. 6A-B, respectively. As evident in the figure, the RPE cell mosaic is more coarsely tiled than the cone mosaic of the same retinal patch. For analysis, cell locations of each cell type were identified as depicted in FIGS. 6C-D. Differences in density and area of the two cell types are evident when cell centers of the two are superimposed (FIG. 6E). Using cone centers and Voronoi mapping of the RPE mosaic, the average number of cones per RPE cell for this retinal patch is 4.0:1. Superposition of the 2D power spectra of the two layers demonstrates a clear difference in fundamental frequency denoted by the two rings of concentrated power (FIG. 6F). Corresponding row-to-row spacing is 7.2 and 14.4 µm for cones and RPE cells, respectively, confirming the spatially coarser tiling of the RPE cells.

Figure 7:
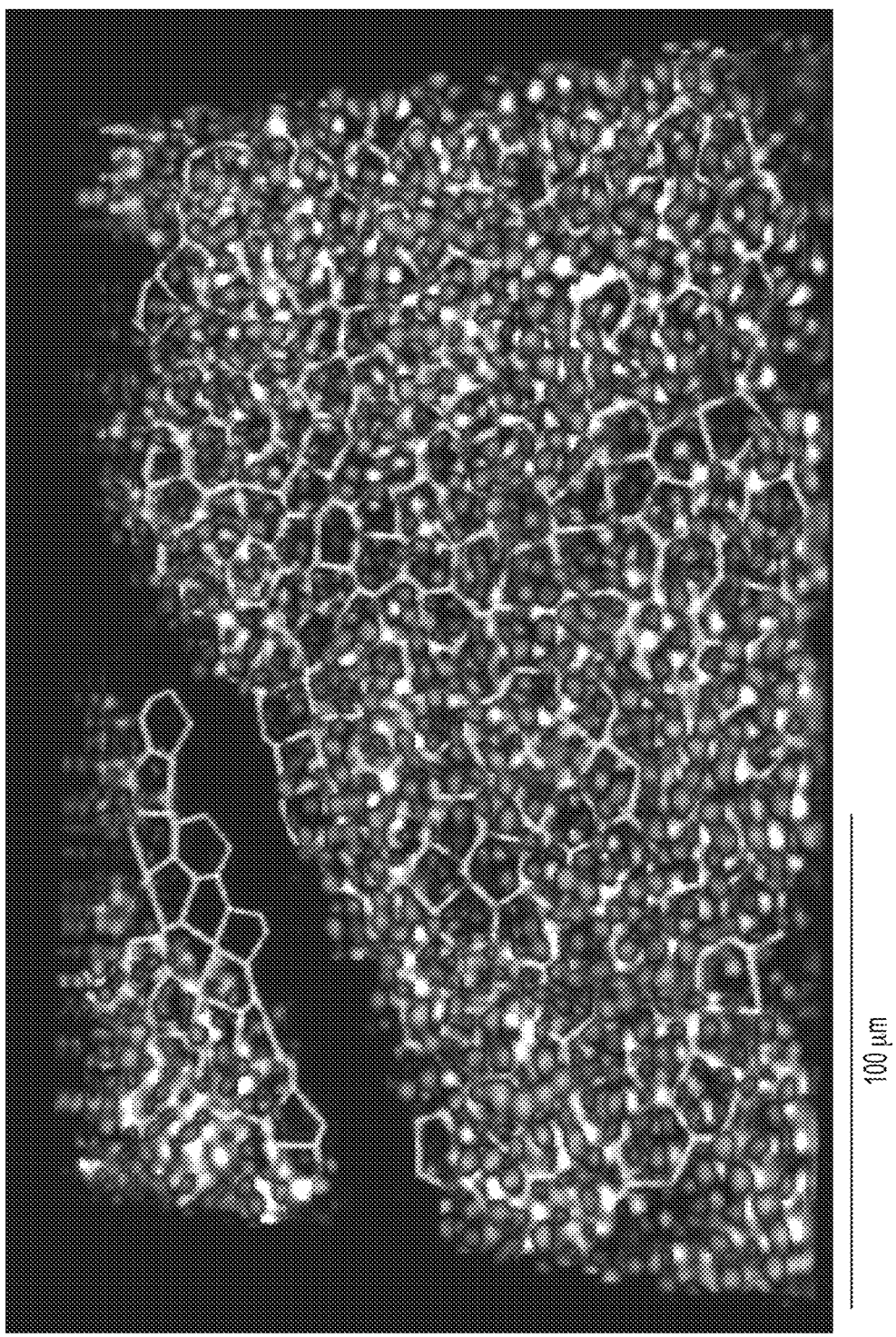
FIG. 7 provides an adaptive optics OCT volumetric reconstruction of the photoreceptor-RPE complex of a subject at 3° temporal to fovea.

As illustrated by the constructed 3D view in FIG. 7, simultaneous imaging of the RPE and cone layers by AO-OCT enables volume rending with true one-to-one mapping of cellular structures at different depths. In this case the Voronoi map is superimposed at the depth of RPE and enables the number of cones per RPE cell to be computed.

Because of potential subjectivity in the Voronoi analysis due to the manual selection of RPE cell centers, agreement between two trained technicians who independently mapped RPE centers in all six subjects and two retinal locations was tested. Of these 12 datasets, one (S3, 7°) outlier was found that yielded a difference in measured density of 29% between technicians and fell outside the 95% confidence range of a Bland-Altman test. Average absolute difference between the other 11 was 3.4% in terms of cell density and 1.8% when converted to cell spacing assuming triangular packing. Based on this test and the observation that RPE cells in the (S3, 7°) image were notably less clear than in the others, this image was excluded from the Voronoi analysis. Note that while manual cell identification was determined unreliable for this image, its power spectrum still yielded a ring of energy at the expected RPE frequency (see FIGS. 3 and 4).

Figure 8A:
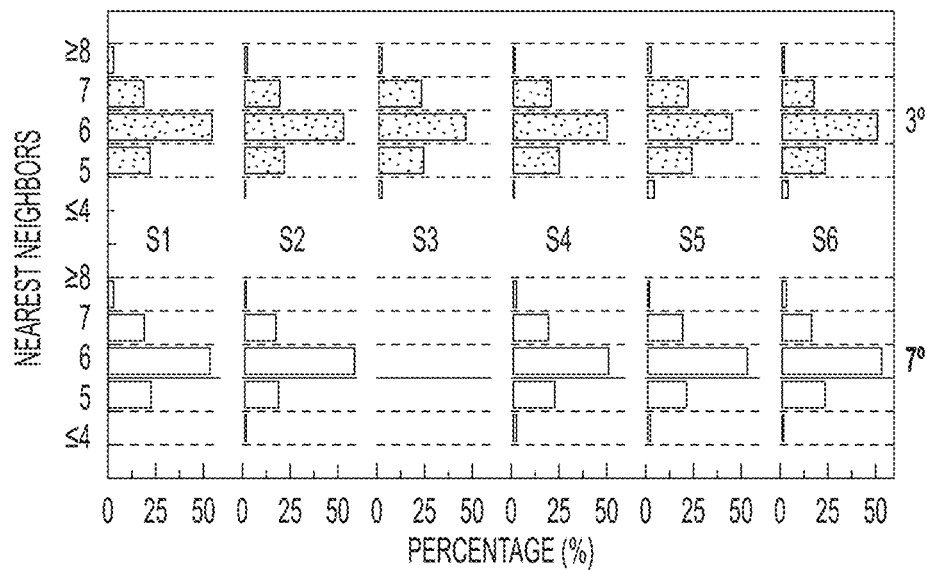
FIGS. 8A-B provides graphs, as a function of subject age, of the prevalence of nearest neighbors of RPE cells across subjects and retinal eccentricities and mean and mean standard deviation of Voronoi side lengths.
Figure 8B:
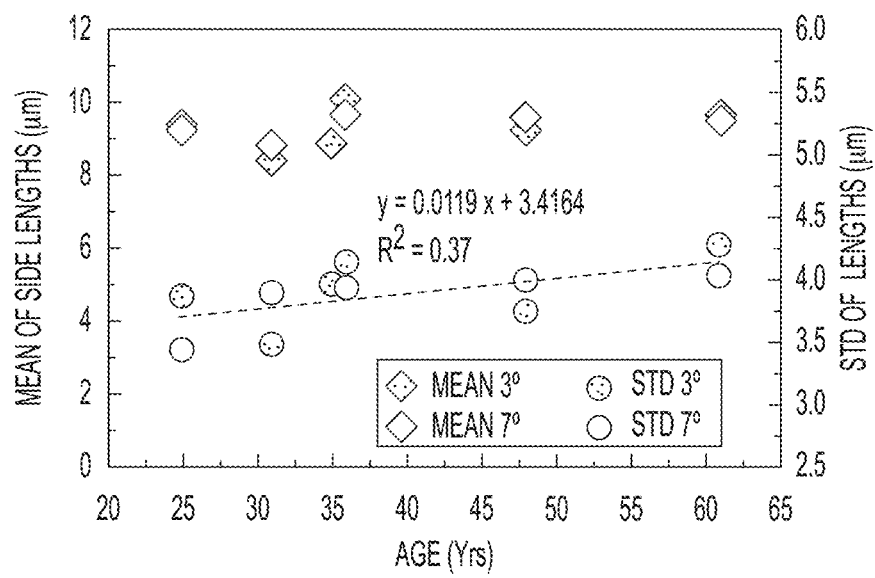
Figure 9:
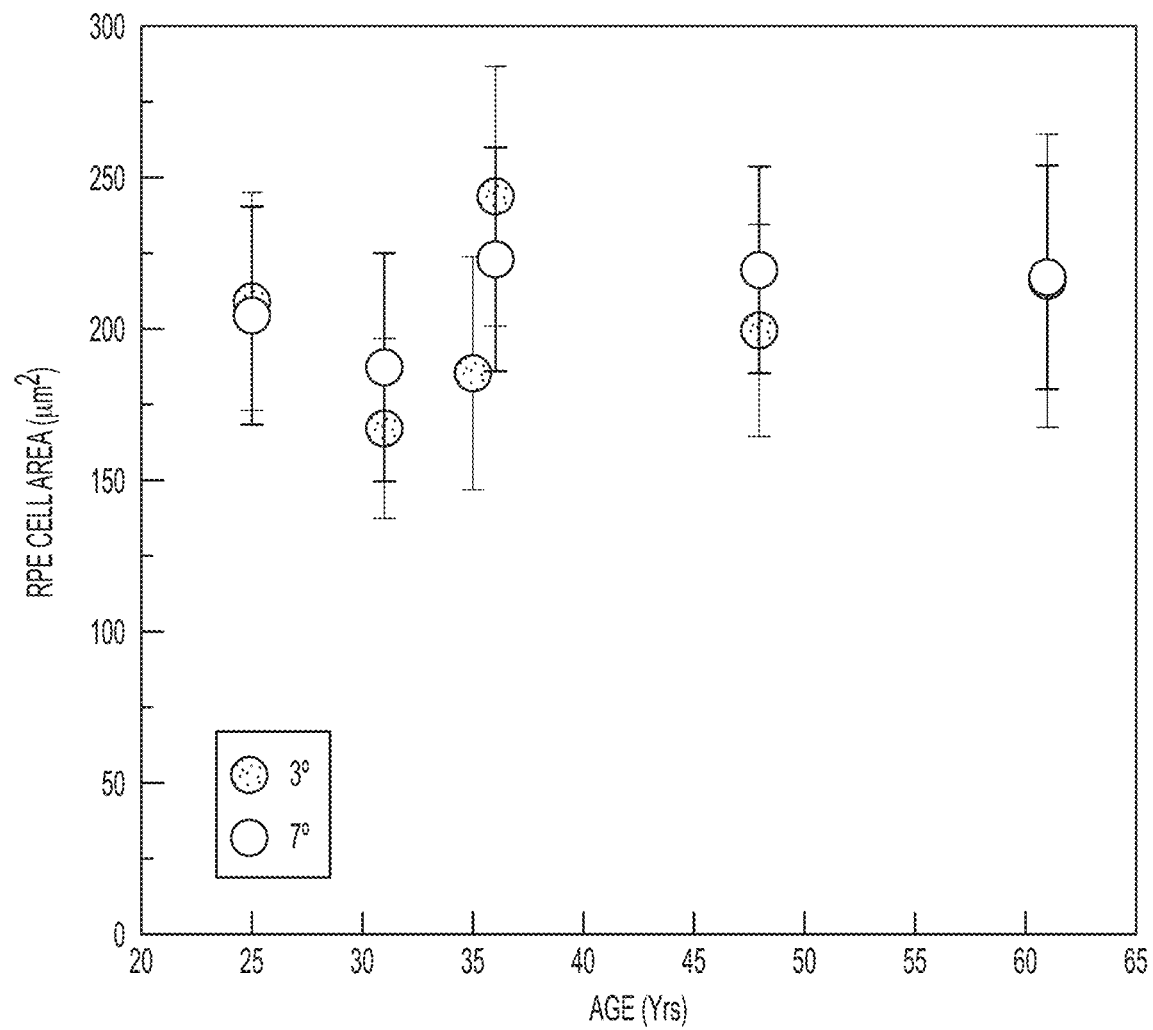
FIG. 9 is a plot of average RPE cell area at 3° (black) and 7° (gray) temporal to the fovea in six subjects.
Figure 10:
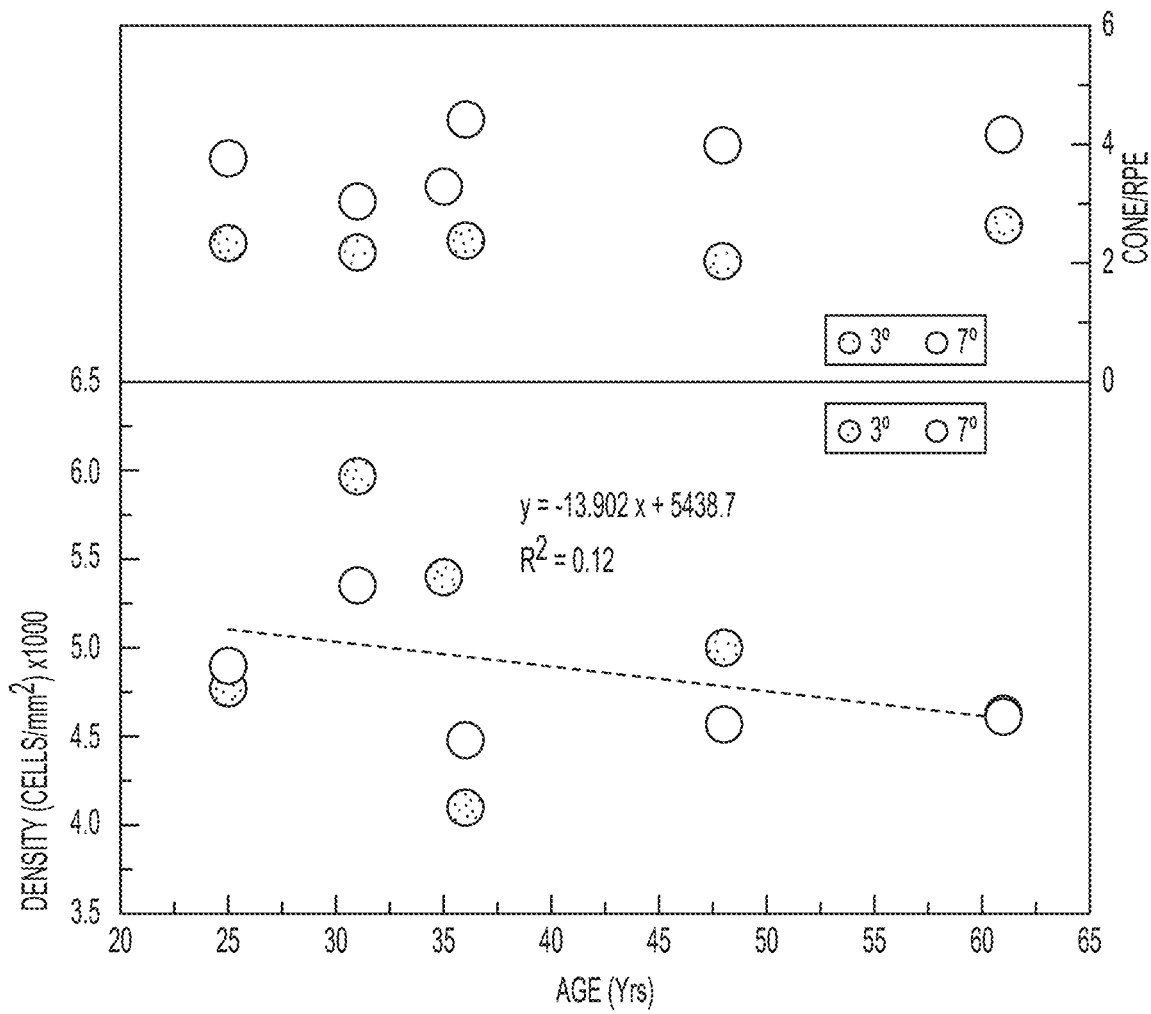
FIG. 10 is a plot of retinal pigment epithelial cell density and cone-to-RPE ratio as a function of subject and retinal eccentricity.

Results of the Voronoi analysis are summarized in FIGS. 8-10, which show RPE number of nearest neighbors, Voronoi side length, cell area, cell density, and cone-to-RPE ratio for the six subjects and two retinal eccentricities imaged. Analysis is based on a total of 2997 RPE cells.

Discussion

3D Reflectance Profile of Photoreceptor-RPE Complex

The AO-OCT study revealed that the RPE band observed in conventional OCT is actually composed of two distinct, but faint bands. Both bands were visible regardless of age and separated in depth by approximately 10 µm (see FIG. 1A). Other AO-OCT and OCT studies also have reported two subbands in the RPE layer and appear to correspond to ROST and RPE in this study. However, unlike these other studies, in the present study the double band was observed in every subject (6 subjects) and retinal location (3° and 7° in the six subjects and 2° to 10° in one subject) imaged, except near the foveal center, that is, 0.6°. This suggested that the double band is likely present across much of the retina, further supported by the fact that the band appears to depend on fundamental properties of rods and RPE cells as is further discussed below.

It should be noted that in the younger eyes an additional more posterior band also is apparent, thus, making the double band actually a triple band, as for example in FIG. 1A, which shows a faint band immediately below that labeled RPE. In older subjects, this additional band is not evident, for example in FIG. 5B. While not being limited to any particular theory, the additional band may be attributable to Bruch's membrane.

Figure 11:
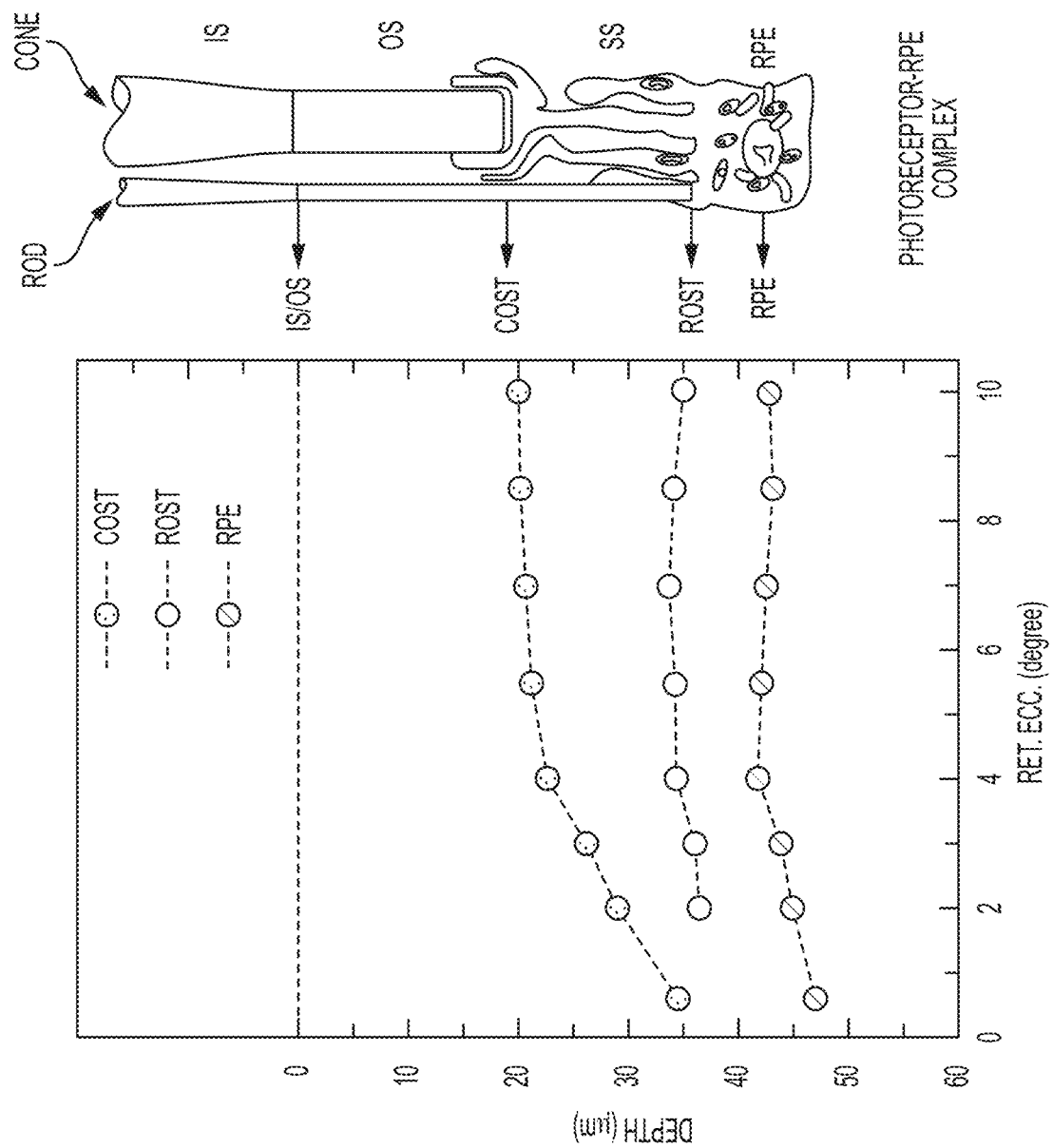
FIG. 11 depicts axial displacement of COST, ROST and RPE from IS/OS as a function of retinal eccentricity.

The best characterization of the depth profile of the dual band is with the AO-OCT measurements in FIGS. 5A-C and 11, obtained on Subject S5 from 0.6° to 10° retinal eccentricity. These measurements reveal not only the variation in the ROST peak with retinal eccentricity, but also the peak's axial separation from other prominent reflections in the photoreceptor-RPE complex, namely IS/OS, COST, and RPE. As shown in FIG. 11, the ROST-to-IS/OS separation (defined as the rod OS length) is relatively constant across retinal eccentricities, on average 34.81+/−0.99 µm, which is consistent with the histologic value of 32 µm summarized by Spaide and Curcio in Spaide R F, Curcio C A, *Anatomical correlates to the bands seen in the outer retina by optical coherence tomography literature review and model*, Retina-J Ret Vit Dis. 2011; 31:1609-1619, the entire content of which being expressly incorporated herein by reference, but shorter than the 40 to 45 µm reported near the optic disc using ultrahigh-resolution OCT. In contrast, the COST-to-IS/OS separation decreases from 29.07 to 20.07 µm over the same retinal eccentricity range, a 31% reduction and consistent with histology. The subcellular space (SS) between ROST and COST increases from 7.27 µm at 28° to 14.71 µm at 10°, while the separation between ROST and RPE remains relatively constant at 8.11+/−0.58 µm regardless of retinal location. Across all six subjects, the separation between ROST and RPE was 8.93 6 1.00 µm. This separation does not necessarily correspond to actual RPE thickness, but is consistent with histologic values of thickness reported in the macula (10.3+/−2.8 µm).

Closer examination of the double band (ROST and RPE) reveals that neither is a true band that exhibits uniform reflectance, but instead consists of spatially distinct mosaics of different grain. The ROST mosaic is characterized by darkened punctate reflections in a bright surround, with the darkened spots lying under cones, thus, appearing as cone (pseudo-) shadows. This arrangement was observed in all subjects examined, though varied with retinal eccentricity. While not apparent in the averaged images, numerous single images and, in particular, those acquired in S5 using finer A-scan sampling of 0.6 µm/px (see FIG. 5C), revealed the bright surround was pixeled with many punctate reflections (darker regions) that the present system could only partially individuate, a size suggestive of rod photoreceptors. This observation of rod structure is consistent with earlier AO-OCT reports of rod-like reflections at this retinal depth. A reflection at this depth is also consistent with where rod outer segments abut the RPE cell bodies based on histology.

As further evidence of a ROST attribution, the punctate reflections become increasingly more prevalent with increased retinal eccentricity as shown by the increase in darker regions in FIG. 5C. Note that traces of the darker regions—albeit small—appear at 0.6°, which lies within the rod-free zone. This is likely not attributable to rods, but rather the inability of the present method to separate COST from the apical portion of the RPE due to their increasingly close proximity in the foveal region. Prevalence of ROST also can be assessed by its reflectance in cross-section, as for example in the averaged B-scan and A-scan profiles of FIG. 5B. As evident in the A-scan traces 15, the ROST reflectance peak increases monotonically with retinal eccentricity starting with no evidence of a ROST peak at 0.6° and a substantive one at 10°, resulting in the second strongest peak in the entire A-scan profile. This trend is consistent with what is known of rod density, absent near the fovea and increasing outward with a maximum density at 15° to 20° retinal eccentricity.

In general the findings of the present disclosure suggested that ROST is a superposition of two mosaics, a coarse one created by cone (pseudo-) shadows and a much finer one created by rod OS tip reflections.

The RPE mosaic also consisted of darkened spots in an elevated surround, but of coarser grain and no apparent relation to the cone mosaic. This finding should not be unexpected given the basal location of the RPE cell nuclei and match of the darkened spot spacing to that of RPE cells (see cell density comparison below). The darkened spots likely correspond to the cell nuclei since their low refractive index (n~1.4) relative to surrounding organelles (e.g., melanin at n~1.7) and their large size (>>λ) results in highly anisotropic scatter (strong forward scatter and weak back scatter). In addition, size of the darkened spots compared favorably to that reported with other in vivo imaging modalities and with histology. It should be noted that an alternative explanation is that the darkened spots are generated by clusters of melanin granules—rather than RPE nuclei—which apically shield the nuclei from light exposure. This explanation seems plausible at visible wavelengths where melanin absorbs strongly, but at the near infrared wavelengths of our AO-OCT, melanin absorption is at least seven times less.

The elevated reflection that surrounds the darkened spots most likely originates from scatter of organelles in the cytoplasm, the predominate ones being melanin and lipofuscin granules. Of these, melanin is known to be a strong scatterer owing in part to its high refractive index (n~1.7). In addition, growing evidence points to melanin as the source of the strong OCT signal in the RPE layer. This makes melanin the likely source of the elevated surround in the images of the present disclosure. Consistent with this expectation is the higher SNR we measured for RPE cells at 3° compared to at 7° (see FIG. 12 and accompanying discussion). Because of the inverse concentration of melanin and lipofuscin with retinal eccentricity, the opposite would be expected, that is, higher contrast at 7°, had lipofuscin been the key scatterer. A further test would have been to analyze reflectance of the cytoplasm as a function of depth in the RPE cell as melanin and lipofuscin also are nonuniformly distributed in this dimension. However, the ROST reflection in the apical half was too strong and masked contributions of organelles there. Based on this collection of evidence, the mosaic observed in the RPE band may be interpreted to be the RPE cell mosaic.

Organelle Motility and Volume Averaging

Volumes acquired over 90 minutes at 3-minute intervals generated different noise patterns across the RPE image, suggesting this time interval was long enough for sufficient organelle (e.g., melanin) motility to occur. Averaging these volumes reduced the prevalence of noise and increased the RPE cell signal, which increased clarity of the RPE mosaic. In contrast, little improvement in RPE cell clarity was observed when volumes acquired over seconds (<6 seconds) were averaged, as opposed to minutes. While it remains to be determined what the optimal timing acquisition parameters should be, insight may be gained into the benefit that accrues from averaging. To do so, SNR was systematically computed for the RPE mosaic as a function of number of images averaged across subjects and retinal eccentricities.

Figure 12:
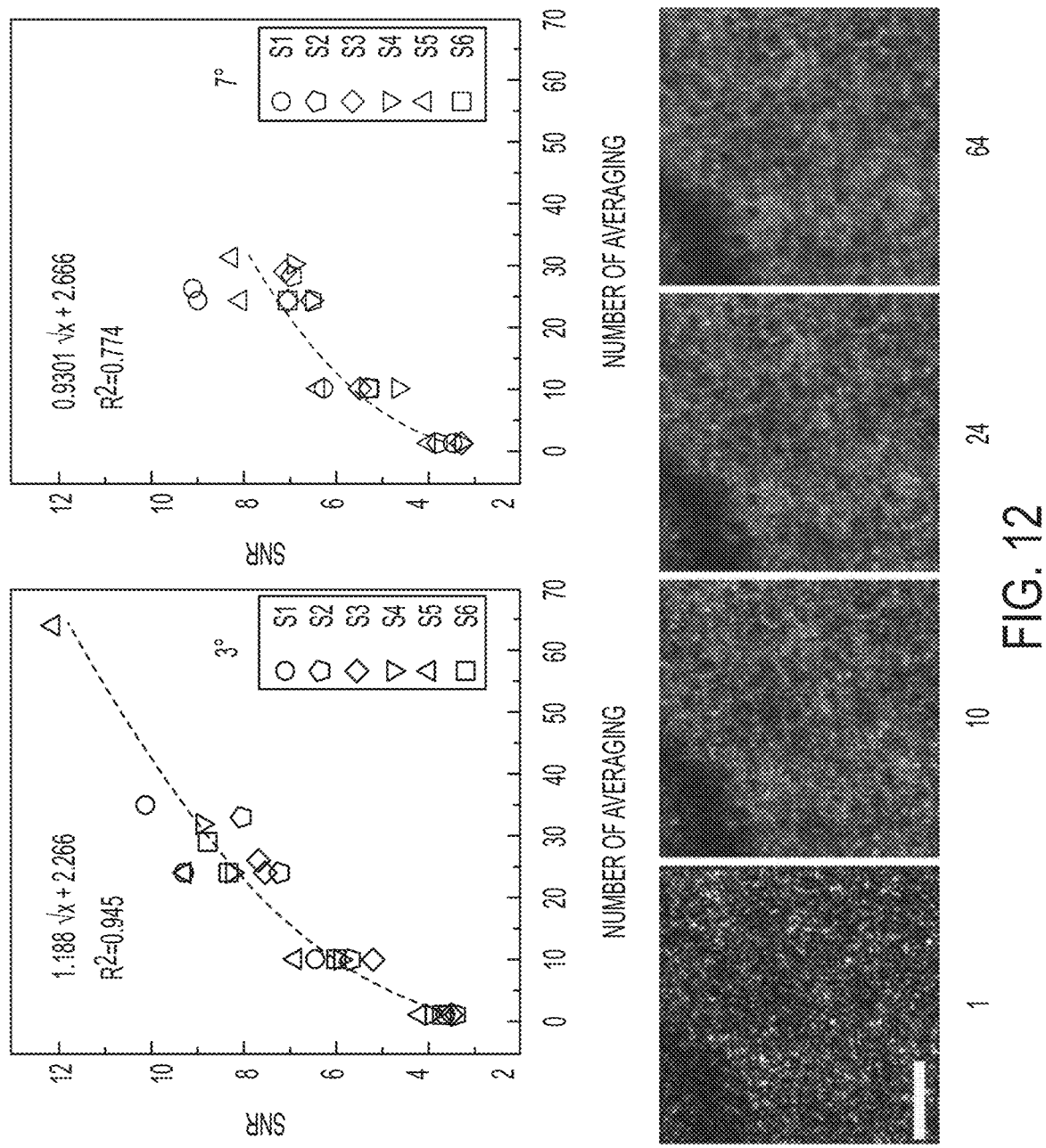
FIG. 12 provides signal-to-noise ratio of RPE fundamental frequency at 3° and 7° retinal eccentricity as a function of AO-OCT images averaged, and representative RPE images of a retinal patch for a subject with different levels of averaging.

FIG. 12 plots the results of the SNR analysis along with representative RPE images of different averaging. As evident in the plot, SNR improves proportional to the square root of images averaged, expected if the noise patterns are independent. More images always resulted in higher SNR, indicating that images were registered with an accuracy better than the size of RPE cells. In fact, averaging over two 90-minute sessions (S5, 3°) provided the highest SNR. Visual inspection of the averaged images found those with the best RPE mosaic clarity had the highest SNR. The results indicate that even more averaging will benefit RPE cell clarity, but this comes at the expense of longer image acquisition, which imposes a practical limit.

In this study, the time required to perform the experiment and process the images was not optimized, an important consideration for assessing clinical utility. Data collection was over 90 minutes followed by several hours of postprocessing and data mining of the images. This total time can likely be decreased substantially as described herein. In fact, it was shown that the same number of images can be captured in one-third the time, that is, 30 instead of 90 minutes, without loss in RPE cell clarity, and even shorter times appear possible. As for postprocessing, no fundamental limit is seen that prevents reducing the principle steps of image registration, RPE cell identification, and Voronoi and spectral analysis using more powerful data processing tools, such as parallel computing. Also, while some of the steps already are automated (e.g., Voronoi and spectral analyses), others are not, in particular RPE cell identification, which was done manually. Automating identification would lead to further reductions in time.

RPE Mosaic Characterization Using Voronoi and Power Spectra Analyses

Figure 13:
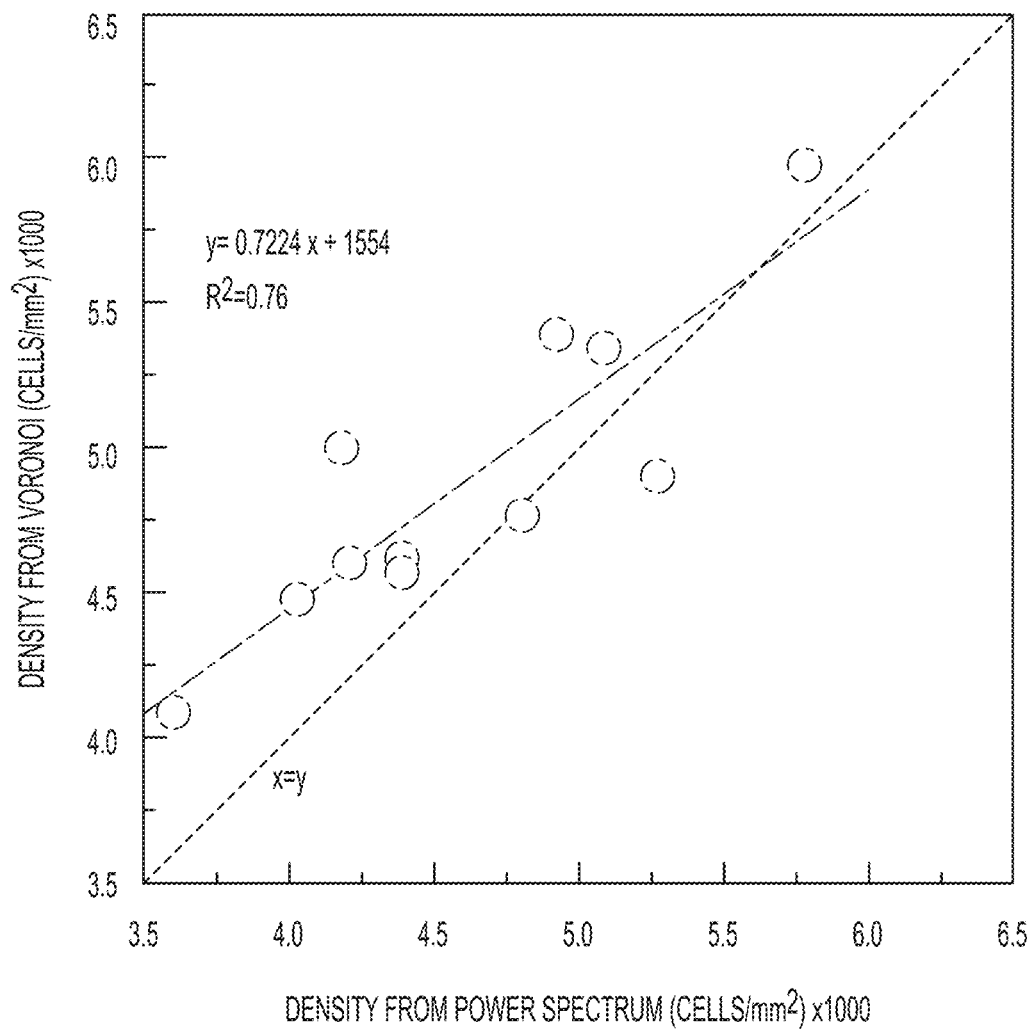
FIG. 13 is a graph of correlation of RPE cell density determined from Voronoi and power spectrum analysis.

Cell density measurements from power spectra and Voronoi are sensitive to different properties of the mosaic regularity. The former is sensitive to the dominant cell packing frequency and the latter to local variations in the frequency and irregularities at the cell level. To determine the extent to which these differences manifest themselves for density measurements of the RPE mosaic, their correlation was tested on the same images. Results are shown in FIG. 13 and reveal an $R^2$ of 0.76. Average absolute difference between measurement points in the figure is 9.4% of the average cell density, corresponding to a difference in row-to-row cell spacing of 0.64 μm assuming triangular packing. While this average difference is relatively small, individual differences from the same RPE image are notable in the plot and do not appear systematic. In general Voronoi estimates a higher density than power spectra, perhaps because local irregularities in the mosaic are of generally finer fidelity.

Comparison to Other RPE Studies

It is difficult to compare the present RPE density measurements to other studies owing to differences between subjects, retinal locations, and age, but a few notable comparisons are made here. To facilitate, density measurements from the Voronoi analysis were used instead of power spectra as the former better aligns to the methods used in the literature, some of which were based on Voronoi. From the Voronoi analysis, average RPE cell density for the six subjects at 3° and 7° temporal retinal eccentricity (FIG. 10) was 4975+/−651 cells/mm$^2$ and 4780+/−354 cells/mm$^2$, respectively. Two in vivo imaging studies used autofluorescence AO-SLO and dark-field AO-SLO to image RPE cells in normal, relatively young subjects. For autofluorescence AO-SLO, three subjects (25-30 years) were imaged along the superior vertical meridian starting at 5°, 6.25°, and 15° from fixation. Retinal pigment epithelium density at the most relevant locations of 5°, 6.25°, and 7.5° in two subjects ranged from 5090 to 5970 cells/mm$^2$ with an average of 5645 cells/mm$^2$, which is elevated compared to the 4780+/−354 cells/mm$^2$ measured at 7° in the present study. Analysis of the same AO-OCT volumes, but at the photoreceptor layer yielded cone density measurements of 11,032+/−1174 cells/mm$^2$ that is consistent with histology and in vivo cone packing studies. This suggests the source of the RPE difference is unlikely to be caused by an error in the present AO-OCT system, image acquisition, or common data processing steps for RPE and cone cells. For dark-field AO-SLO, seven subjects (19-40 years) were imaged at the foveal center and 10° temporal to fixation with measurements limited to NND. While the present 3° measurements were too distant to compare to foveal densities, the present average NND at 7° was 12.2+/−1.6 μm compared to 13.4+/−0.6 μm at 10° by Scoles et al. (Scoles D, Sulai Y N, Dubra A, *In vivo dark-field imaging of the retinal pigment epithelium cell mosaic*, Biomed Opt Express. 2013; 4:1710-1723). The difference between these two is not statistically significant (P>0.05).

From histology considerable variation has been reported. In a study by Panda-Jonas et al. RPE density was measured in 53 eyes confined to annuli concentric to the fovea. In the first annulus (2-5 mm, or approximately 6.7°-16.7°) density along the temporal meridian was 3392+/−528 cells/mm$^2$. While average age (58.6 years) was higher than in the present study (39.3 years), accounting for the 0.3% decrease per year as observed by Panda-Jona et al. decreases the present 7° measurements to 4503 cells/mm$^2$, which is still 33% higher. However, another study by Watzke et al. reported RPE density in 20 normal eyes, 10 below the age of 50 years for two retinal locations that straddle our 3° and 7° measurements. They report 5893+/−809 cells/mm$^2$ within 250 μm of fovea (<18) and 4834+/−764 cells/mm$^2$ at 4 mm (~13.3°) temporal to the fovea. The present density measurements are consistent with this range. Finally, in the most recent study, Ach et al. measured RPE density in 20 normal eyes, 10 at or below age of 51 years. For these 10, average RPE density across the perifovea (~2°-10°) was 5091+/−823 cells/mm$^2$, which is statistically not significant from the present 3° and 7° measurements. In general, there is a large variation in RPE densities reported from in vivo and histology studies, including in the present study. This variation points to the importance of in vivo measurements that can track individual differences over time and to detect those cellular changes associated with disease, as for example with AMD.

The present density measurements were spaced relatively close (3° and 7°) and, thus, did not lend themselves to test for a retinal eccentricity dependence. Indeed, no statistical significance was found with Voronoi (paired t-test, P=0.58) nor power spectra (paired t-test, P=0.92) measurements. The present study also tested for an age dependence across the age range examined: 25 to 61 years. The regression line in FIG. 10 shows a decrease in density with age, but this was not statistically significant (P=0.30). No statistical significance also was found for the corresponding power spectra measurements, but the P value was lower (P=0.11) and the 95% confidence interval for the regression slope was −56.3 to 7.09 cells/mm$^2$/y. While the present study used a small sample size, it nonetheless demonstrated that RPE packing now is measurable in younger and older eyes and establishes a clear path for testing aging effects in a larger population. Such tests have not been conducted in vivo (regardless of imaging modality) and may shed important insight into the aging controversy reported with histologic studies. These studies have reported densities showing no change with age, a decrease with age, or different aging effects depending on retinal location.

Finally, the present study examined RPE cell regularity. From Voronoi analysis (FIGS. 8A-B), the most prevalent number of nearest neighbors regardless of subject and retinal eccentricity was six. Prevalence for six neighbors was 50.49+/−3.66% at 3° (843 of 1659 cells) and 54.58+/−3.01% at 7° (733 of 1338 cells), both consistent with histology in humans (49.63+/−8.74% for <=51 years group). Prevalence of six neighbors was significantly larger than the next two most prevalent associations: five (P<0.05, t-test) and seven (P<0.05, t-test). By grouping the three youngest (average=30.3 years) and three oldest (average=48.3 years) subjects, prevalence of six nearest neighbors decreased from 52.8% to 51.2% with age. This corresponds to a decrease of approximately 124 RPE cells with six nearest neighbors. This suggestive decrease in cell regularity with age is consistent with the findings of Ach et al. using the same Voronoi metric, but a larger sample size is required to test. Other Voronoi metrics may be more sensitive to packing regularity. For example, the mean standard deviation of the Voronoi side lengths (FIG. 8B) indicates a gradual increase with age (P=0.05), which points to a decrease in cell regularity.

Cone-To-RPE Ratio

The AO-OCT method of the present disclosure captures volume images of the retina and, thus, other layers can be extracted from the same volume, enabling a direct spatial comparison on a cell by cell basis. FIGS. 6A-F illustrates this for the spatial arrangement of cone photoreceptors relative to the underlying RPE cells of one subject and FIG. 10 quantifies the ratio of these two cell types for all six subjects and two retinal eccentricities. Unlike RPE cell density, which showed no significant difference between 3° and 7°, cone-to-RPE ratio did. The ratio was significantly lower at 7° (2.31+/−0.23:1) than at 3° (3.78+/−0.53:1; P<0.05), a factor of 1.6 decrease. This decrease originates from the reduced cone density at the larger retinal eccentricity. For the six subjects of the present study, average cone density decreased by a factor of 1.64, close to the 1.6 decrease in cone-to-RPE ratio.

There is limited histologic human data in the literature to compare to the present ratio measurements. One study reported ratios of 24.09:1 at the fovea and 0.89:1 at the equator. The present 3° and 7° ratios fall within this range. Another study reported an average cone-to-RPE ratio of 1.10+/−0.24 across the temporal meridian from approximately 6.7° to 16.7°. The present 7° ratio is a factor of two higher, a portion of which was attributable to the decrease in cone density with retina eccentricity.

In Vivo Imaging of Human Retinal Ganglion Cells with AO-OCT

Referring now to FIGS. 14-39, in another study, four healthy subjects (ages: 24-50 years) were imaged at five macular locations (1.5° to 3°, 3° to 4.5°, 6° to 7.5°, 8° to 9.5°, and 12° to 13.5°) temporal to the fovea using the AO-OCT system described herein. Corresponding nasal locations were also imaged for one of the subjects. For each retinal location, 1.5°×1.5° field-of-view AO-OCT videos were acquired with system focus at the RGC layer. Volumes were registered in three dimensions with subcellular accuracy and averaged to increase image contrast of RGC somas. In post processing, spatial coordinates of RGC soma centers were identified and marked manually using custom software. Soma coordinates were used to determine soma stack depth, density, and diameter. Voronoi analysis was used for RGC density measurement with exclusion of blood vessels.

Figure 14:
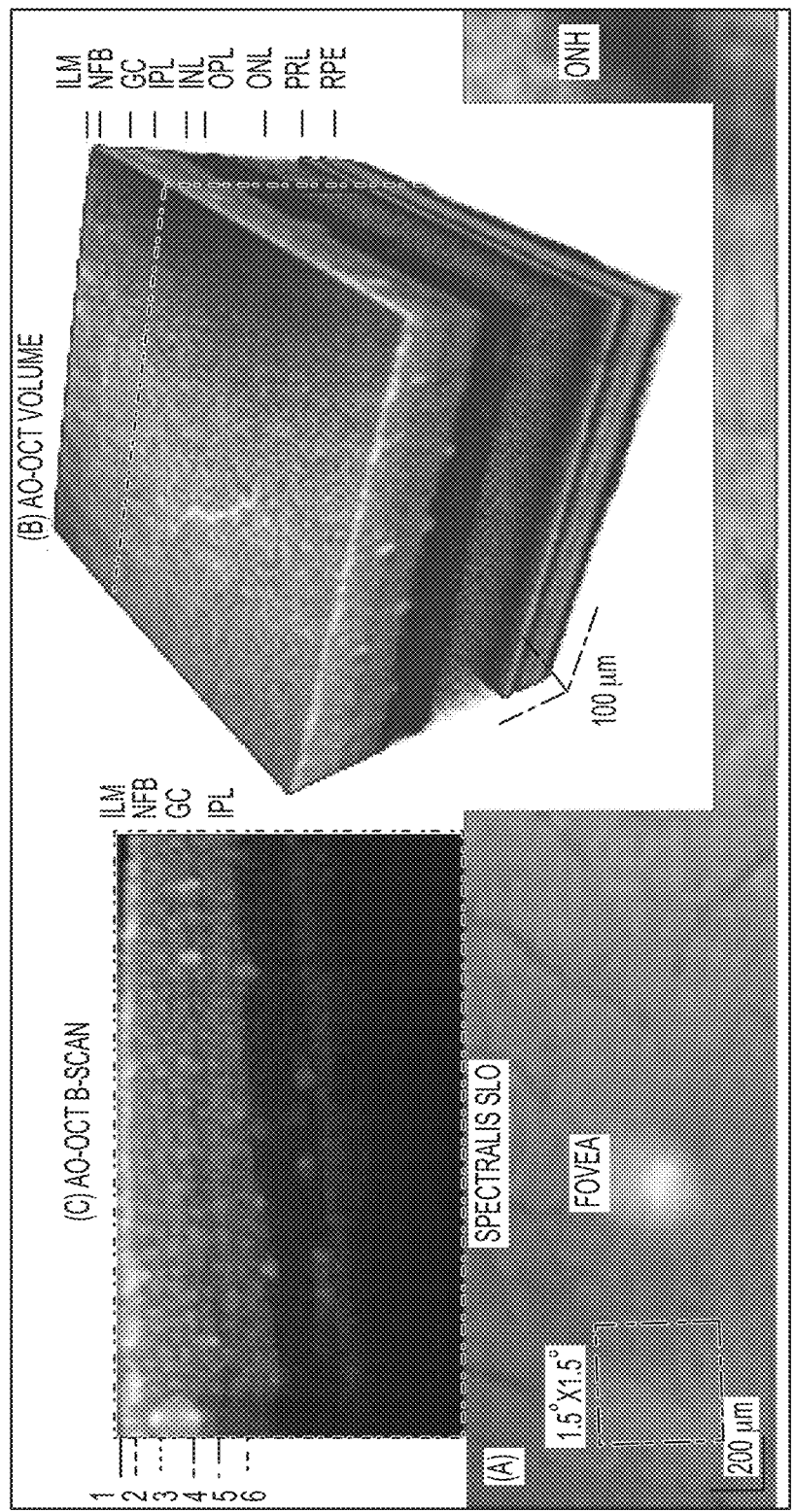
FIG. 14 depicts an AO-OCT retinal volume image.
Figure 15:
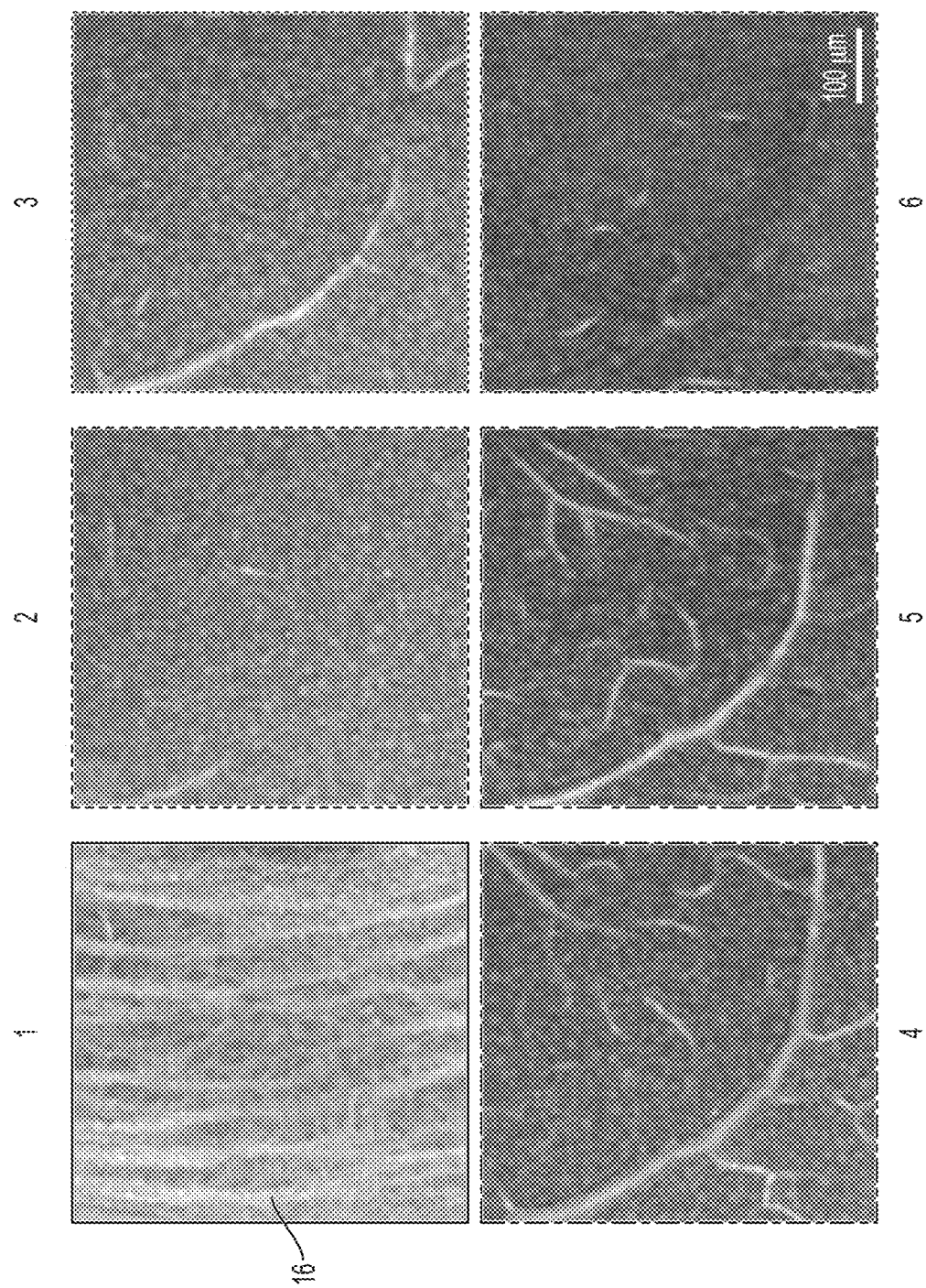
FIG. 15 provides en face cross sections of the volume image of FIG. 14.

A 3D mosaic of RGC somas was observed in every subject and retinal eccentricity imaged at a total of 25 locations. FIG. 14 depicts an AO-OCT volume image of a 450×450 µm² patch of retina collected at 1.5°-3° temporal to the fovea. FIG. 15 depicts en face cross sections at increasing depth in the retinal nerve fiber and ganglion cell layers of the AO-OCT volume image of FIG. 14. The bright vertical striations 16 in the top-left image are individual retinal nerve fiber bundles that reside near the retinal surface. Cross sections beneath the RNFL reveal a mosaic of faint bright spots that we were as retinal ganglion cell soma.

Figure 16:
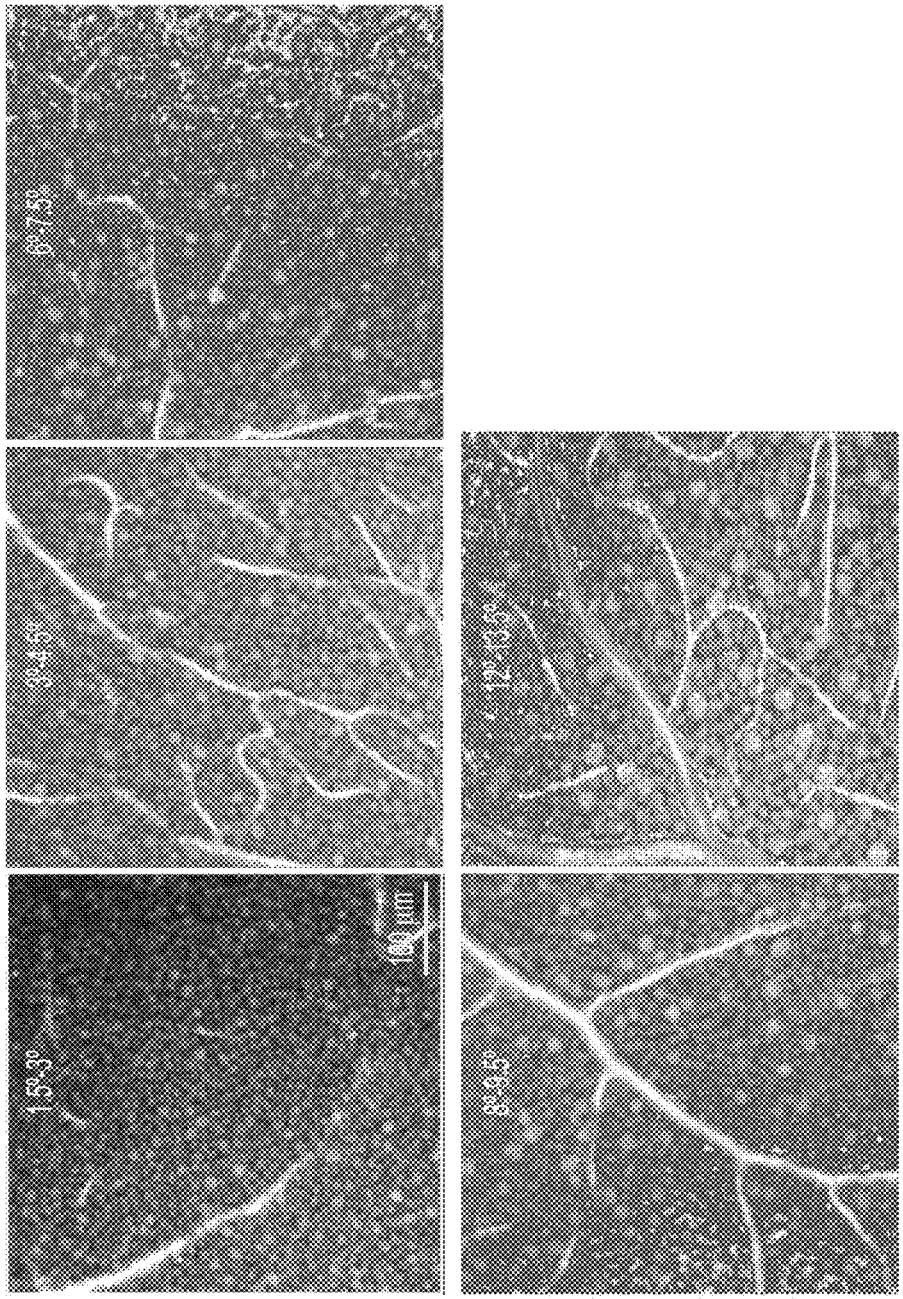
FIG. 16 provides en face cross sectional images of the retinal ganglion cell layer at increasing retinal eccentricity.
Figure 17:
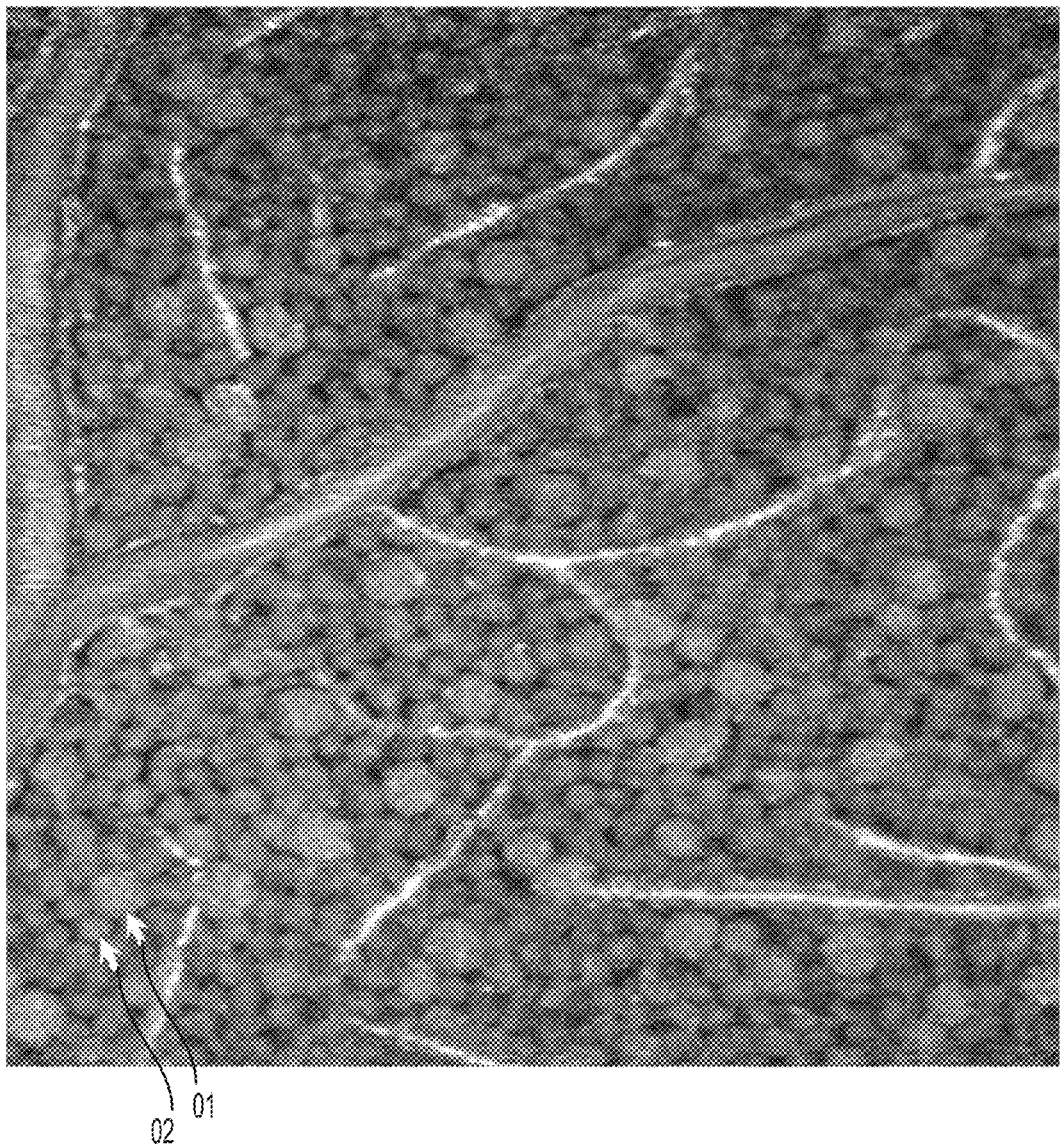
FIG. 17 is an enlarged view of the en face image of FIG. 16 at 12°-13.5°.
Figure 18:
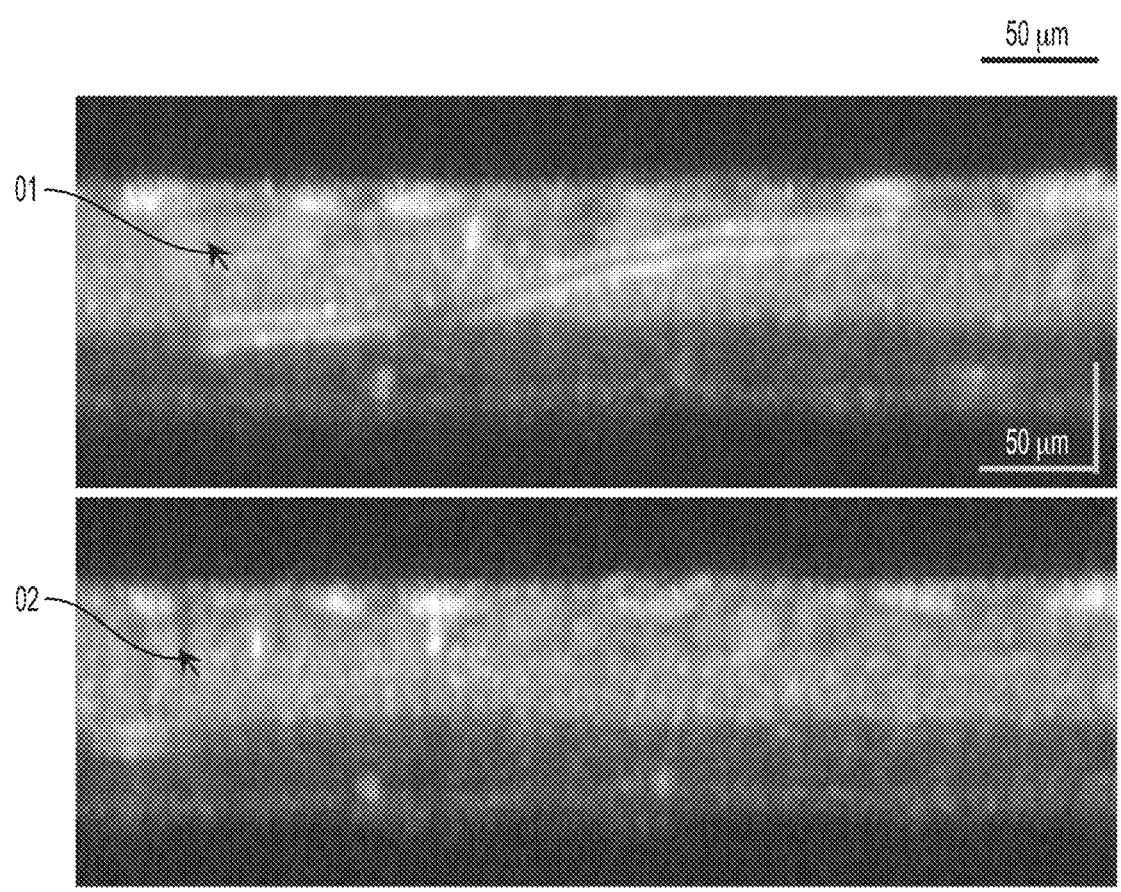
FIG. 18 provides depth cross sections of the image of FIG. 17 at two different orthogonal intersections.
Figure 30:
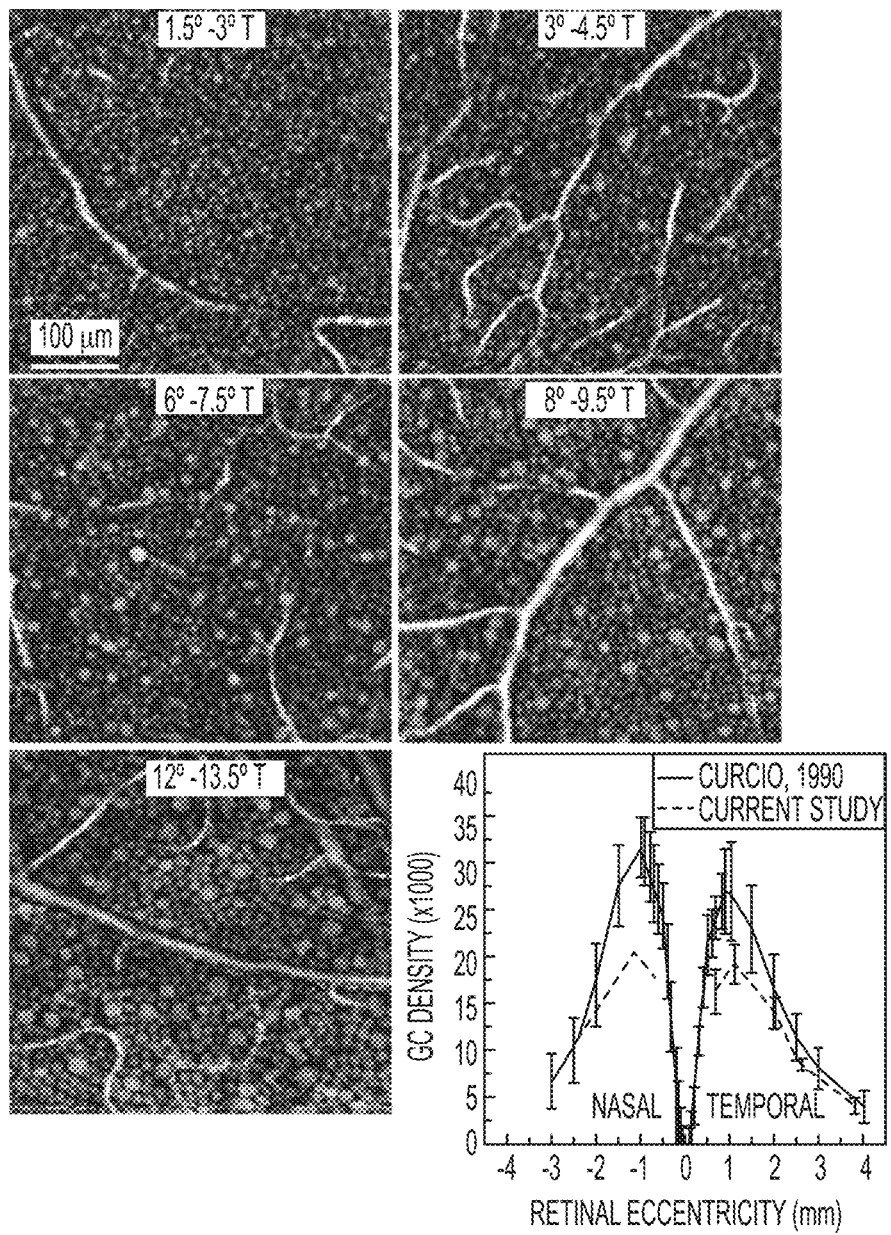
FIG. 30 provides images from a GCL at different retinal eccentricities and a plot of GCL soma density.

Referring now to FIG. 16, en face cross sectional images of the retinal ganglion cell layer are shown at increasing retinal eccentricity. A mosaic of retinal ganglion soma (faint bright spots) is observed at every location. As evident in the images, soma size and distribution increase with retinal eccentricity. The greater reflectivity of the larger soma should be noted, which is more apparent at the larger retinal eccentricities. The graph at the bottom right of FIG. 30 shows measured retinal ganglion soma density plotted as a function of retinal eccentricity in two subjects. FIG. 17 provides an enlarged view of the en face image at 12°-13.5° of FIG. 16. This enlarged view reveals the notable difference in size between small (Arrow 02) and large (Arrow 01) ganglion cell soma. FIG. 18 provides depth cross sections of the inner retina at two different orthogonal intersections of the FIG. 17 en face image. Arrow 01 and Arrow 02 denote the same cells as in FIG. 17.

Figure 19:
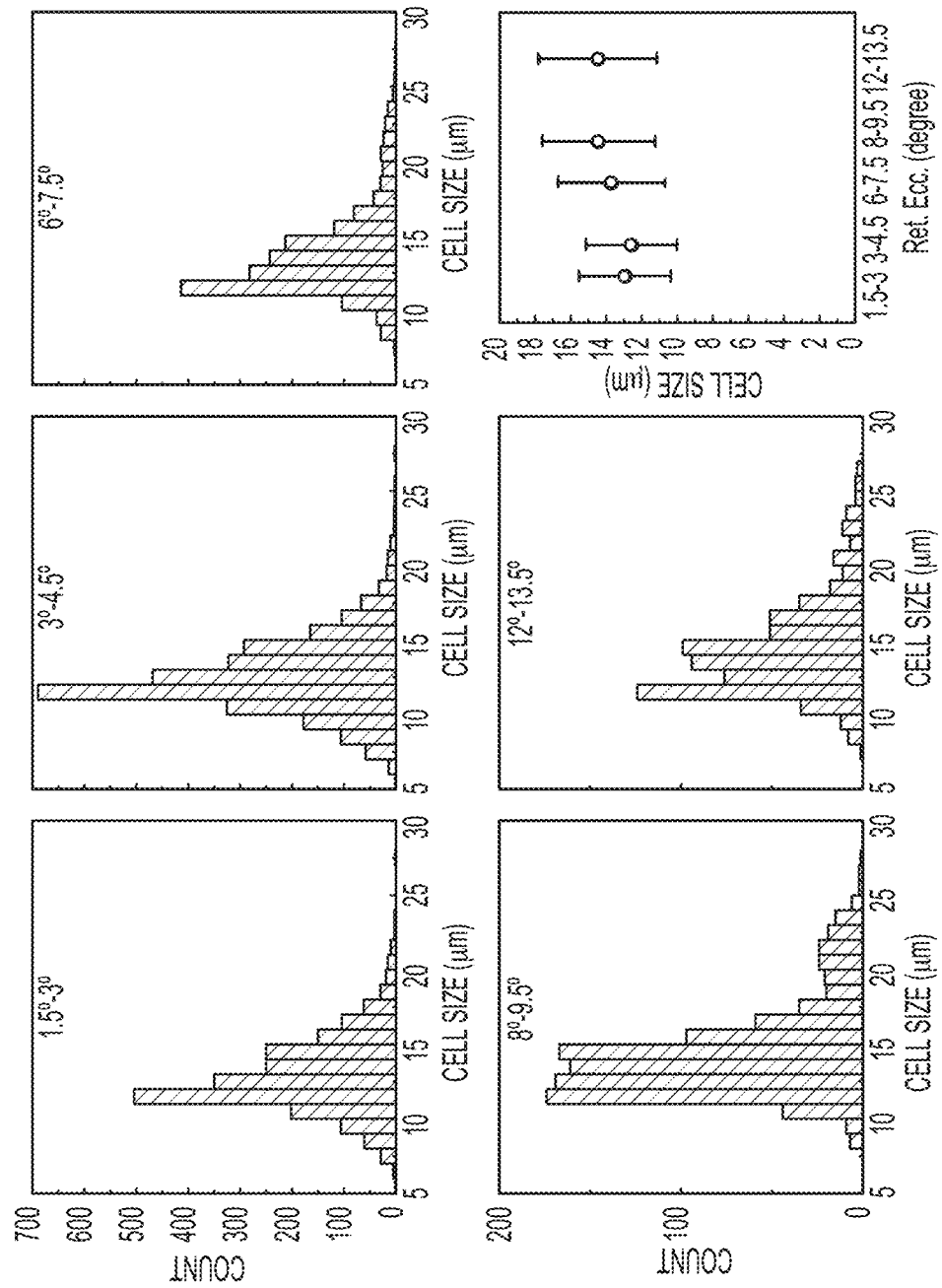
FIG. 19 provides graphs of soma diameter distributions as a function of retinal eccentricity.
Figure 20:
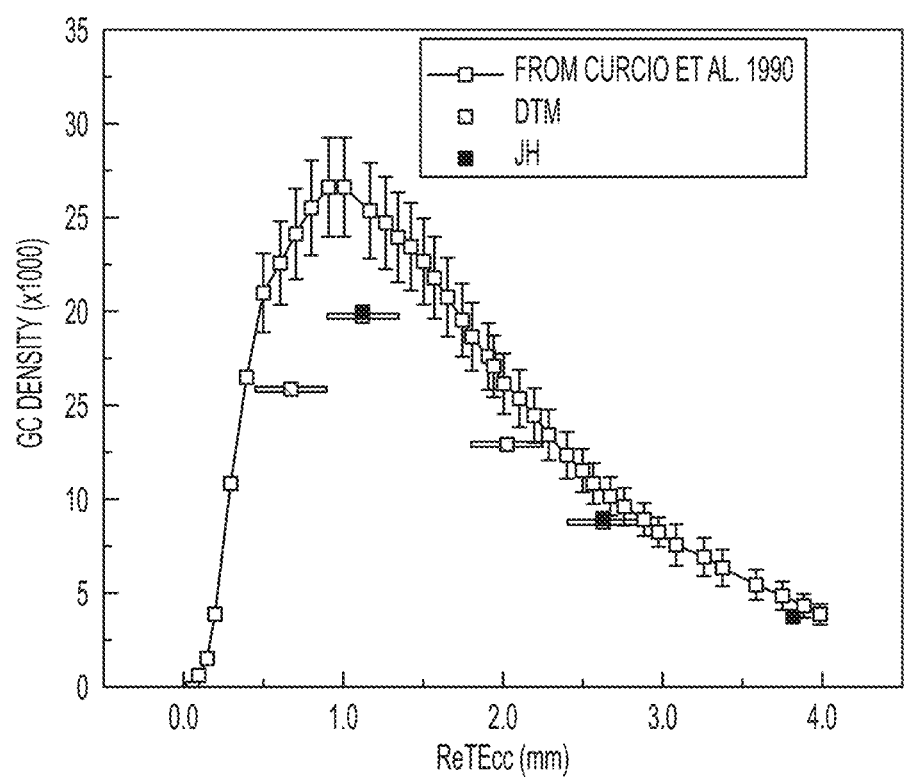
FIG. 20 is a graph of ganglion soma density as a function of retinal eccentricity.
Figure 21:
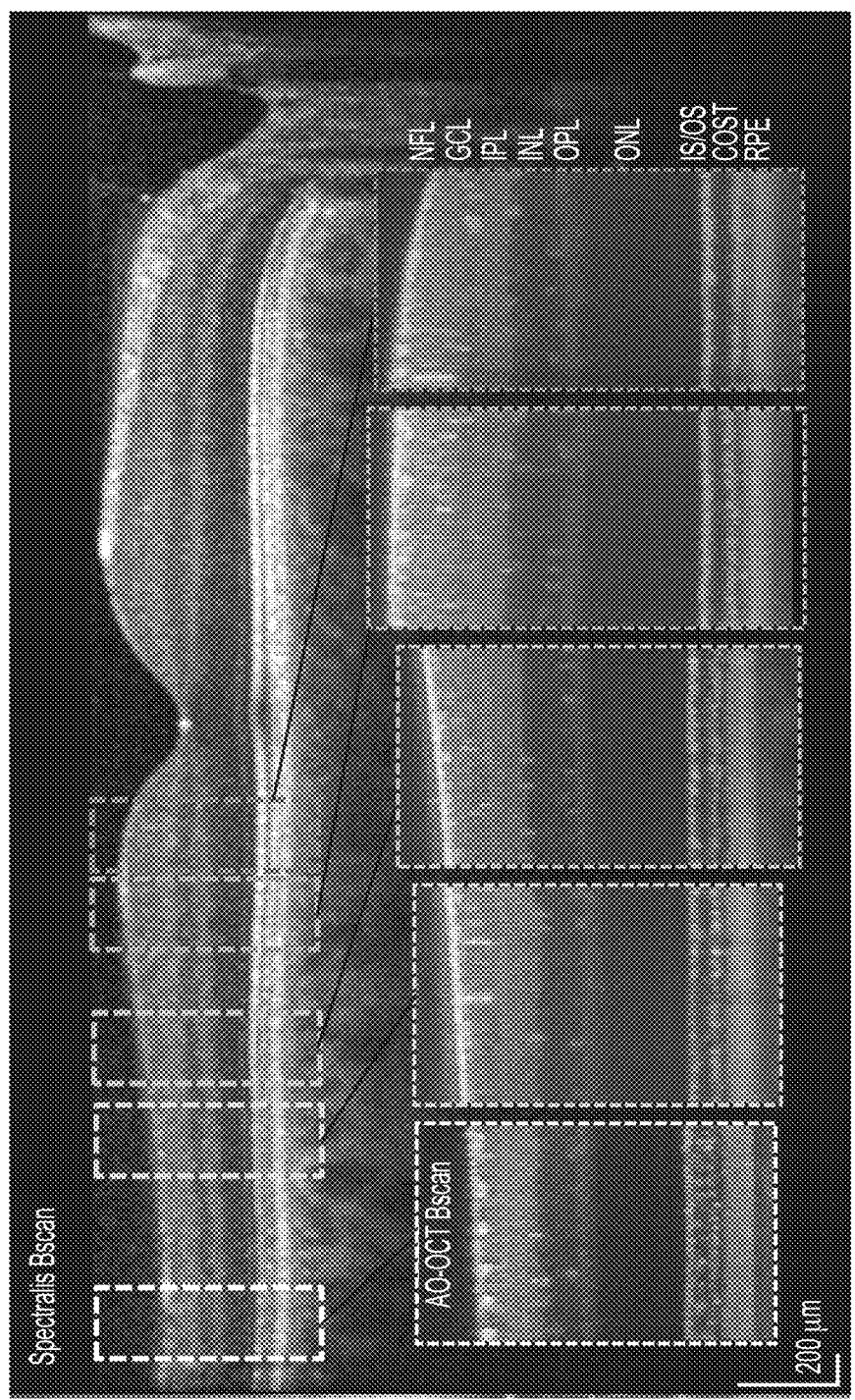
FIG. 21 provides cross sections of AO-OCT volume images.
Figure 22:
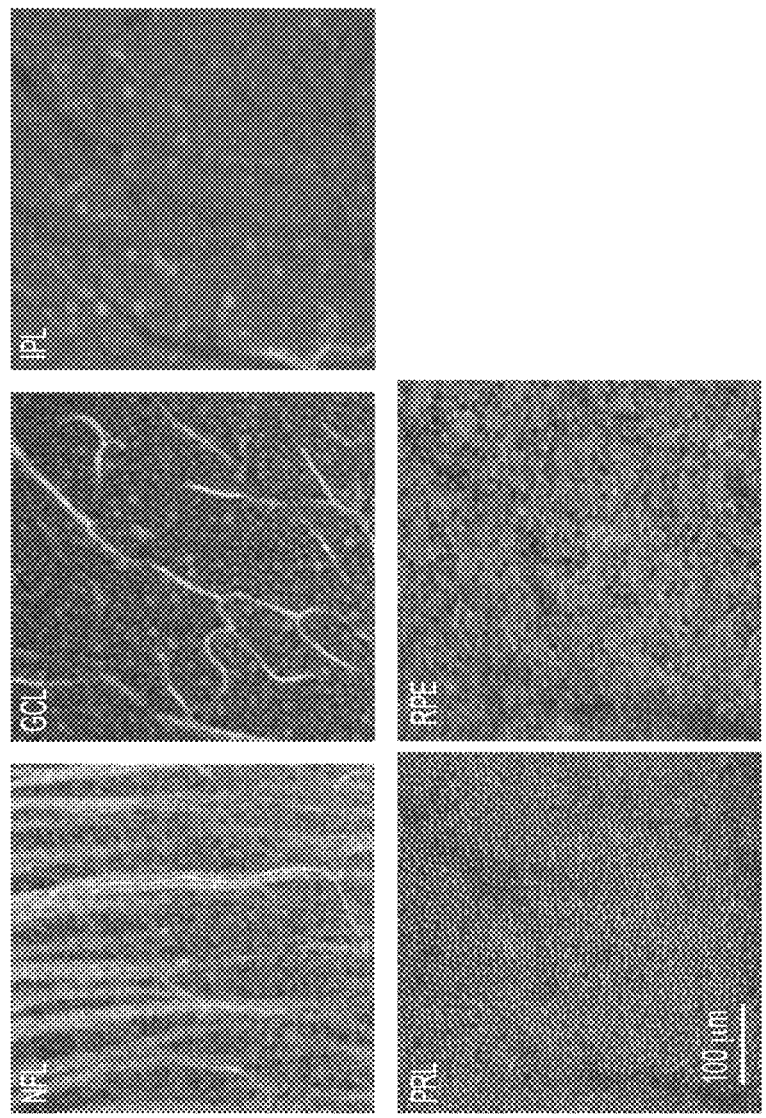
FIG. 22 provides en face cross sections across the retinal thickness.

FIG. 19 provides soma diameter distribution as a function of retinal eccentricity of one subject. FIG. 20 provides ganglion soma density as a function of retinal eccentricity in two subjects. Histologic estimates are shown from Curcio et al. 1990 for comparison. FIG. 21 shows cross sections of AO-OCT volume images, revealing stacking of soma in the retinal ganglion layer. Finally, FIG. 22 provides en face cross sections that reveal cell mosaics of different cell type at different depths in the retina, spanning the entire retinal thickness. Shown are the retinal nerve fiber layer (NFL), retinal ganglion cell layer (GCL), inner plexiform layer (IPL), photoreceptor layer (PRL), and retinal pigment epithelium (RPE). Cell mosaics are evident in GCL, IPL, PRL, and RPE.

As depicted in the above-described figures, the stack depth reached a maximum of 4 to 5 soma near 3°, decreased rapidly towards the fovea and more slowly to a minimum stack depth of one further away (see FIGS. 14, 15 and 21). A stack depth of two or more somas was observed up to 8°-9.5° and a single depth at 12°-13.5°. In the two subjects processed to date, average soma densities (cells/mm2) were 16,741 (1.5°-3°), 19,824 (3°-4.5°), 12,921 (6°-7.5°), 8,928 (8°-9.5°), and 3,743 (12°-13.5°) (see FIG. 20). The distribution (average±stdev) of soma diameter increased from 13.0±2.8 µm at 1.5°-3° to 14.5±3.3 µm at 12°-13.5° (see FIG. 19). The vast majority of the somas were of small size (12-15 µm), but notably larger somas (20-22 µm) were also observed and became more numerous with retinal eccentricity (see FIGS. 16 and 17). The depicted measurements of soma stack depth, density, and diameter are consistent with histologic reports published in Curcio C A, et al., J. Comp. Neurol, 1990.

As described above, AO-OCT imaging permits visualization and quantification of human RGC somas across the macula. To the best of our knowledge this is the first report of the 3D distribution and size of RGC soma in the living human eye.

In Vivo Imaging of Human Retinal Pigment Epithelium (RPE) Cells with AO-OCT

As previously indicated, the retinal pigment epithelium (RPE) plays a vital role in the support and maintenance of photoreceptors. Dysfunction of the RPE, however, can lead to photoreceptor and RPE degeneration, and the onset of numerous retinal diseases. Early manifestation of these disruptions occur at the cellular level where detection, monitoring, and treatment can be most effective. To this end in vivo imaging of RPE cells holds considerable promise, though such imaging has proven extremely challenging. As discussed above, this problem may be successfully addressed by using organelle motility as a novel contrast agent to enhance RPE cells in conjunction with 3D resolution of adaptive optics-optical coherence tomography (AO-OCT) to section the RPE layer.

In the following description, a central feature of the earlier work—organelle motility—is expanded by characterizing the dynamics of motility in RPE cells. The study quantifies dynamics in terms of an exponential decay time constant ($\tau$), the time for motility to decorrelate the speckle field across an RPE cell. This characterization has two fundamental uses. First, it provides a motility baseline for normal, healthy RPE to which we can compare diseased RPE. Second, it predicts the extent to which the lengthy 90-min imaging protocol for individuating RPE cells in the above-described work can be reduced, a desirable feature for clinical use.

Methods

Description of AO-OCT Imaging System

A description of the Indiana AO-OCT system used in this study is available in Liu Z., Kocaoglu O. P., Miller D. T., In-the-plane design of an off-axis ophthalmic adaptive optics system using toroidal mirrors, Biomed Opt Express. 2013; 4:3007-29 and Kocaoglu O. P., Turner T. L., Liu Z. L., Miller D. T., Adaptive optics optical coherence tomography at 1 MHz, Biomedical Optics Express. 2014; 5:4186-4200, the entire disclosures of which being hereby expressly incorporated herein by reference. Relevant to this study, the AO-OCT system used a single light source, a superluminescent diode with central wavelength of 785 nm and bandwidth of 47 nm, for both AO-OCT imaging and wavefront sensing. Confocal 3D-resolution of the system in retinal tissue (n=1.38) was nominally ~1.7×1.7×4.2 µm3 (width×length×depth). This resolution surpasses those of clinical OCT scans in lateral (>4.5×) and axial (>1.8×) resolutions, yielding a volume resolution 36× better. The systems acquired A-lines at a rate of 500 KHz by using 2-camera mode in order to track the fast speckle dynamics of the RPE cells. The data stream from the system was processed and displayed using custom CUDA software developed for parallel processing by an NVIDIA Titan Z general purpose graphic processing unit. Frames were processed at 20 per second (fps) for real-time visualization of A-scans, fast and slow B-scans, and C-scan (en face) projection views of the retinal layers of interest.

Experimental Design

Four subjects (S1, S2, S3, and S4), free of ocular disease, were recruited for the study. All subjects had best corrected visual acuity of 20/20 or better. Eye lengths ranged from 23.56 mm to 25.40 mm as measured with IOLMaster® (Zeiss, Oberkochen, Germany) and were used to correct for axial length differences in scaling of the retinal images.

Intensity of the AO-OCT beam was measured at 400 µW at the cornea that is below the safe limits established by ANSI for the retinal illumination pattern used and length of the experiment. The right eye was cyclopleged and dilated with one drop of Tropicamide 0.5% for imaging. The eye and head were aligned and stabilized using a bite bar mounted to a motorized XYZ translation stage.

AO-OCT volumes were acquired at 7° temporal to the fovea. For each subject, 33 to 62 AO-OCT videos were collected at 1 min. or less interval and time stamped. Volumes were 1°×1° at the retina and A-line sampled at 1 µm/pixel in both lateral dimensions. Each video consisted of 15 volumes that were obtained at high speed (500 KHz A-scan rate; 5 Hz volume rate) to capture temporal dynamics of RPE cell motility up to 2.5 Hz. In order to more completely characterize the RPE motility, two additional imaging sessions were performed on one of the subjects. 50 successive AO-OCT volumes were acquired without break for each session. During acquisition, the subject was instructed to blink once every 5 seconds in order to maintain good tear film quality while minimizing the number of volumes lost due to blinking.

3D Image Registration and Data Analysis 3D registration was applied to the entire AO-OCT volume, followed by layer segmentation and data analysis to the following three principle reflections: cone inner segment/outer segment junction (IS/OS), cone outer segment tip (COST), and RPE. These three processing steps were realized with custom algorithms developed in MATLAB (Mathworks; Nattick, Mass., U.S.A.).

Volumes with unacceptable motion artifacts were removed. Remaining volumes were combined into a single, time-stamped video and then registered in all three dimensions with subcellular accuracy to correct for motion artifacts. Registration to this level was necessary to prevent masking of organelle motility within individual RPE cells, which themselves were identified in the averaged, registered RPE en face image. Two additional layers were selected as motility controls (see FIG. 23 (image (A)): reflections from the cone outer segment (IS/OS+COST) layer and cone/rod axon (PR axon) layer. IS/OS+COST reflection was selected as it is known to be—in ensemble—stable over the time duration of the experiment (<10 min.), and therefore characterized by a large decay time constant ($\tau$). In contrast, PR axon reflection was selected as the weak signal there is dominated by white noise and therefore characterized by a delta-like $\tau$.

To assess temporal dynamics of RPE motility, a correlation function (CF) was computed for the reflectance trace of individual RPE cells, as well as corresponding regions of the two control layers: IS/OS+COST and PR axon. Each RPE cell area was defined by a Voronoi region. An ensemble CF was determined by averaging across all RPE cells (or all regions of the same layer) and defined as the motility function. Because $\tau$ is large for IS/OS+COST, the motility function of each layer was normalized to that of IS/OS+COST, in this way removing any system and residual eye motion contribution, and providing a more accurate estimate of the RPE motility time constant. An exponential fit was then applied to the normalized RPE motility function to determine $\tau$ of RPE by using the model: $y = A \times \exp(-t/\tau) + B$, where t is time, $\tau$ is the time constant, and A and B are fitting parameters.

Results

AO-OCT Imaging of Cones and RPE Cells

Figure 23:
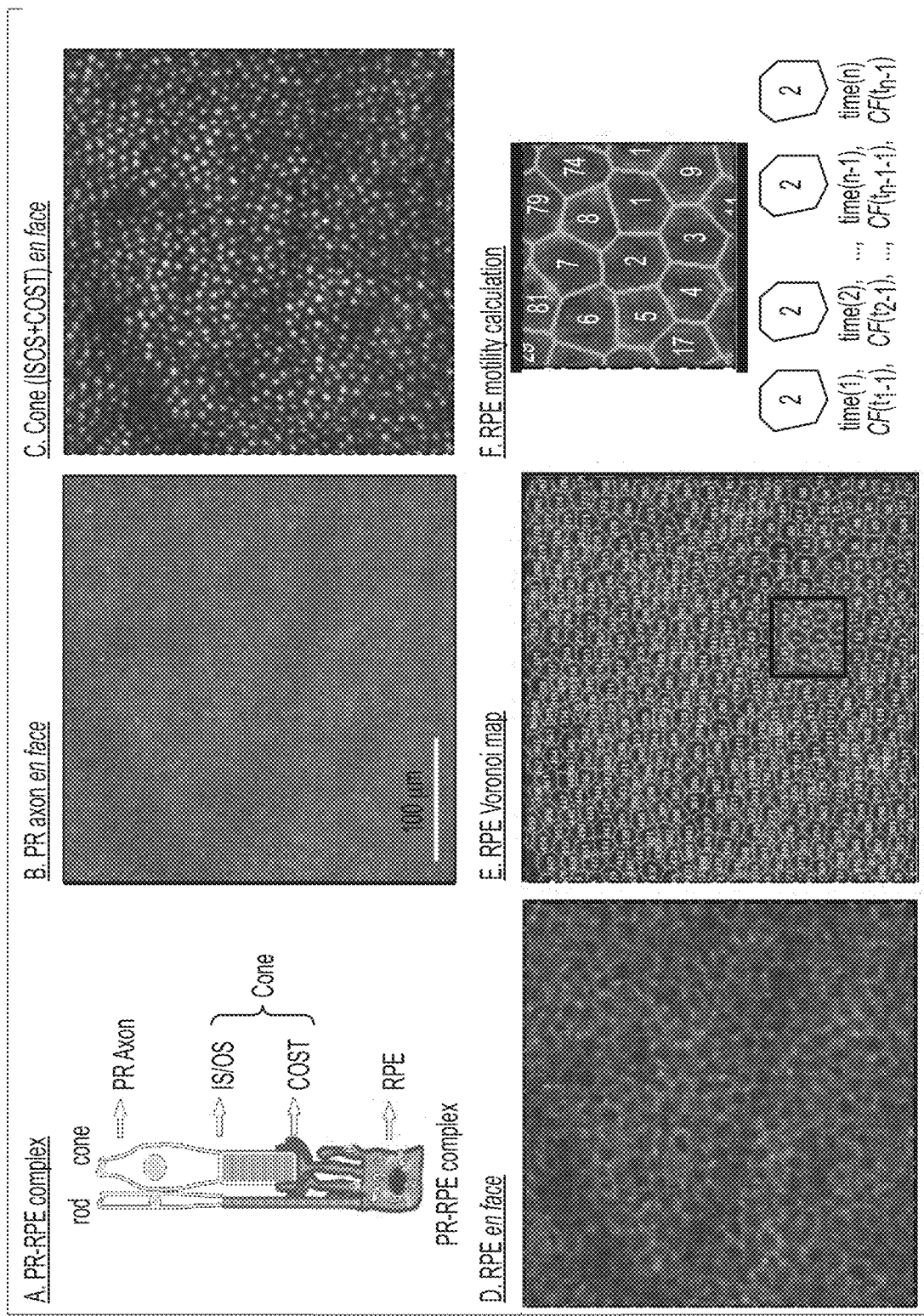
FIG. 23 provides AO-OCT imagining of the RPE and cone layers in a subject.

The RPE cell mosaic and quantified its motility function was successfully observed in all four subjects. FIG. 23 shows a representative AO-OCT result on one subject and illustrates the different appearance of the three layers used in this study: PR axon, cone (IS/OS+COST), and RPE. Depth locations are marked in FIG. 23 (image (A)) and corresponding averaged, registered en face images shown in FIG. 23 (images (B)-(D)). As expected, the image of PR axon in FIG. 23 (image (B)) shows no clear cell structure because of the weak reflectance at that depth. Unlike PR axon, bright regularly spaced cells are observed in the IS/OS+COST and RPE images in FIG. 23 (images (C), (D)) with densities (cone: 11,406 cells/mm$^2$; RPE: 4,834 cells/mm$^2$) consistent with histology and previously reported in vivo imaging. The RPE voronoi map in FIG. 23 (images (E) and (F)) was used to calculate motility function of each RPE cell.

More specifically, FIG. 23 shows AO-OCT imaging of the RPE and cone layers in a 26-year-old subject (S2) at 7° temporal retina. FIG. 23 (image (A)) is a schematic cartoon that depicts the three layers analyzed in this study: (1) PR axon, (2) IS/OS+COST, and (3) RPE. FIG. 23 (images (B)-(D)) are en face images from average of 45 registered AO-OCT volumes at depth of (B) PR axon, (C) cone (projection of cone IS/OS and COST), and (D) RPE. Each RPE cell in FIG. 23 (image (D)) is represented by a Voronoi cell in FIG. 23 (image (E)). FIG. 23 (image (F)) is a magnified view of Voronoi cells in red box superimposed on RPE map. The motility function (defined as CF) was calculated across each Voronoi cell, an example for one RPE cell is diagrammed at bottom of FIG. 23 (image (F)).

Figure 24:
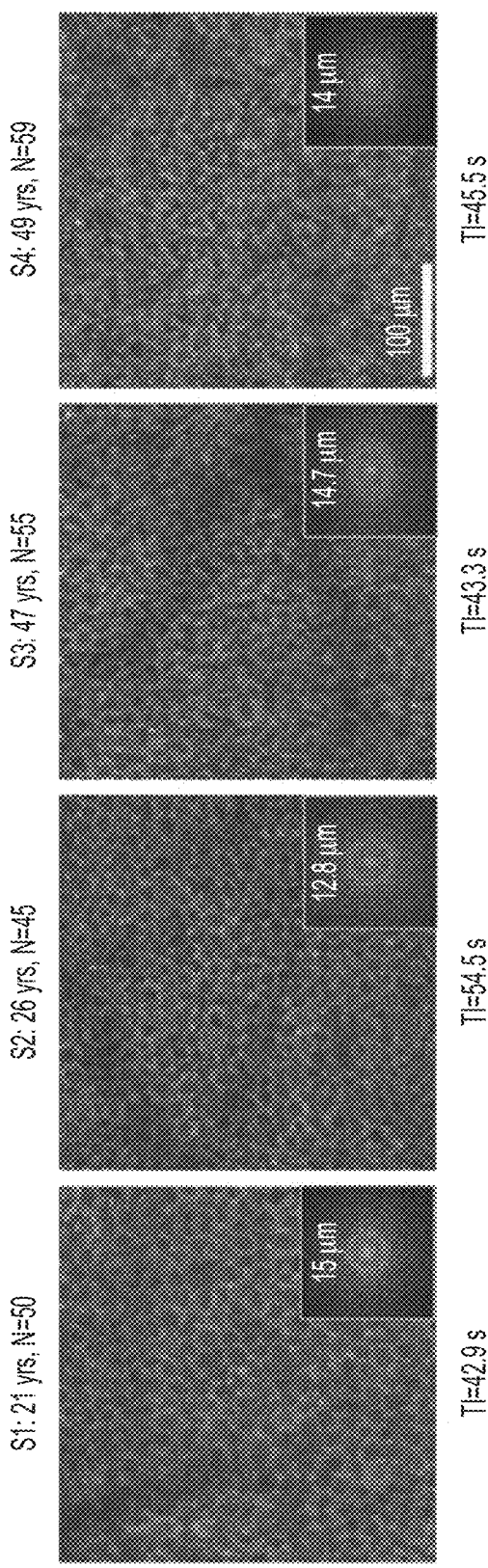
FIG. 24 provides averaged, registered RPE images for subjects.

As shown in FIG. 24, the RPE cell mosaic is revealed in all four subjects using the AO-OCT method and an average time interval (TI) of approximately 1 min. between consecutively captured volumes. This suggests that organelle motility occurs on a faster time scale, i.e., a decay time constant ($\tau$) less than 1 min. For comparison, a time interval three times longer (3 min.) yielded RPE cell images of comparable quality and further supports a motility time constant that is shorter than the imaging interval. Also shown in FIG. 24 is the corresponding 2D power spectra of the RPE images, which show rings of concentrated energy. Average ring radius equates to a row-to-row cell spacing of 14.1±1.0 µm (7°) for the four subjects, which is in agreement with measured cell spacing in the literature.

More specifically, in FIG. 24 averaged, registered RPE images for all four subjects imaged at 7° temporal to the fovea are shown. Subjects are ordered by increasing age. N is the total number of images averaged. TI denotes mean time interval for acquiring the RPE images. 2D power spectra are superimposed at bottom right of each en face image.

Characterization of RPE Cell Motility

Figure 25:
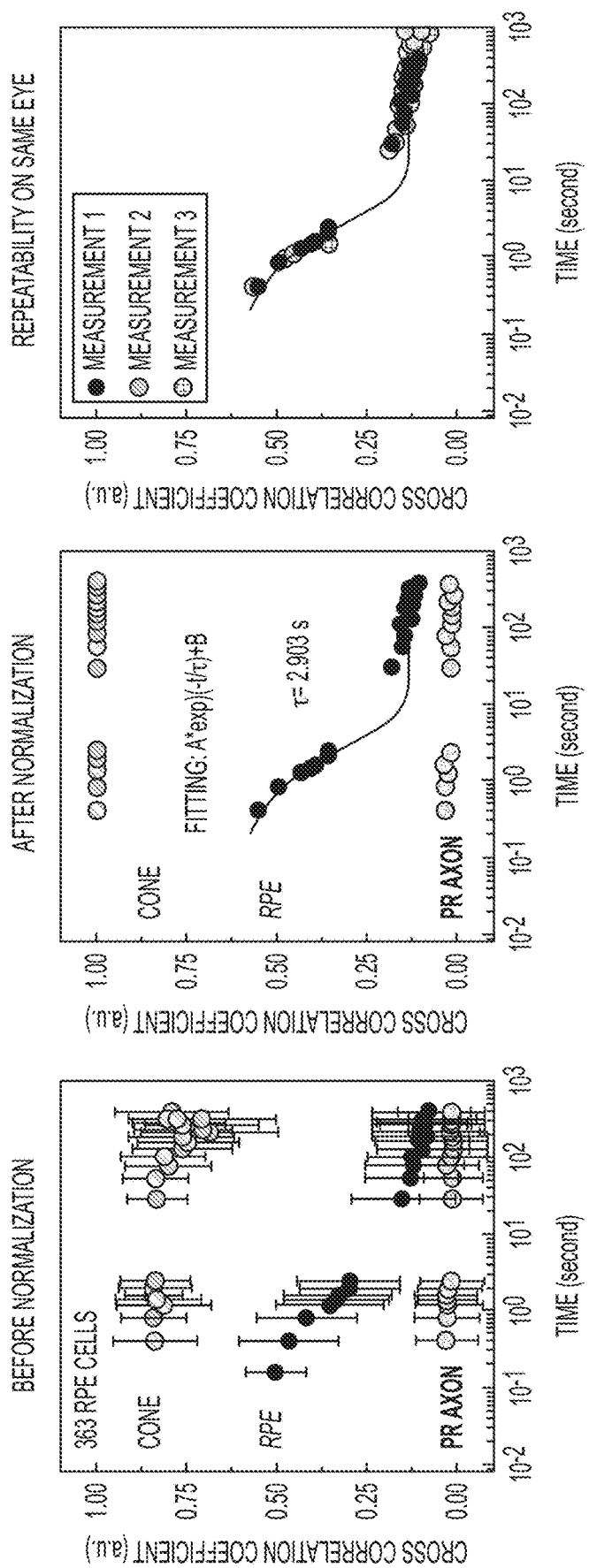
FIG. 25 provides graphs of motility dynamics measured at three retinal depths in a subject.

Referring now to FIG. 25, motility dynamics measured at three retinal depths in subject 4 are shown: PR axon, IS/OS+COST, and RPE. The left image shows a raw motility function before normalization to IS/OS+COST layer. Error bars represent standard deviation across 363 RPE cells. The middle image shows a motility function normalized to IS/OS+COST layer to remove residual motion and system errors. The right image shows that three repeated measurements on the same subject and same retinal location are highly consistent.

Figure 26:
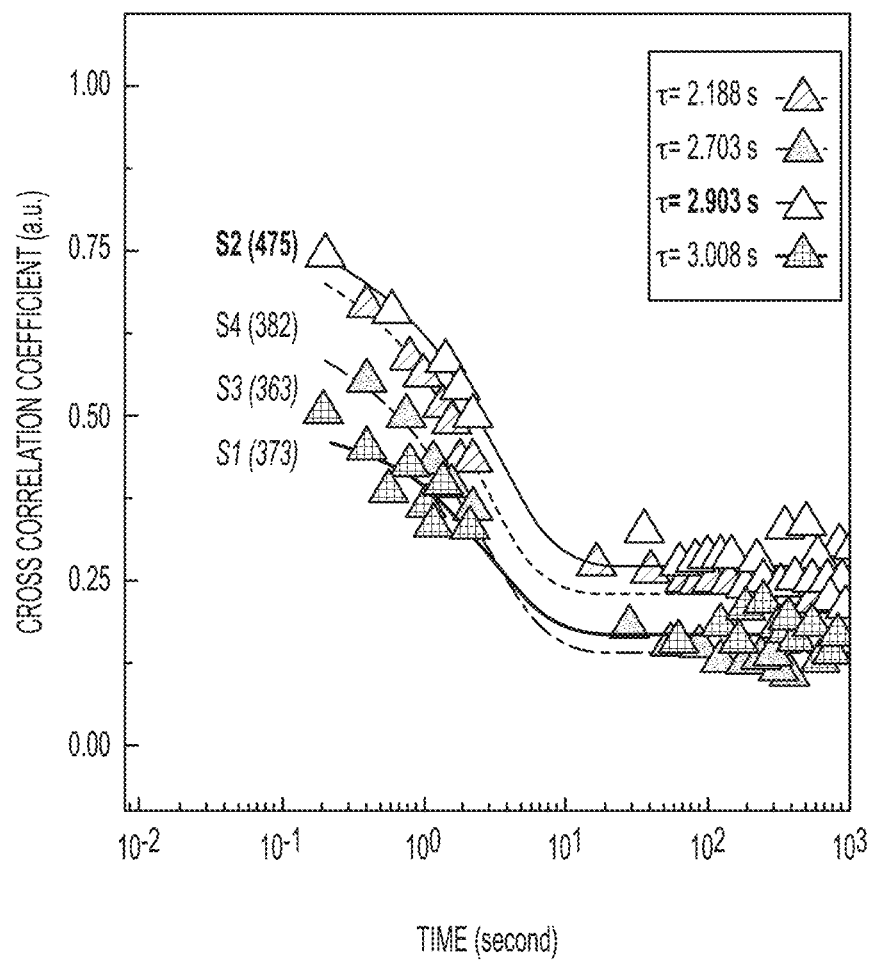
FIG. 26 is a graph depicting motility dynamics measured in four subjects.

More specifically, FIG. 25 (left) shows the RPE motility function, averaged across 363 RPE Voronoi cells. Motility of the two controls (IS/OS+COST and PR axon) are also plotted. As expected, decorrelation of the RPE decreases at a rate faster than IS/OS+COST and slower than PR axon. IS/OS+COST is relatively stable regardless of time interval, confirming our original expectations. Likewise, PR axon shows a delta-like correlation with near zero correlation measured for the first sample point at 0.3 s, again confirming expectation. To determine $\tau$ for RPE, system and residual motion errors were removed by normalizing to IS/OS+COST, see FIG. 25 (middle), that plots the same three motility functions. For this example, the exponential fit gives $\tau=2.9$ s for RPE, indicating approximately 3 s is needed for organelle motility to decorrelate the speckle noise pattern in the RPE cells. To test repeatability, FIG. 25 (right) shows three repeated measurements on the same eye. As evident by the considerable overlap of data points in the figure, the measurements show strong consistency. For the four subjects, average $\tau$ (based on 363 to 475 RPE cells per subject) was 2.70±0.36 s (FIG. 26) and represents a preliminary baseline for the normal, healthy eye. FIG. 26 shows motility dynamics measured in four subjects based on 363 to 475 RPE cells per subject.

Discussion

Characterizing RPE Cell Motility

RPE organelles are under seemingly constant motion as they execute cellular and molecular tasks that encompass essentially every aspect of cell physiology. Thus normal organelle motion is fundamental to normal RPE function. Not surprisingly then, animal studies have shown that diseased RPE cells exhibit abnormal organelle motility, thus pointing to motility as a potentially sensitive indicator of cell health. However, how this translates to the living eye and to humans remains unknown. The above-described study took advantage of the interferometric nature of AO-OCT to measure motion-evoked changes in the scatter of light within individual RPE cells in the living human retina. These changes were attributed to organelle motility. With this attribution, the organelle motility was quantified in terms of the cross correlation coefficient and with this metric organelle motility was found to vary rapidly with a time constant of about 3 seconds (See FIGS. 25-26), i.e., the scatter pattern generated by the RPE organelles decorrelated in ~3 seconds. The method demonstrated high repeatability (See FIG. 25 (right)) and yielded correlations expected of the IS/OS+COST reflection (high stability) and PR axons (no stability) (See FIG. 25 (left)).

Optimizing RPE Cell Imaging

The second implication of the motility study concerns RPE cell imaging. Because the time constant of organelle motility defines the shortest time duration over which RPE images can be acquired, it carries clinical significance. It has been found that volumes acquired over 90 minutes at 3 minute intervals (~35 in total) generated sufficiently different noise patterns across the RPE image that averaging of registered images revealed the RPE cell mosaic. While successful, 90 minutes of imaging has little clinical utility. In the current study, the 3 minute interval was shortened to less than 1 minute, while preserving clarity of the RPE cell mosaic (See FIGS. 23-24). This factor of three reduction results in a 30 minutes imaging session, which while improved still may preclude clinical use.

This begs the question then as to how short the imaging session can be while still retaining clarity of the RPE cell mosaic. The measurement of the motility time constant provides a direct prediction of what this should be (See FIGS. 25-26). Specifically, the motility measurements yield a ~3 second time constant, which implies a minimum time interval between RPE images of ~3 seconds. This results in a total imaging session duration of just 90 seconds (3 s/image×30 images).

Motivated by this prediction, the imaging protocol was further optimized for testing the optimal imaging time for RPE cell contrast enhancement. To do so, required increasing the speed of the AO-OCT image saving routines. This proved non-trivial given the large size of the 4D data streams that had to be saved and resulted in some compromises in the acquisition protocol. What resulted was two imaging protocols, one that provided an average imaging interval of 0.2 seconds (which is <3 s prediction) and another of 12.9 s (which is >3 s prediction). Thus, the two protocols straddled the predicted time constant. To assure fairness, the same number of AO-OCT volumes was averaged for the two protocols, acquired on the same patch of retina in the same eye (S2), and followed the same processing steps established above. Results are presented in FIGS. 27A-D.

With the average time interval of 12.9 s (FIG. 27A), individual RPE cells are clearly visible and retain the same cell clarity as evident with the longer 1 minute time interval (compare to second image in FIG. 24, which is of the same subject). In contrast, the average time interval of 0.2 s (FIG. 27B) yields a notably degraded image in which individual RPE cells are difficult to identify. Both time intervals (12.9 s and 0.2 s) yield results that are consistent with the ~3 second time constant measured for RPE organelle motility.

Figure 27A:
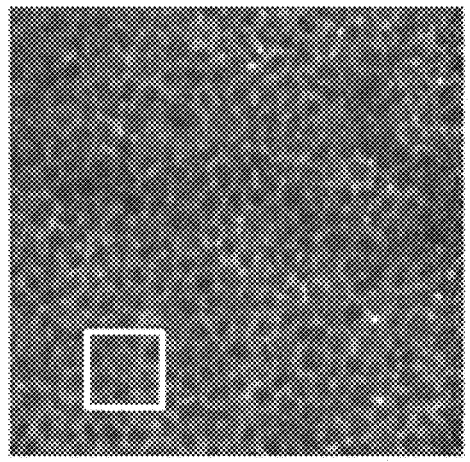
FIGS. 27A-D provides images relating to testing a 3-second prediction for RPE organelle motility.
Figure 27B:
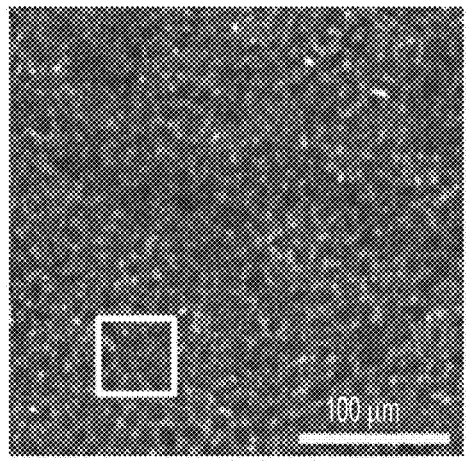
Figure 27C:
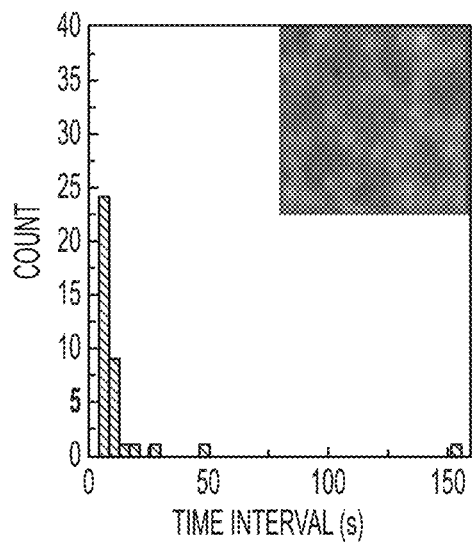
Figure 27D:
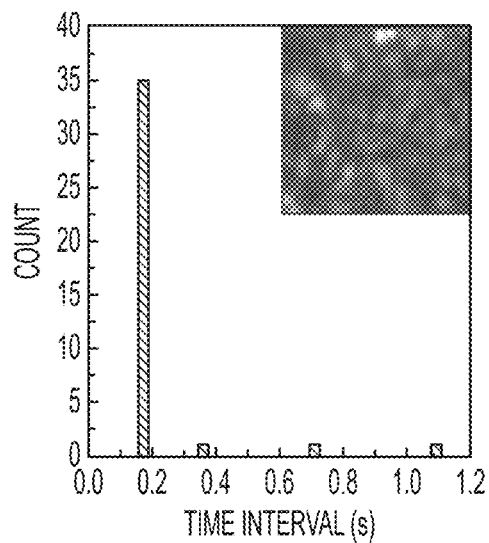

More specifically, FIGS. 27A-D shows testing of 3-second prediction for RPE organelle motility. En face images are shown generated by averaging 39 volumes with an average time interval of (A) 12.9 s and (B) 0.2 s for the same retinal patch in subject S2. FIGS. 27C-D correspond to histograms of the time intervals for the 39 volumes. The top right corner of FIGS. 27C-D show magnified sub-images (50 µm×50 µm) of the small boxes in FIGS. 27A-B, respectively.

Thus, the above description provides a method based on AO-OCT for measuring organelle motility in individual RPE cells. The motility decay constant ($\tau$) in four subjects was measured and showed that motility decorrelates speckle noise in about 3 seconds. This value has two fundamental uses. First, it establishes a preliminary baseline to compare motility of diseased RPE cells. Second, it predicts that a 90-min. imaging protocol for individuating RPE cells can be reduced by 60×, down to just 1.5 min.

In another embodiment of the present disclosure described below, the 3D resolution of the AO-OCT method was 2.4×2.4×4.7 µm3 (width×length×depth), sufficient to resolve GCL somas in any dimension. 1.5°×1.5° AO-OCT volume images were acquired along the horizontal meridian of the macula from four subjects free of ocular disease. AO-OCT videos were acquired at each retinal location with the system focused precisely at the GCL. In post-processing, volumes were registered and averaged, and GCL somas were identified. The description below is based on a total count of over 42,000 GCL somas at 26 different locations in the four subjects. The 3D spatial coordinates of the GCL soma centers were marked and used to quantify: soma stack thickness, diameter, reflectance, density, and distribution of primary GC subtypes and GC projection onto cone photoreceptors.

Results and Discussion

Averaging and Registering AO-OCT Volumes

Figure 28:
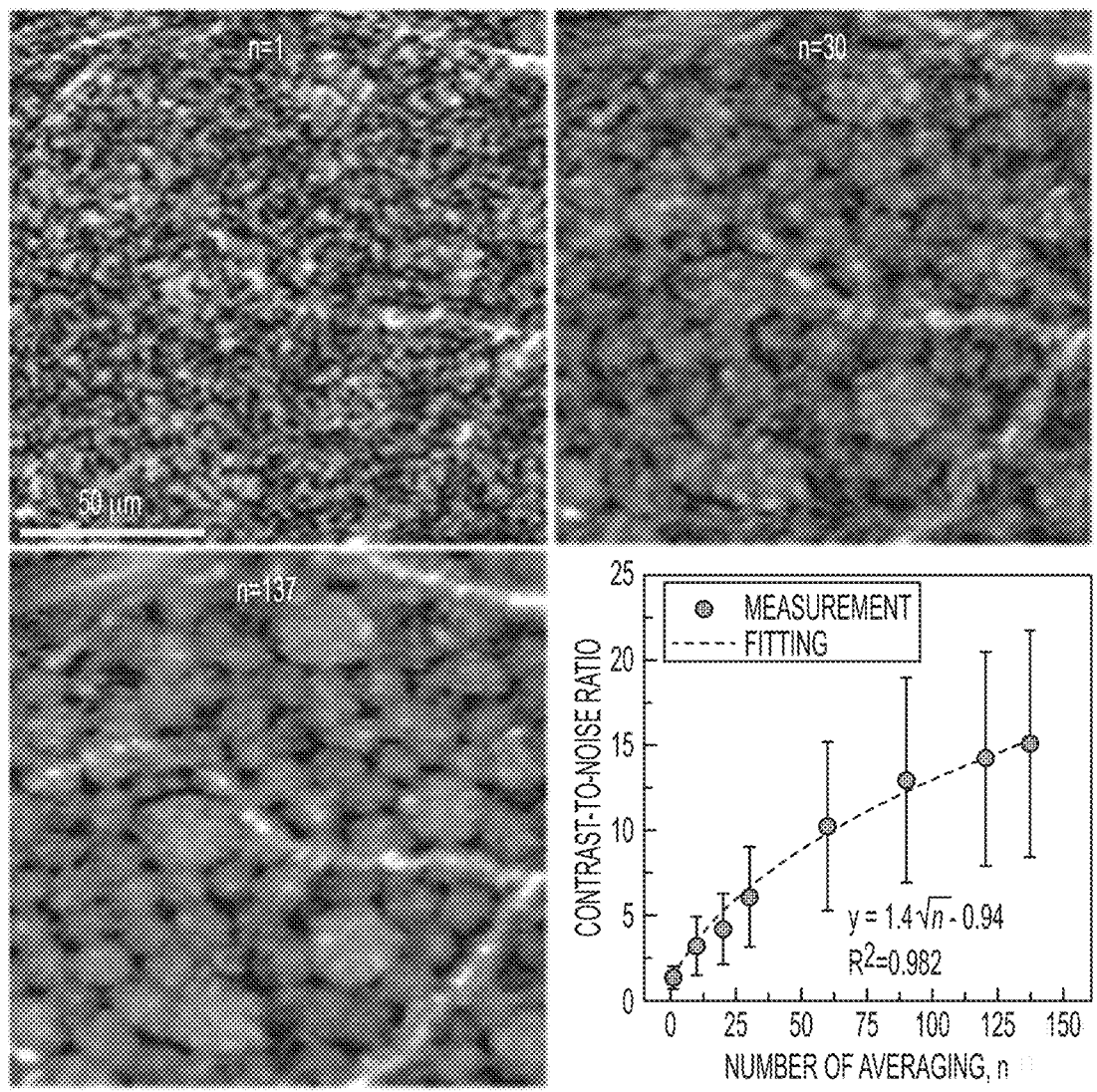
FIG. 28 provides images of a patch of retina with different amounts of averaging and a plot of contrast-to-noise ration of GCL somas.

Imaging with coherent light produces speckle that contains both noise and object information (e.g., soma shape), the former preventing observation of the latter (see example in FIG. 28; n=1). FIG. 28 demonstrates that averaging registered AO-OCT images improves clarity of GCL somas. Magnified views of the same small patch of retina are shown with different amounts of averaging (n=1, 30, and 137 images). The images are from 12-13.5° temporal to the fovea in subject S3. The plot of FIG. 28 shows the contrast-to-noise ratio (CNR) of 120 individual GCL somas computed as a function of images averaged. Error bars denote ±1 standard deviation. CNR increase follows the square root of the number of images (dashed curve).

Organelle motion in the soma causes the noise to change from image to image, while the object information (soma) remains constant from image to image, assuming the images are registered to each other with an accuracy better than the size of individual somas. Therefore, averaging of images reduces speckle noise while retaining soma information. It has been empirically determined that averaging 100-160 registered AO-OCT volumes of the same retinal patch improves signal-to-noise ratio and image contrast, dramatically improving the clarity of individual GCL somas (see example in FIG. 28; n=137). As is further described below, the image enhancement due to motion of organelles inside somas and the ability to register to subcellular accuracy using a soma contrast metric may be quantified. As expected from the theory of independent noise realizations, soma contrast increases as the square root of the number of images averaged, experimentally increasing by a factor of 11 times with 137 volumes (see plot of FIG. 28).

Three-Dimensional Imaging of the Inner Retina

Figure 29A:
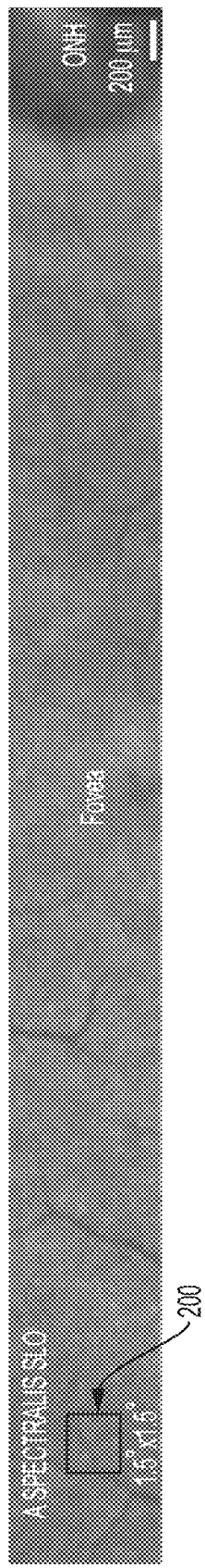
FIG. 29A is an image of a location of a fovea imaged with AO-OCT.
Figure 29B:
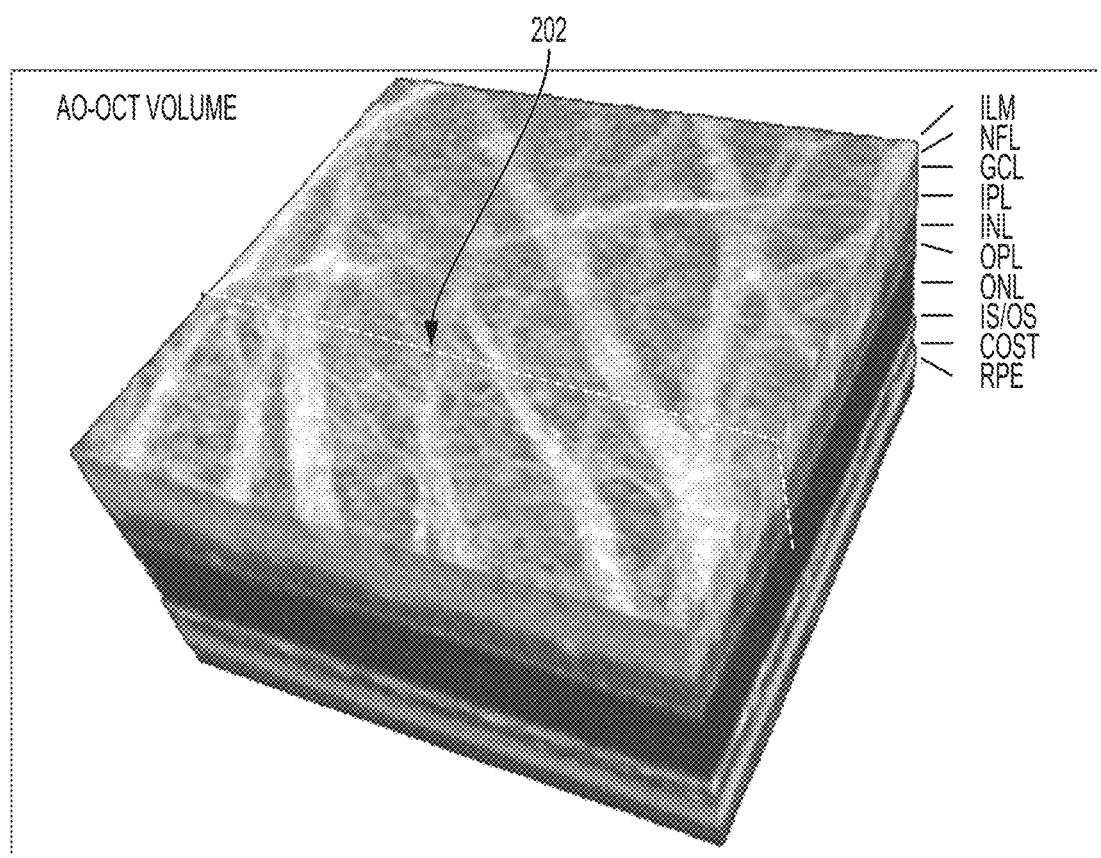
FIG. 29B is a perspective view of an AO-OCT volume.
Figure 29C:
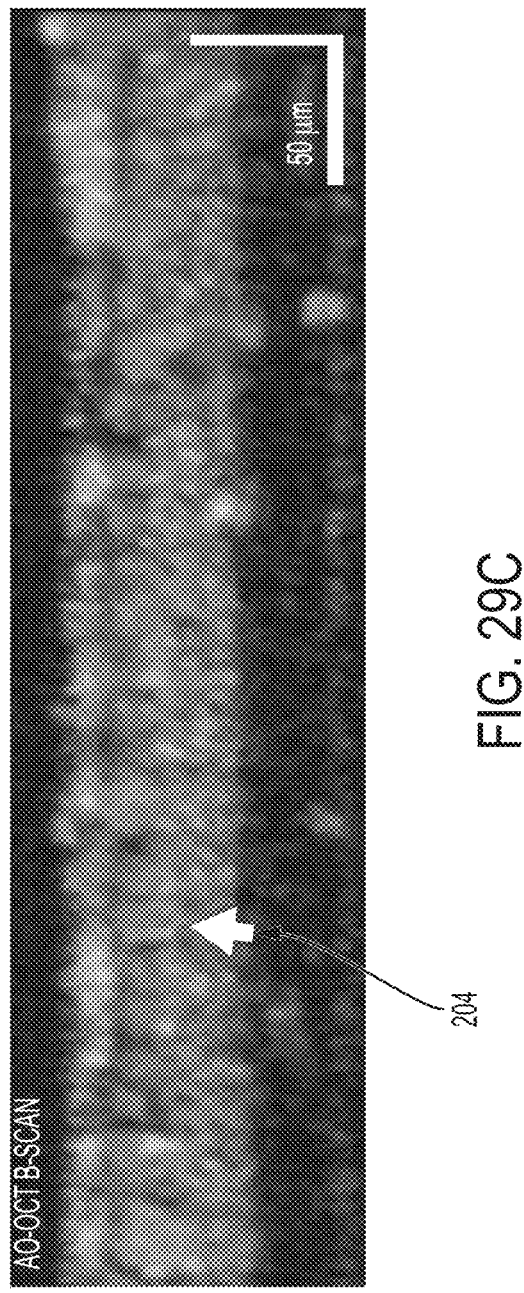
FIG. 29C is a cross-sectional view of FIG. 29B.
Figures 29D, 29E:
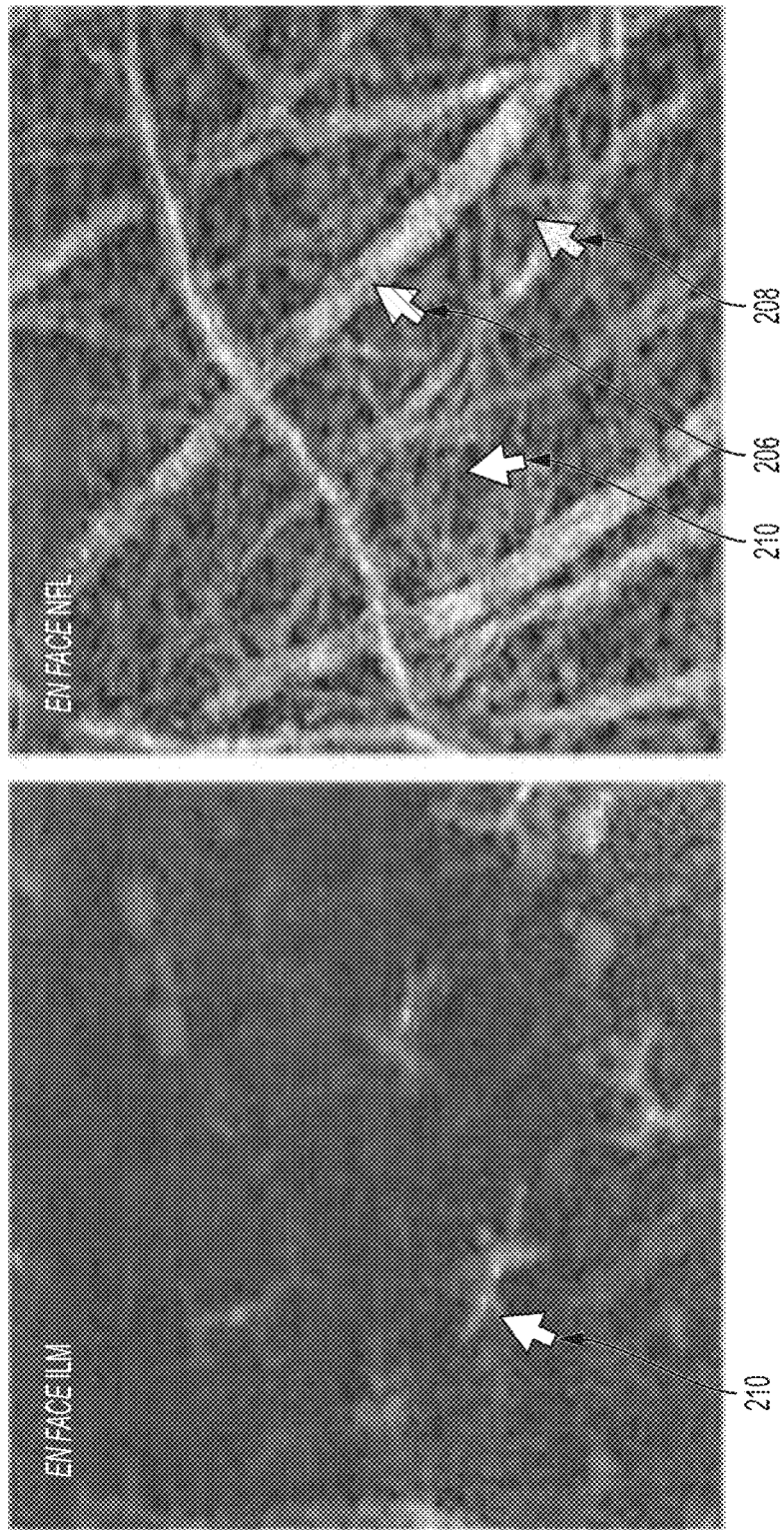
FIG. 29D is an image of a surface of ILM.
FIG. 29E is an image of a web of nerve fiber bundles across an NFL.

Referring now to FIGS. 29A-G, detailed views obtainable by the methods of the present disclosure are shown of the 3D mosaic of GCL somas, the adjacent ganglion axon bundles, the retinal vasculature, and cellular structures at the inner limiting membrane (ILM) and inner plexiform layer (IPL). Cellular structures of the inner layers of the retina using AO-OCT are shown. FIG. 29A includes a square 200 at 12-13.5° temporal to the fovea in subject S3 which denotes the location imaged with AO-OCT. In FIG. 29B, a three-dimensional perspective is provided of a registered and averaged AO-OCT volume with a dashed line 202 denoting the cross-section of the inner retina shown in FIG. 29C. Arrows 204 in FIGS. 29C and F indicate the same GCL soma. The images shown in FIGS. 29D and G were extracted at depths of 0, 13, 22, and 46 μm below ILM. The scale bar in FIG. 29G also applies to FIGS. 29D-F. FIG. 29D shows the surface of ILM. As shown, it includes bright, irregular star-like structures that sparsely cover the surface of the ILM and are consistent in appearance with individual astrocyte or microglial cells. In FIG. 29E, a complex web of nerve fiber bundles of varying size are shown dispersed across the NFL. Some have a diameter as large as 30 μm (arrow 206), which compares to previous AO-OCT observations. Others are as small as 3 μm, which matches the caliper of a single large GC axon. An arteriole/venule branches on the left. GCL somas appear between the overlying bundles near the image bottom (arrow 208). FIG. 29F shows a mosaic of GCL somas of varying size that tile the layer. Arrow 210 points to a large soma. Caliper of arteriole/venule in FIG. 29E is sufficiently large that it extends into the GCL. FIG. 29F further shows distinct edges of the vessel walls (arrows 212 and 214) and the tight abutment of GCL somas. FIG. 29G shows the dense synaptic connections between axons of bipolar cells and dendrites of ganglion and amacrine cells present as a uniform mesh of high spatial frequency irregularities in the IPL. Other layers indicated in FIG. 29B are the cone outer segment tip (COST), the inner segment/outer segment junction (IS/OS), the outer nuclear layer (ONL) and the outer plexiform layer (OPL).

After imaging the retinal tissue at a selected location, the resulting volume can be dissected digitally to show how a single, identified neuron is positioned in depth (cross-sectional view of FIG. 29C) and laterally (transverse slice of FIG. 29F). Transverse slices provide detailed views of many retinal features of interest, such as presumptive astrocytes or microglia at the ILM (FIG. 29D), GC axon bundles of various calibers (FIG. 29E), the mosaic of GCL somas of different characteristic sizes indicating different functional classes (FIG. 29F), and the dense mesh of dendrites and synapses between GCs, amacrine cells, and bipolar cells in the IPL (FIG. 29G). Together, these images provide a glimpse of the rich tapestry of neurons, glia, and blood vessels that can be appreciated by interactive inspection of the imaged volume.

GCL Soma Size and Stack Thickness

Referring now to FIG. 30, the GCL of recorded retinal volumes were inspected to estimate the size and layering of GCL somas at different retinal eccentricities. Specifically, FIG. 30 shows en face images extracted from GCL at increasing retinal eccentricity of subject S4. A mosaic of GCL somas is observed at each eccentricity. The graph of FIG. 30 shows GC soma density plotted along the horizontal meridian of the macula. Retinal eccentricity is converted to millimeters to compare with histology data. AO-OCT temporal data are the average from four subjects and nasal is from S4. The error bars denote ±1 standard deviation.

Figure 31:
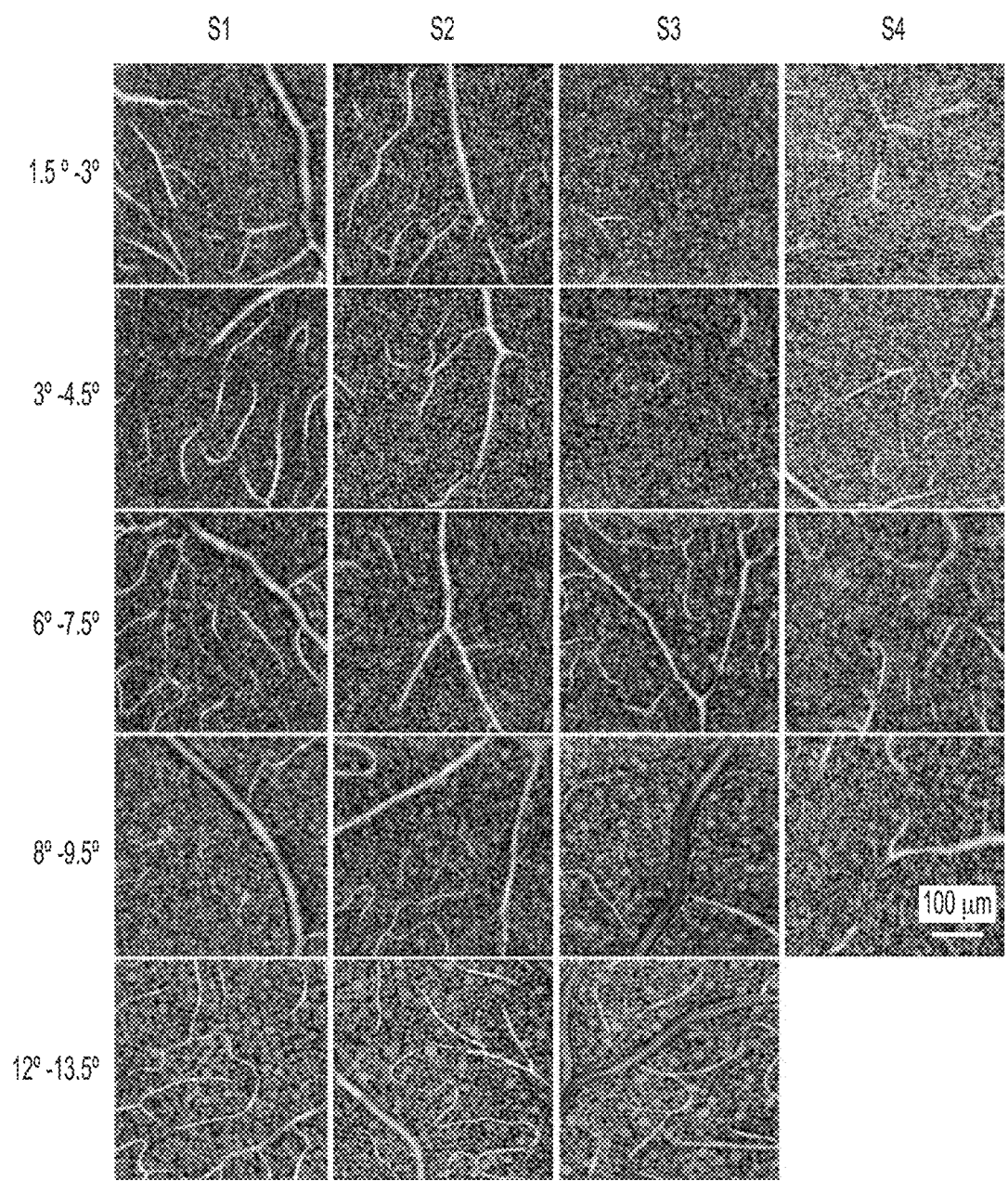
FIG. 31 provides cross-sectional views of the GCL as a function of retinal eccentricity for four subjects.
Figure 32A:
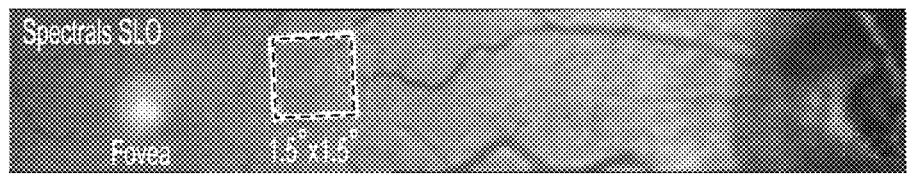
FIGS. 32A-D provide images of a location imaged with AO-OCT and cross-sectional views.
Figures 32B, 32C:
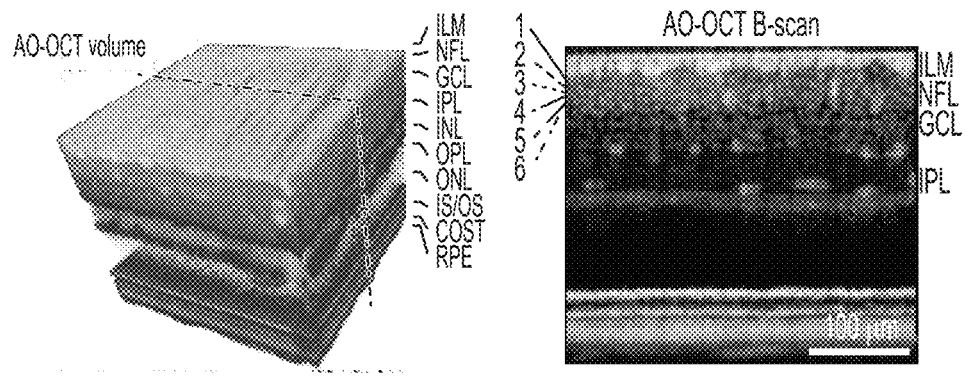
Figure 32D:
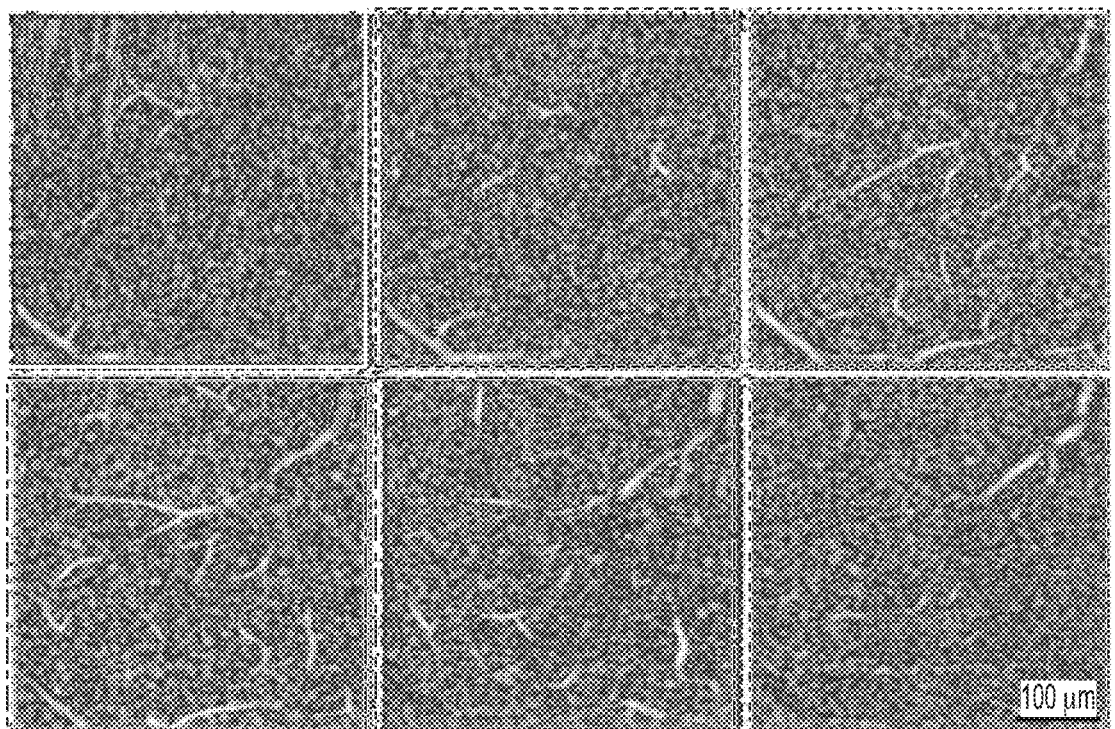
Figure 33:
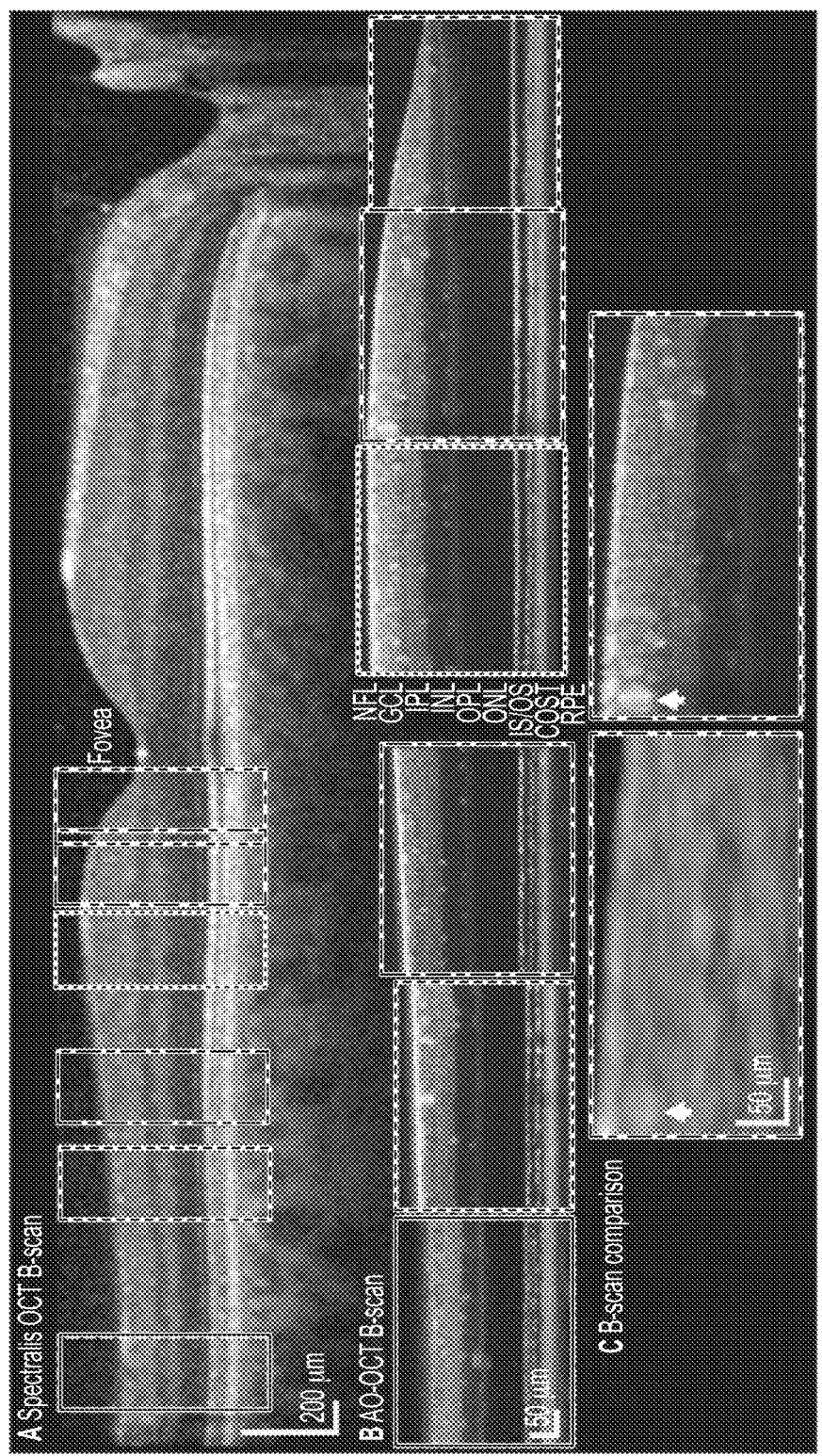
FIG. 33 provides images of a OCT B-scan showing six retinal locations where AO-OCT volumes were acquired and corresponding AO-OCT B-scans.

The example images of FIG. 30 and FIG. 31 clearly reveal the retinal gradient of soma size for all four subjects. The high axial resolution of the AO-OCT enables visualization of the layering of GCL somas in depth, necessary for measurements of cell density and observations of the arrangement of somas in gaps between nerve fiber bundles and around blood vessels extending through the entire GCL (see FIGS. 32A-D and 33). Stack thickness reached a maximum of 4-5 somas at 3-4.5° retinal eccentricity, decreasing rapidly toward the fovea and slowly away from it to a minimum thickness of 1. A thickness of ≥2 somas was observed up to 9.5° eccentric (FIG. 33). Note that counting the number of somas in a stack required some judgment due to the varied spacing and size of the somas. Soma size is a distinguishing property of GCs related to their function and central projection. In the images provided herein, somas near the fovea are small and homogeneous, possibly due to packing constraints for achieving high visual acuity. In contrast, the patches 12-13.5° eccentric contain the largest and most varied sizes. Central tendency and variability of soma size are captured by the frequency distributions plotted in FIG. 34A and FIG. 35. For the four subjects, the distribution of soma diameter is 11.4±1.8 μm (average±standard deviation) at 1.5-3° and 13.9±3.1 μm at 12-13.5°, a 22% and 72% increase in size and variation.

Figure 34A:
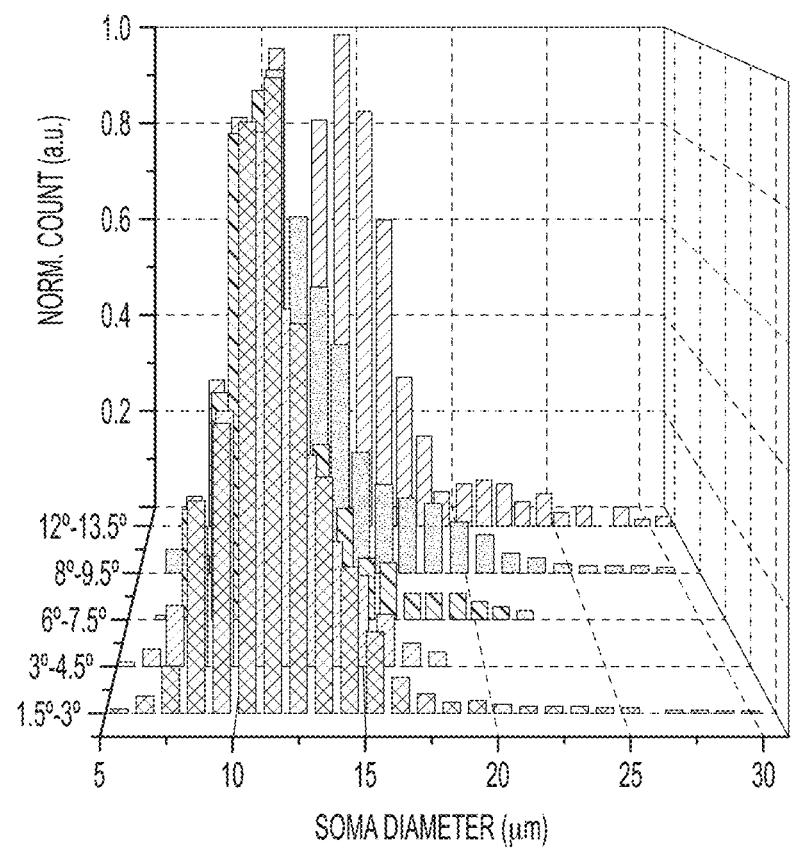
FIG. 34A is a plot of GCL soma size distribution by retinal eccentricity.
Figure 34B:
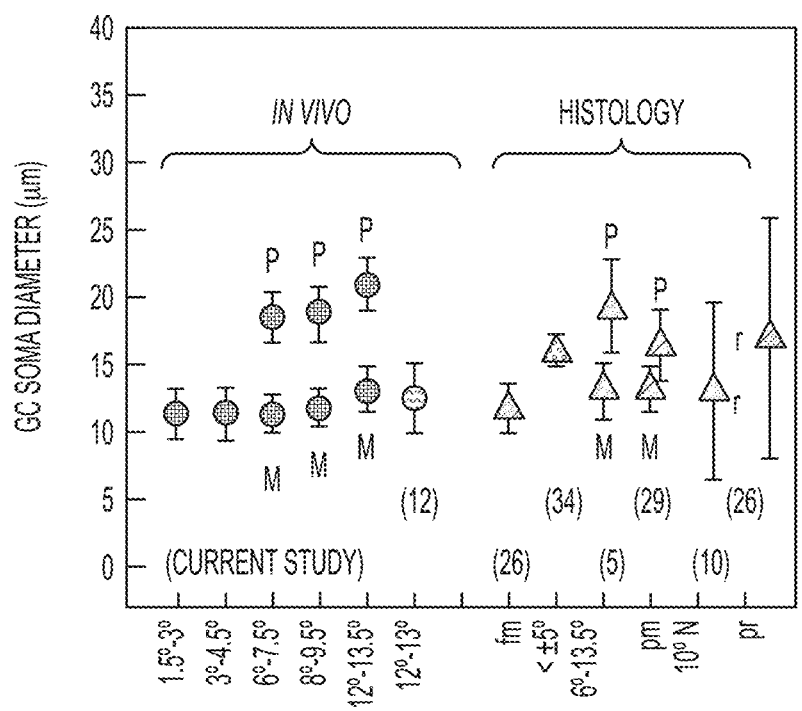
FIG. 34B is a plot of average GC soma diameter for four subjects.
Figure 34C:
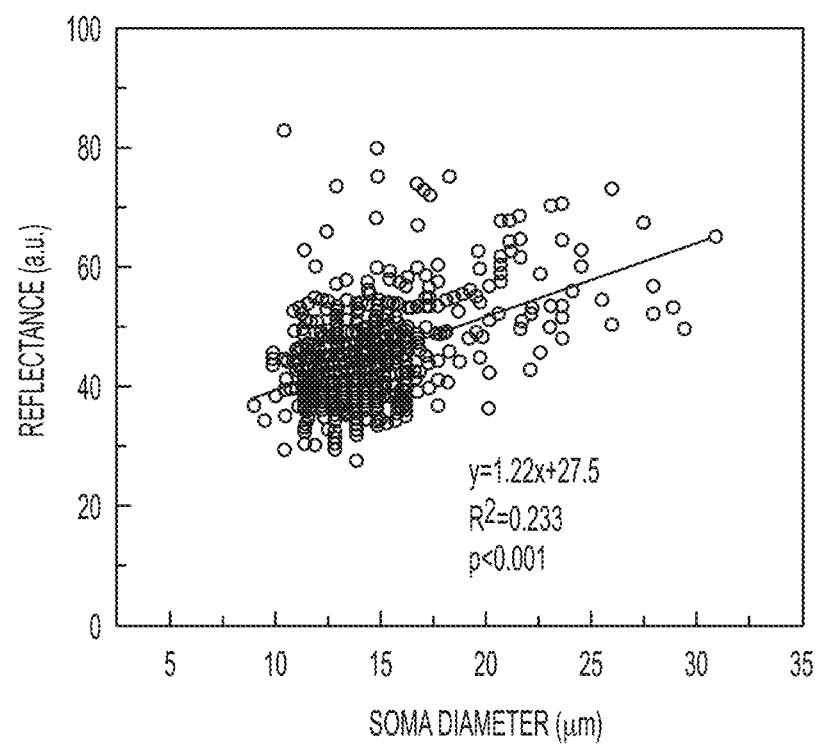
FIG. 34C is a plot of reflectance of GCL somas.
Figure 34D:
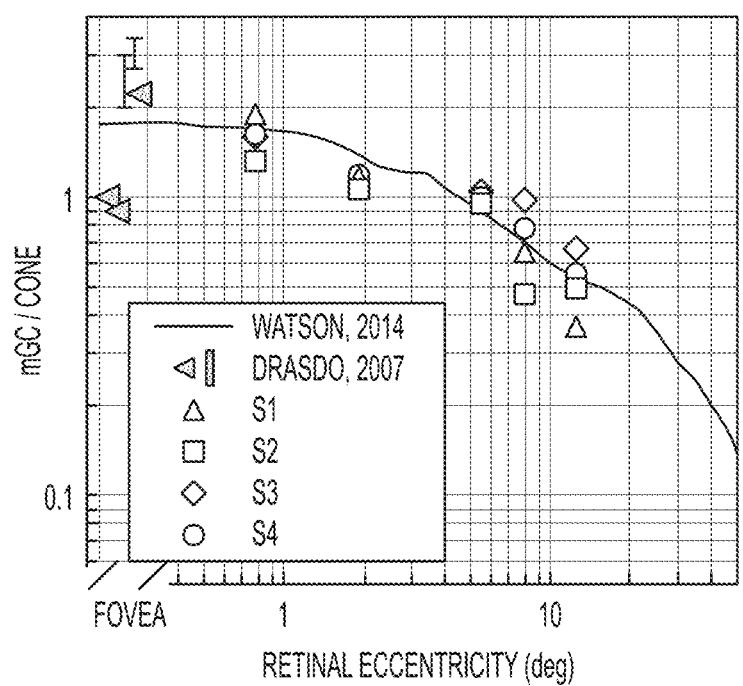
FIG. 34D is a plot of mRGC-to-cone ratio for four subjects.
Figure 35:
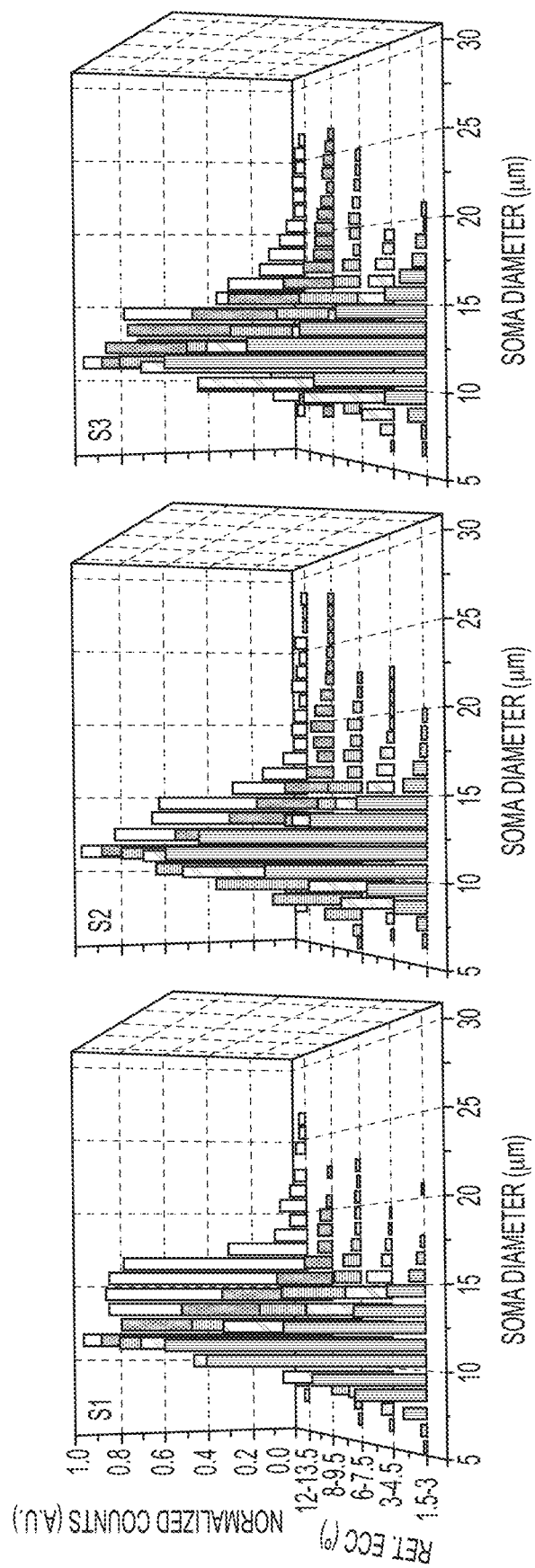
FIG. 35 provides plots of GCL soma size distributions for three subjects.
Figure 36:
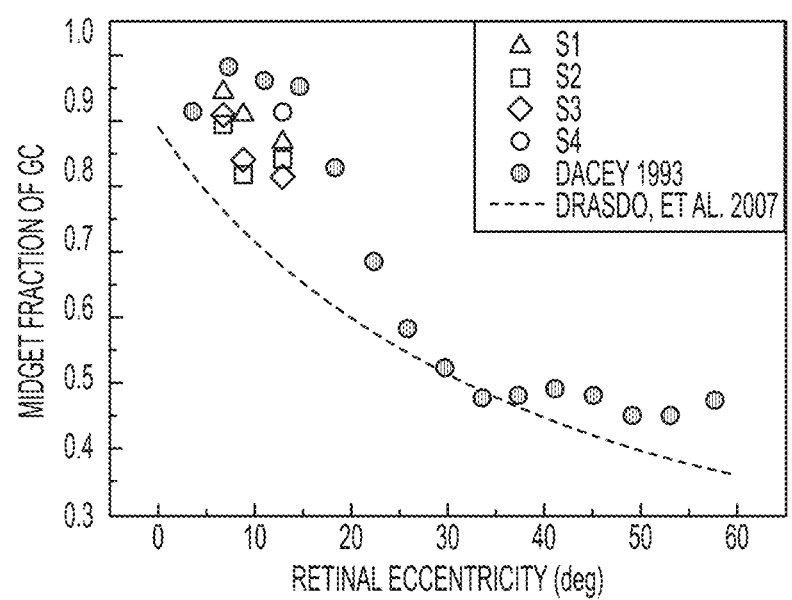
FIG. 36 is a plot of midget fraction of GC versus retinal eccentricity for four subjects.

FIGS. 34A-D depict properties of soma size, reflectance, and pooling of cone signals. In FIG. 34A, representative GCL soma size distribution (S4) is depicted by retinal eccentricity. In FIG. 34B, average GC soma diameter is shown obtained by Gaussian fits to the four subjects in temporal retina with measurements reported in the literature for humans. The error bars denote ±1 standard deviation unless labeled with an r to denote minimum-to-maximum range. M and P denote midget and parasol cells. Labels along x axis report retinal location of measurement—fm (foveal margin), pm (papillomacular), pr (peripheral retina). FIG. 34C shows representative reflectance of 637 GCL somas at 12-13.5° temporal to the fovea in subject S4. The line represents a linear regression curve. In FIG. 34D, mRGC-to-cone ratio for four subjects is plotted with Watson's histology-based model for humans and fovea ratios (see Watson, A. B. (2014). A formula for human retinal ganglion cell receptive field density as a function of visual field location. Journal of Vision, 14(7), 1-17. https://doi.org/10.1167/14.7.15).

A very small fraction of GCL cells (21 of 32,469 counted) at 1.5-3°, 3-4.5°, 6-7.5°, 8-9.5°, and 12-13.5° temporal to the fovea in the four subjects had giant somas (J cells), defined as a diameter greater than 26 µm. All but one of the giant somas were observed at the two largest retinal eccentricities, consistent with the reported distribution of giant cells whose frequency begins near this eccentricity range and peaks in the midperipheral retina. The largest had a diameter of 30.8 µm, almost exact in size to the 31-µm "giant" monkey GC Polyak used from his histology to illustrate this class.

GCL Soma Reflectance

No reports on the reflectance properties of individual GCL somas are known. In the development of the present disclosure, it was discovered that larger somas are generally more reflective (amplitude/pixel measured at soma center) than the smaller ones, a significant difference ($P<0.001$) in all subjects at all locations. This property is illustrated in the reflectance scatterplot of FIG. 34C that shows an average increase of 70% over the soma size range. Variation in reflectance must point to underlying differences in soma composition as measurements were made internal to somas that were selected from the same volume and narrow depth plane (14 µm). The latter avoided the influence of focus and other optical variations. Note that this approach parallels that commonly used to quantify reflectance variations of cone photoreceptors imaged with AO-flood, AO-SLO, and AO-OCT. The measured variation in soma reflectance suggests a method for distinguishing GC subtypes based on soma composition. Reflectance may prove especially useful in studying central retina where GC subtype is difficult to establish based on soma size.

GC Soma Subtypes

From histology of excised tissue, it is known that parasol GCs generally exhibit larger somas than midget GCs (mGC), and this size difference increases with distance from the fovea. The present disclosure confirms and extends that observation in living eyes by showing that the size distribution exhibits an increasingly positive skewness with retinal eccentricity (Pearson's moment coefficient increased from 0.53 to 1.45) and becomes bimodal for retinal eccentricities greater than 6°. To test whether these two modes represent the two primary subtypes of GCs in the macula (midget and parasol), two Gaussians were simultaneously fit to the bimodal distributions and the expected contribution of displaced amacrine cells were subtracted from the lower-diameter mode. When averaged across all subjects, the fractions of cells falling into the lower-diameter mode were 91%, 85%, and 86% for eccentricities of 6-7.5°, 8-9.5°, and 12-13.5°, respectively. These estimates fall between the fractional estimates of mGCs of prior research depicted in FIG. 36, and the size distributions of the present data fall within the range reported for midget and parasol somas in the human literature (see FIG. 34B). It may be concluded from these observations that single-scatter imaging is capable of resolving and distinguishing the two primary subtypes of GCs that form parallel visual pathways through the optic nerve to visual centers of the brain based on three fundamental soma features: size, density, and reflectance.

GC Soma Density

Histologic studies show that the spatial density of GC somas varies markedly across the retina—characterized by an elevated ring of densely packed, stacked somas surrounding the fovea—and across subjects. To determine the density in the subjects of the present disclosure, soma counts (41,506) from 24 of 26 imaged locations were used and, as before, amacrine population estimates from the literature were subtracted. FIG. 30 shows that the soma density distribution parallels that from histology, peaking at 3-4.5° with a sharp monotonic decrease toward the fovea and a gradual one away from it. Higher densities were found in nasal retina, also consistent with histologic studies. No significant difference was found for retinal eccentricities greater than 6° ($P=0.11$-$0.89$). At lower retinal eccentricities, our peak densities were smaller than histologic estimates with means and standard deviations of $19,162\pm2,087$ somas per mm$^2$ and $26,895\pm4,899$ somas per mm$^2$, respectively, a significant difference ($P=0.011$). While part of this difference can be attributed to the coarse 1.5°×1.5° sampling window, repeating the analysis using a smaller 0.17°×0.1° window and a counting protocol consistent with that of prior art research still yielded lower densities. No evidence of a scaling discrepancy was observed nor that obstructions such as vasculature or other cellular structures within the GCL masked the underlying somas and caused undercounting. Somas were evident across the entire GCL thickness, and the 790-nm wavelength of the AO-OCT of the present disclosure is minimally absorbed by retinal tissue. Thus, the discrepancy between the present density results and those from histology remains an open question, compounded by the small sample sizes in both studies.

GC Projection onto Cone Photoreceptors

Single-scatter imaging with AO-OCT enables the measurement of physical parameters in the living human retina that are fundamental to the structure and function of GCs. As an example of elucidating GC function in retinal neural circuitry, the present density measurements were used to derive individualized estimates of the pooling of cone signals by GC dendritic fields. Pooling of cone signals via intermediate bipolar cells is an anatomical necessity (because cones outnumber optic nerve fibers) that imposes fundamental limits on vision. mGCs in particular are important in determining visual acuity, yet histological estimates of the extent of their receptive fields and the number of mGCs that service each cone vary widely in the literature. In the human fovea, the reported range of mGC-to-cone ratio is large (0.9-3.4), requiring profoundly different numbers of ON-center and OFF-center mGCs to encode the foveal image. To derive an estimate of this ratio from the present in vivo AO-OCT data, the present measured GC coordinates were projected onto the measured cone photoreceptor coordinates for the same subject. GC retinal eccentricity ranges of 1.5-3°, 3-4.5°, 6-7.5°, 8-9.5°, and 12-13.5° were estimated to project to cone retinal eccentricities of 0.35-1.2°, 1.2-2.6°, 4.5-6.5°, 7.1-8.9°, and 11.7-13.3°. Cone densities in these eccentricity ranges (52,882, 34,178, 12,375, 9,728, and 6,602 cells per mm$^2$) were normal, with only one location (0.35-1.2°) statically lower ($P<0.05$) than the histologic measurements of prior research. The average mGC-to-cone ratios at these cone locations were 1.60, 1.12, 0.98, 0.72, and 0.52. As shown in FIG. 34D, the present ratio measurements are consistent with Watson's recent histology-based model, differing by 6%, 21%, 10%, 0.2%, and 4.1%, respectively. The present fovea ratio of 1.60 supports the view that the vertical pathway through the fovea connects two mGCs to one cone, allowing one to be ON center and the other OFF center. Individual differences, however, are notable with ratios across the four subjects varying by 9-70% [(max−min)/avg] depending on retinal location. This variation should affect visual resolution in these eyes as fundamental limits are imposed by the sampling of cone photoreceptors and mGCs. These limits may be tested by accounting for both.

Observing GCL Somas Under Thick NFL and at Foveal Rim

Figure 37:
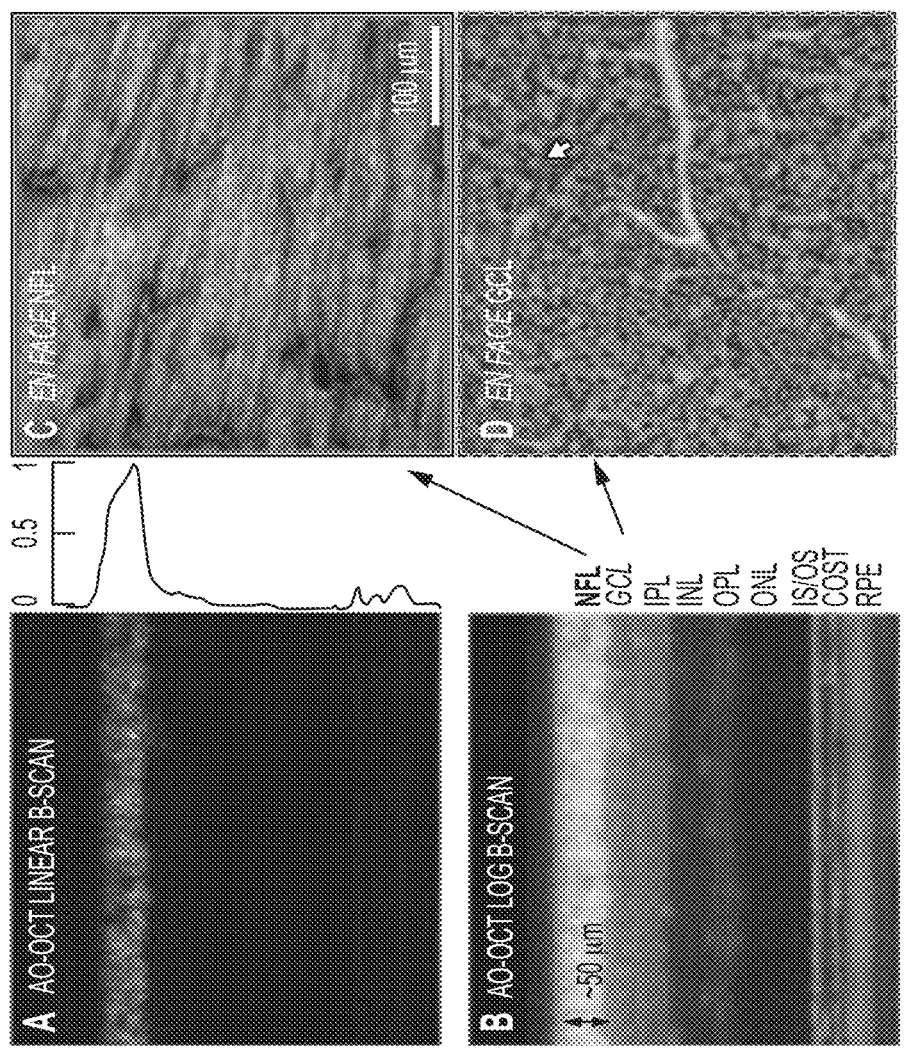
FIG. 37 provides images of an AO-OCT linear amplitude B-scan, a lob B-scan, and en face images of the NFL and GCL.

As shown in cross section and en face in FIG. 37, the NFL at 8-9.5° nasal (50 µm thick) approaches the thickest in the macula. It densely covers the entire volume image, and its peak amplitude reflectance is 6.5 times greater than that of the underlying GCL somas, a difference that is best appreciated by the cross-sectional image displayed in the figure on a linear, as opposed to logarithmic, scale. Despite this thick, brightly reflecting layer that lies immediately above the somas, the soma mosaic can be extracted as evident in the en face GCL image in the same figure. The arrow points to an individual soma.

Figure 38:
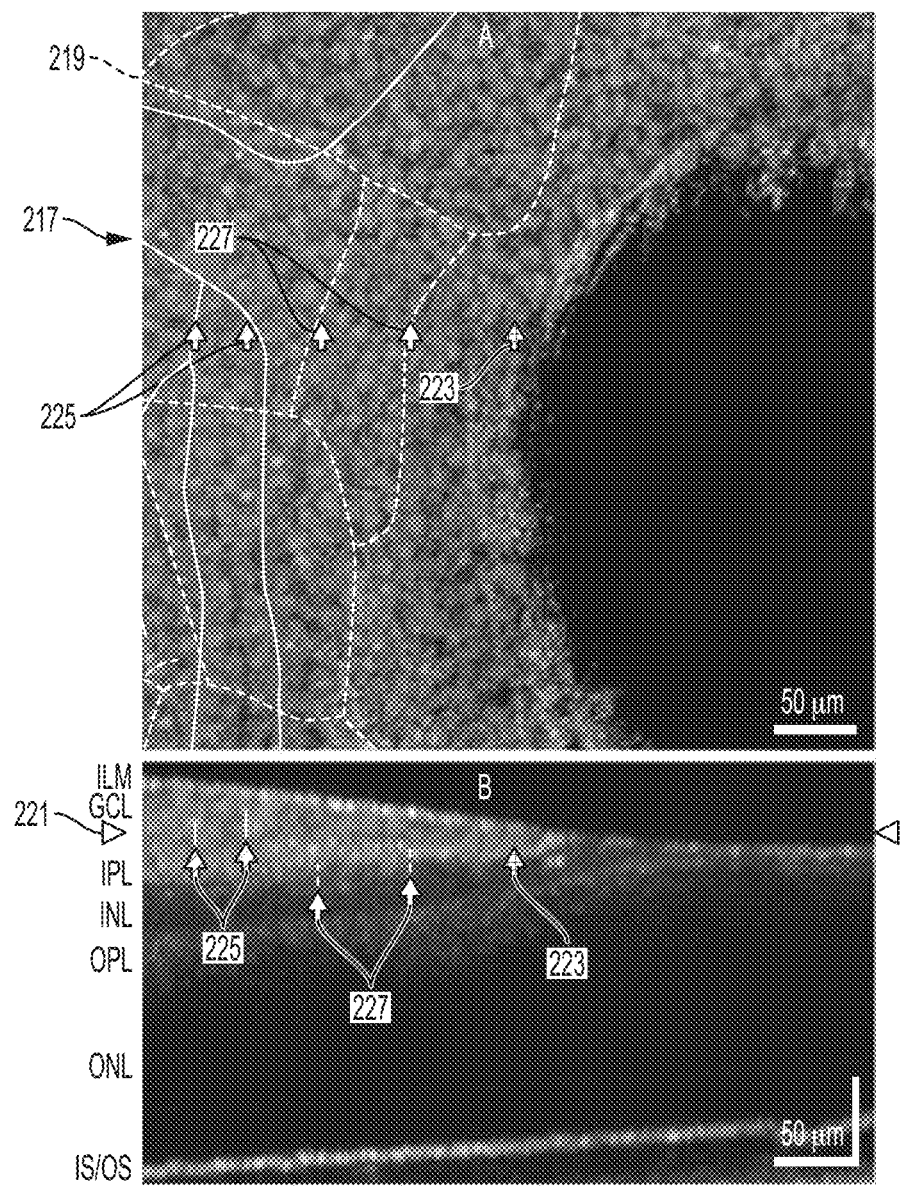
FIG. 38 provides images of a superimposition of three en face projections and a corresponding B-scan.

In contrast, close to the foveal center where the NFL is absent, the 0.35-1.85° retinal patch of S1 (see FIG. 38) reveals that GCL somas extend all of the way to the foveal rim of the GCL where they abut the ILM. FIG. 38 shows an arrangement of GCL somas and retinal vasculature at the foveal rim. The soma mosaic extends into the foveal avascular zone in this AO-OCT volume acquired at 0.35-1.85° temporal to the fovea in subject S1. The upper portion of the figure depicts a superposition of three en face projections extracted from the volume: one at the posterior side of GCL that captures the single row of somas at the foveal rim (grayscale image), one at the GCL vasculature (lighter image 217), and one at the IPL vasculature (darker image 219). The bright vertical striations at the GCL foveal rim are likely part of the ILM. The lower portion of FIG. 38 shows the corresponding B-scan that aligns to the five arrows in the upper en face view, showing the depth locations of the GCL somas and the retinal vasculature. The arrowheads 221 located outside the B-scan indicate the retinal depth at which the en face GCL image in the upper portion of the figure was extracted. The arrows 223 in both images point to the GCL soma that is closest to the foveal center in the selected B-scan. Arrows 225 point to the blood vessels located in GCL. Arrows 227 point to the blood vessels located IPL.

Presumably, the GCL somas that extend all the way to the foveal rim of the GCL where they abut the ILM are most critical for visual acuity as they are thought to project to photoreceptors at the foveal center. Prominent in the en face image is the extension of the soma mosaic into the foveal avascular zone, defined by the innermost ring of retinal capillaries encircling the fovea. In both subjects imaged at this location (S1 and S4), GCL somas did not extend more than 100 µm, consistent with the general rule for mammals that metabolically active cells should not be more than this distance to preserve molecular exchange via diffusion. This suggests that capillary dropout along the innermost ring, as for example occurs in diabetic retinopathy, is likely detrimental to these critical GCs, according to the present disclosure, can now be monitored in these patients as the disease progresses.

Visualizing GCs and Other Neurons Across the Retina

While the analysis of the principles of the present disclosure was confined to the horizontal meridian of the macula, the measurements have broader significance given the common neural layering of the retina across the posterior pole and radial symmetry of the macula about the fovea. Given these commonalities, the present methods should allow observation of GCL somas anywhere in the macula and beyond, whether stacked on each other (see FIGS. 32A-D and 33), lying beneath a thick and highly scattering NFL (see FIG. 37), or aggregated at the foveal rim where the smallest and closest-packed GCL somas are found (see FIG. 38).

Figure 39:
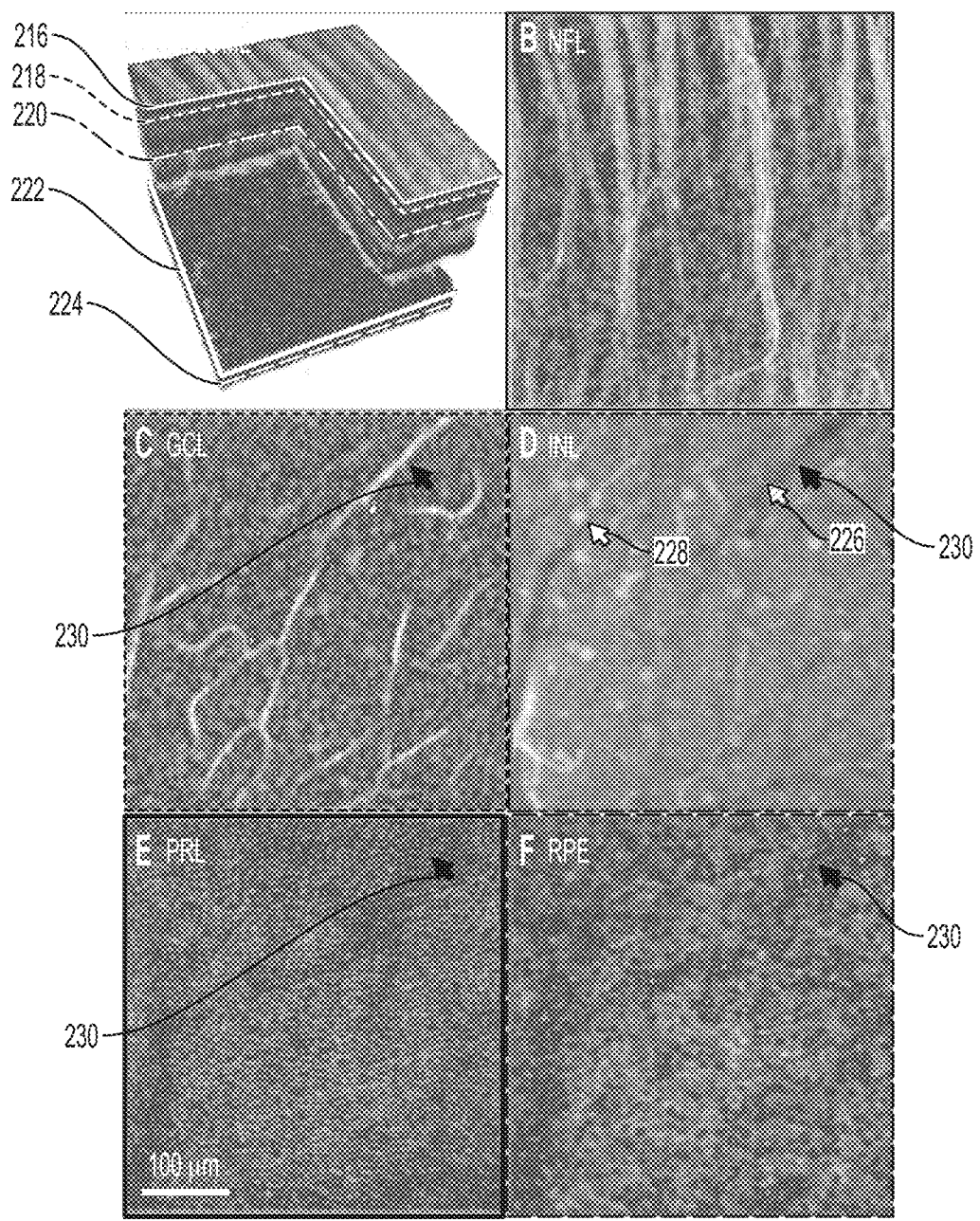
FIG. 39 provides images of cells at different depths in the same retinal patch of a subject.

Although GCL somas are emphasized in the present disclosure, the images also provide detailed views of nerve fiber bundles and GC axons that form them. In general, the AO-OCT methods of the present disclosure hold promise for visualizing cells across all retinal layers and, thus, exposing the anatomical substrate for neural processing of visual information. FIG. 39 illustrates this capability, showing cells extracted from different depths [NFL to retinal pigment epithelium (RPE)] in the same retinal patch.

Referring to FIG. 39, image A depicts a three-dimensional perspective of registered and averaged AO-OCT volume with lines denoting retinal depths at which the en face images B-F were extracted. Line 216 corresponds to image B, line 218 corresponds to image C, line 220 corresponds to image D, line 222 corresponds to image E and line 224 corresponds to image F. Image B depicts the individual NF bundles. Image C shows GCL somas (19,162 cells per $mm^2$). In image D, suggestive somas of bipolar (arrow 226) and displaced GCs (arrow 228) are identified near the IPL interface. Image E shows cone photoreceptors (16,341 cells per $mm^2$) and image F shows RPE cells (4,893 cells per $mm^2$). Arrows 230 in images C-F indicate the same blood vessel and its shadow. The en face images were extracted from volumes acquired at 3-4.5° retinal eccentricity with system focus shifted axially to maximize sharpness of the cell layer of interest.

In the images of FIG. 39, the types and densities of cells that compose each layer can be discerned. Interestingly, the inner nuclear layer (INL) image depicts a fine mesh of tightly packed, small (5-µm diameter), faint structures suggestive of bipolar somas and sparse, large (18-µm diameter), bright structures suggestive of displaced GC somas.

By imaging tens of thousands of GCL somas in four subjects, the research behind the present disclosure has demonstrated a path for visualizing and quantifying these elusive cells as well as other transparent neurons and cellular structures in the living human retina. While application of this method to diseased eyes is apparent, there is also optimism that the methodology can be improved further, for example, to characterize the dendritic morphology and soma organelle pattern that are more definitive cues of retinal cell type. Such characterization might be possible using the complex field recorded by AO-OCT to map the physiological dynamics of these cellular compartments.

Materials and Methods

Subjects

Four subjects, ranging in age from 24 to 50 y (S1=24, S2=26, S3=47, and S4=50 y old) and free of ocular disease, participated in the experiments. All subjects had best corrected visual acuity of 20/20 or better and a spherical equivalent refraction between 0 and −2.5 diopters. All had normal intraocular pressure (IOP), performance on perimetry, and appearance of optic disk and fundus. The one exception was S4 who had a history of elevated IOP (range 20-22), but normal otherwise. Eye lengths ranged from 23.27 to 25.40 mm as measured with the IOLMaster (Zeiss), and were used to scale the retinal images from degrees to millimeters.

Experimental Design

The subject's eye was cyclopleged and dilated with tropicamide 0.5%. The eye and head were aligned and stabilized using a bite bar mounted to a motorized XYZ translation stage. Images were acquired with the present AO-OCT system with system focus placed precisely at the GCL to maximize sharpness of GCL somas. Correct placement was realized by optimizing brightness of the GCL using the real-time displayed B-scan (cross sectional)

images and sharpness of the NFL vasculature in the en face images. AO-OCT volumes were acquired on the subjects at 10 macular locations along the horizontal meridian that bisected the fovea. The five locations (1.5-3°, 3-4.5°, 6-7.5°, 8-9.5°, and 12-13.5°) temporal to the fovea were imaged in four subjects and the four (1.5-3°, 3-4.5°, 6-7.5°, and 8-9.5°) nasal to it were imaged in one. An extreme foveal location at 0.35-1.85° temporal was imaged in two subjects. For each retinal location, 10-15 AO-OCT videos (each ~4 s in duration) were acquired over ~10 min. Each video consisted of 11 volumes. The volumes covered a 1.5°×1.5° field of view of the retina, and A-scans were sampled at 1 μm per pixel in both lateral dimensions. Fast A-scan and B-scan rates of 500 KHz and 1.1 KHz reduced, but did not eliminate, eye motion artifacts.

Images were also acquired of other retinal cells by focusing the system to the desired depth that maximized cell sharpness. This included imaging cone photoreceptors along the horizontal meridian that projected to the GCs at 1.5-3°, 3-4.5°, 6-7.5°, 8-9.5°, and 12-13.5°. Commercial (Spectralis; Heidelberg Engineering) spectral-domain OCT and SLO images were acquired on all subjects and covered the retinal locations imaged with AO-OCT.

Postprocessing of AO-OCT Volumes

Volumes were reconstructed, dewarped to correct nonlinearities in the fast-axis scan pattern, registered in three dimensions to correct eye motion artifacts, and averaged to increase signal to noise. Images of GCL somas are difficult to register with conventional 2D strip-wise registration methods owing to the high translucency of these cells. This obstacle was overcome by using a custom 3D strip-wise registration algorithm that operated on individual fast B-scans, thus using all available information in the volumes and precluding the need of a GC signal. The registered and averaged volumes were used for all further analyses. Displayed volumes are shown as log intensity following the OCT literature, unless specified otherwise.

Quantifying Soma Size and Size Distribution

The diameter of each GCL soma was computed based on an en face (XY) view of the soma and the 3D coordinates of its center using software developed in MATLAB. The en face view was a three-pixel (2.82 μm) projection in depth of the reflectance distribution around the soma center. A circumferential average about the soma center in the en face view resulted in a 1D reflectance trace. Cell diameter was defined as twice the distance between the cell center and the minimum in the reflectance trace.

For each subject and retinal eccentricity, a single Gaussian function was fit to the soma size distribution where it appeared unimodal (for retinal locations up to 6°) and two Gaussian functions where it appeared bimodal (for retinal locations at and greater than 6°). The Gaussian fits were used to quantify the peak and range of soma diameter and the fraction of each mode.

Quantifying Soma Density

GCL soma centers were projected onto an en face plane from which soma densities were determined by two different methods. The first used Voronoi mapping of the soma mosaic, a mathematical construct widely used for quantifying cell association in retina tissue. For this method, soma density was defined as the ratio of total number of Voronoi cells to total area of the Voronoi cells. This approach avoided edge effects of the 1.5°×1.5° imaging window and blood vessels that can generate errors in the density count. The second method followed traditional histologic approaches. Specifically, cell centers were counted that fell within a small 0.17°×0.1° sampling window free of vasculature. The window size, number of windows, and counting protocol followed that of prior research, except the present research relied on cell centers as opposed to nucleolus locations, which could not be detected in the present images.

GCs were not distinguished from displaced amacrine cells, which represent 1-22% of the soma population in the GCL from central fovea to 13.5°. To facilitate comparison, we used displaced amacrine population values from the literature to offset the count.

Determine mGC-To-Cone Ratio

The GC coordinates measured with AO-OCT were projected onto the cone photoreceptor coordinates, also measured with AO-OCT, by applying the displacement function given by equation 5 of Watson for the horizontal meridian. This function accounts for the lateral displacement of GCs, which can exceed 600 μm (~2°) depending on retinal eccentricity and is caused by the lateral extension of photoreceptor axons and connections of the bipolar cells. The projection took into account annular scaling between the GC and cone layers, and was adjusted for the proportion of GCs that are midget. For GCs at retinal eccentricities of 6-7.5°, 8-9.5°, and 12-13.5° where the GC size distribution was bimodal, the lower-diameter mode was used to estimate the mGC fraction. Nearer to the fovea where bimodality was not observed, the fractional estimate of 89.3% was used.

The inner retina is critical for visual processing, but much remains unknown about its neural circuitry and vulnerability to disease. A major bottleneck has been our inability to observe the structure and function of the cells composing these retinal layers in the living human eye. Here, we present a noninvasive method to observe both structural and functional information. Adaptive optics optical coherence tomography (AO-OCT) is used to resolve the inner retinal cells in all three dimensions and novel post processing algorithms are applied to extract structure and physiology down to the cellular level. AO-OCT captured the 3D mosaic of individual ganglion cell somas, retinal nerve fiber bundles of micron caliber, and microglial cells, all in exquisite detail. Time correlation analysis of the AO-OCT videos revealed notable temporal differences between the principal layers of the inner retina. The GC layer was more dynamic than the nerve fiber and inner plexiform layers. At the cellular level, we applied a customized correlation method to individual GCL somas, and found a mean time constant of activity of 0.57 seconds and spread of ±0.1 seconds suggesting a range of physiological dynamics even in the same cell type. Extending our method to slower dynamics (from minutes to one year), time-lapse imaging and temporal speckle contrast revealed appendage and soma motion of resting microglial cells at the retinal surface.

Turning now to further developments of the present disclosure, in a further embodiment the principles described herein are further leveraged to learn more about the physiological properties of cells in the living human retina. As indicated above, the inner retina is responsible for a significant proportion of the visual processing that occurs in the retina. However, much remains unknown about the mapping and performance of this neural circuitry and its vulnerability to disease, primarily because of the inability to observe these highly translucent retinal layers at the cellular level in the living human eye. Furthermore, a complete description of circuit performance requires physiological as well as structural information. As explained above, AO-OCT has overcome the translucency barrier, enabling visualization of individual retinal neurons-most notably ganglion cells (GCs)—in living human retina. This success shows promise for development of biomarkers for earlier detection, diagnosis, and treatment monitoring of inner retinal pathologies, but does not capture the physiological properties of these cells. In this embodiment of the present disclosure, AO-OCT is used to individuate retinal cells (namely ganglion and retinal microglial cells) and then a post processing technique based on amplitude autocorrelation and speckle contrast is used to extract temporal dynamics down to the level of individual cells.

Methods

Imaging System

The AO-OCT system described above was used in this study. In this embodiment, the fiber-based system operated at a center wavelength of 790 nm with a theoretical axial resolution of 4.7 µm in tissue (n=1.38) and lateral resolution of 2.4 µm. The system's 2-camera mode was used to achieve an image acquisition speed of 500K A-scans/s. System focus was placed in the ganglion cell layer (GCL) to maximize signal strength and sharpness of this layer. Optical power delivered to the eye was below 430 µW, which is within the ANSI safety limit.

Data Acquisition and Processing

AO-OCT volume videos were acquired at 12° temporal to the fovea in a healthy subject with no known retinal pathologies. At this eccentricity, GCL somas at the macular edge are larger in size and variation, making it easier to compare cells' structure and function. Each video contained 11 to 12 volumes acquired at 0.18 s interval (5.3 vol/s) or 0.41 s interval (2.4 vol/s) and time stamped. In post-processing, AO-OCT volumes were registered to a reference volume that was manually selected to minimize motion artifacts. Registration achieved subcellular-level accuracy and was accelerated using a newly developed 3D registration algorithm. Further post-processing characterized changes of the inner retinal layers and cells occurring at slow (minutes to one year) and fast (≤seconds) time scales.

To characterize fast temporal dynamics, a temporal auto-correlation analysis was performed on the volume videos and determined time constants, T, for selected layers: nerve fiber layer (NFL), GCL, and inner plexiform layer (IPL). The analysis was also applied separately to GCL soma interiors, thus capturing only intracellular dynamics and avoiding contributions from adjacent structures in the same layer, e.g., glial processes, vasculature and extracellular space. Development of the correlation analysis was guided by dynamic light scattering theory and followed a three step process: (1) remove time invariant components, $$A'(\vec{r},t) = A(\vec{r},t) - \langle A(\vec{r},t) \rangle_T, \quad (1)$$

where $A(\vec{r},t)$ is the measured reflectance amplitude at pixel location r in the AO-OCT volume image that was acquired at time t.

$\langle A(\vec{r},t) \rangle_T$, is the temporal average of the measured reflectance amplitude. Next, (2) compute auto-correlation coefficients, ρ, for $A'(\vec{r},t)$ at every time point with time differences, Δt, up to 2.25 s, $$\rho(\vec{r}, \Delta t) = \text{corr}(A'(\vec{r},t), A'(\vec{r}, t+\Delta t)). \quad (2)$$

Unfortunately, this standard expression for auto-correlation is sensitive to pixel-correlated noise in the AO-OCT image, thus contributing an error in the estimated time constant, T. To correct for this error, a different mathematical expression for ρ was used based on a disattenuated correlation estimate. To do this, the noise variance—which was computed in the vitreous portion of the AO-OCT image where the noise dominates signal—was subtracted from the sample variance to obtain an improved estimate of the sample variance. Because the noise is decorrelated, the disattenuated correlation can be estimated using the improved variance estimate inserted in the denominator of $$\rho(\vec{r}, \Delta t) = \frac{\text{cov}(A'(\vec{r},t), A'(\vec{r}, t+\Delta t))}{\sqrt{(\text{var}A'(\vec{r},t) - \text{var}N)(\text{var}A'(\vec{r}, t+\Delta t) - \text{var}N)}}, \quad (3)$$

where N is the pixel-correlated noise amplitude measured in the vitreous. Finally, (3) estimate the time constant, T, by computing the temporal sum of averaged coefficients from Equation (4), in this way accounting for possible non-exponential decay, $$\tau(\vec{r}) = \int \bar{\rho}(\vec{r}, \Delta t) d\Delta t. \quad (4)$$

To characterize slow temporal dynamics, temporal speckle contrast was used and the efficacy of the method was investigated by testing it on microglial cells at the inner limiting membrane. A time-lapsed image was generated for each time interval (0-4 min; 4-8 min; 8-13 min.) and motion quantified per pixel using temporal speckle contrast, defined here as the standard deviation of the reflectance amplitude divided by its mean to cancel the reflectivity dependence (~0.5 if speckles are fully developed):

$$C(\vec{r}) = \frac{\sqrt{\langle (A(\vec{r},t) - \langle A(\vec{r},t) \rangle_T)^2 \rangle_T}}{\langle A(\vec{r},t) \rangle_T}. \quad (5)$$

Results

Fast Temporal Dynamics of Inner Retinal Layers and Individual GCL Somas

FIGS. 40A-D demonstrates the cellular details of the inner retina layers that can be extracted from a single registered and averaged AO-OCT volume. In FIGS. 40A-D show en face images extracted at depths of the vitreous, NFL, GCL, and IPL, respectively, from the same registered and averaged AO-OCT volume image. The image was acquired at 12° temporal to the fovea. The en face images reveal individual GCL somas (FIG. 40C), nerve fiber bundles (FIG. 40B), and blood vessels (FIGS. 40B-D). FIG. 40E shows time correlation, computed from the AO-OCT volume videos, plotted for the three inner retinal layers—the NFL 232, the GCL 234 and the IPL 236. The error bars denote one standard deviation.

Clear delineation of GCL somas and micron-caliber nerve fiber bundles are evident in FIGS. 40C and 40B, respectively. Time correlation traces of these layers are shown in FIG. 40A, which reveals notable temporal correlation differences between the layers, suggesting differences in physiological activity. Corresponding time constants are 0.84 s (NFL), 0.50 s (GCL), and 0.69 s (IPL). Interestingly, GCL dynamics were ~40% faster than that of the NFL and ~28% faster than that of IPL.

Of course each layer is composed of numerous cellular structures, and therefore the reported time constants in FIG. 40E are aggregates across the corresponding layer. To assess dynamics of just neuron cell bodies, FIGS. 41A-E show the time constant of individual GCL somas, coded and superimposed on the corresponding reflectance amplitude image.

Figure 41A:
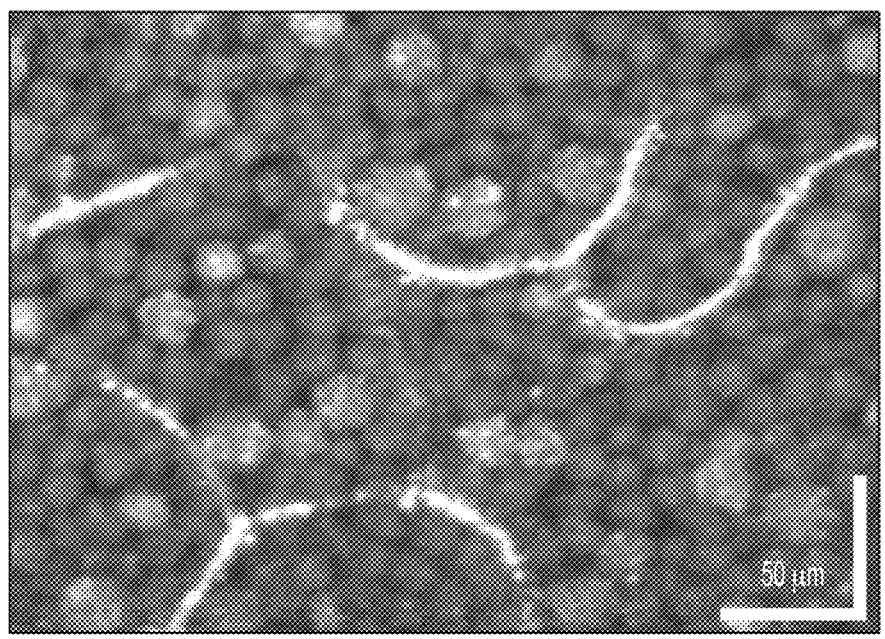
FIGS. 41A-E provide a registered and averaged en face image of the GC layer, the same image with superimposed correlation time constants, a histogram of the time constants, and graphs of soma reflectance and time constants.
Figure 41B:
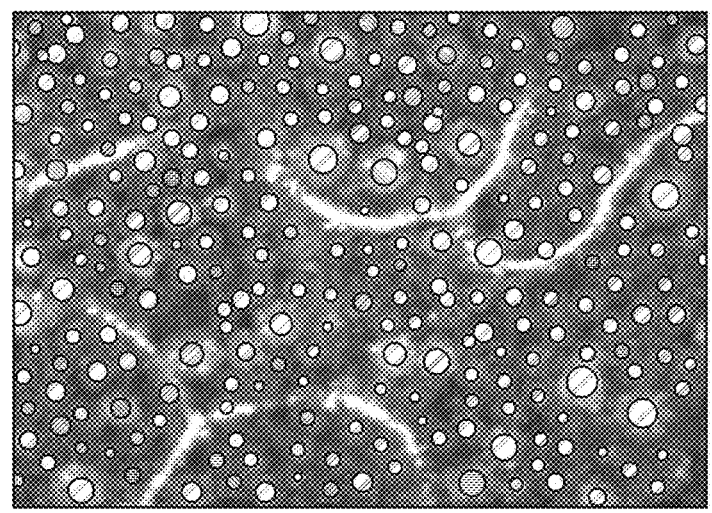

In FIG. 41A, a registered and averaged en face image of the GC layer reveals a contiguous mosaic of GCL somas disrupted only by capillaries. In FIG. 41B, correlation time constants were computed for the somas in FIG. 41A and superimposed as circles with fill patterns as defined in the histogram of FIG. 41C. FIG. 41D shows soma reflectance and FIG. 41E shows time constant, each plotted against soma size.

Figure 41C:
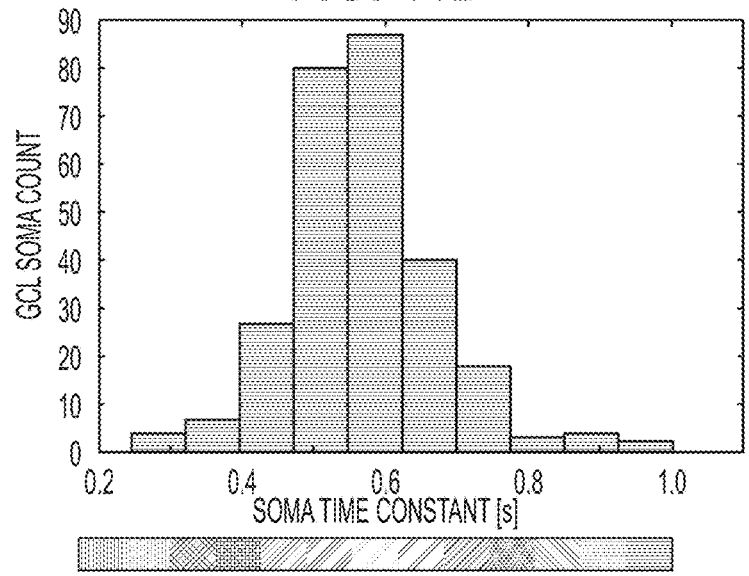
Figure 41D:
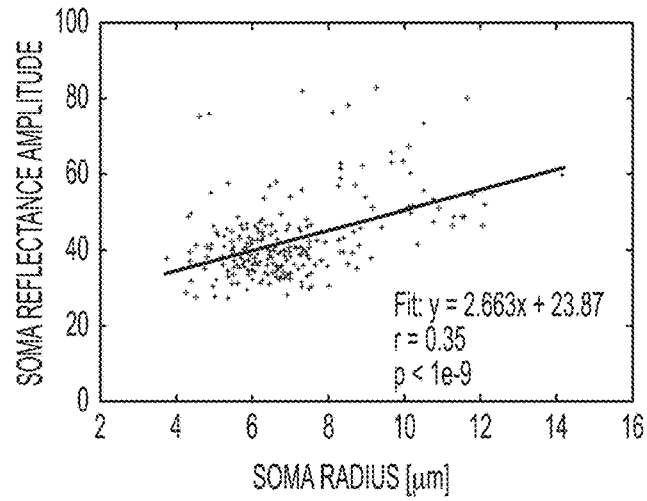
Figure 41E:
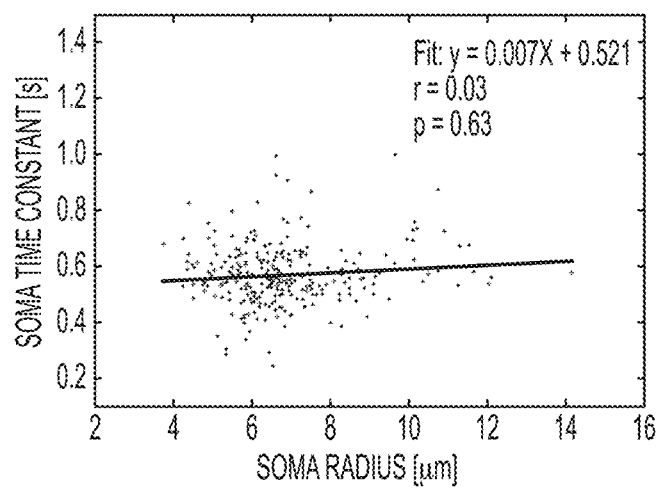

As seen in FIG. 41C, the time constant distribution is nearly unimodal with a mean and standard deviation of $0.57 \pm 0.1$ s. This is slightly longer than that of the entire GC layer (0.50 s in FIG. 40E), consistent with the expectation that removal of vasculature contributions—where speckle de-correlates quickly—should increase the time constant (reduce temporal dynamics). Furthermore, the >4× difference between the least and most active GCL somas suggests a wide range of physiological dynamics, perhaps indicative of different GC subtypes. Interestingly, the time constant was not significantly correlated with soma radius (Spearman, r=0.03, p=0.63), meaning smaller somas did not exhibit slower or faster dynamics compared to larger somas, at least over the temporal range that was tested (0.18-2.25 s). For comparison, a test was performed for a correlation between soma reflectance and soma size and a positive correlation was found (Spearman, r=0.35, p<1e−9), with larger somas generally more reflective than smaller somas. This correlation is consistent with previous findings.

Slow Temporal Dynamics of Microglial Cells

FIGS. 42A-F depict slow temporal dynamics of microglial cells and GCL somas that occur over time durations of minutes and one year. To facilitate visualization of cellular motion on these time scales, time-lapsed AO-OCT images of the same retinal patch and depth are color-coded, with colored pixels indicating cellular motion and white/black pixels indicating absence of motion.

Figure 42A:
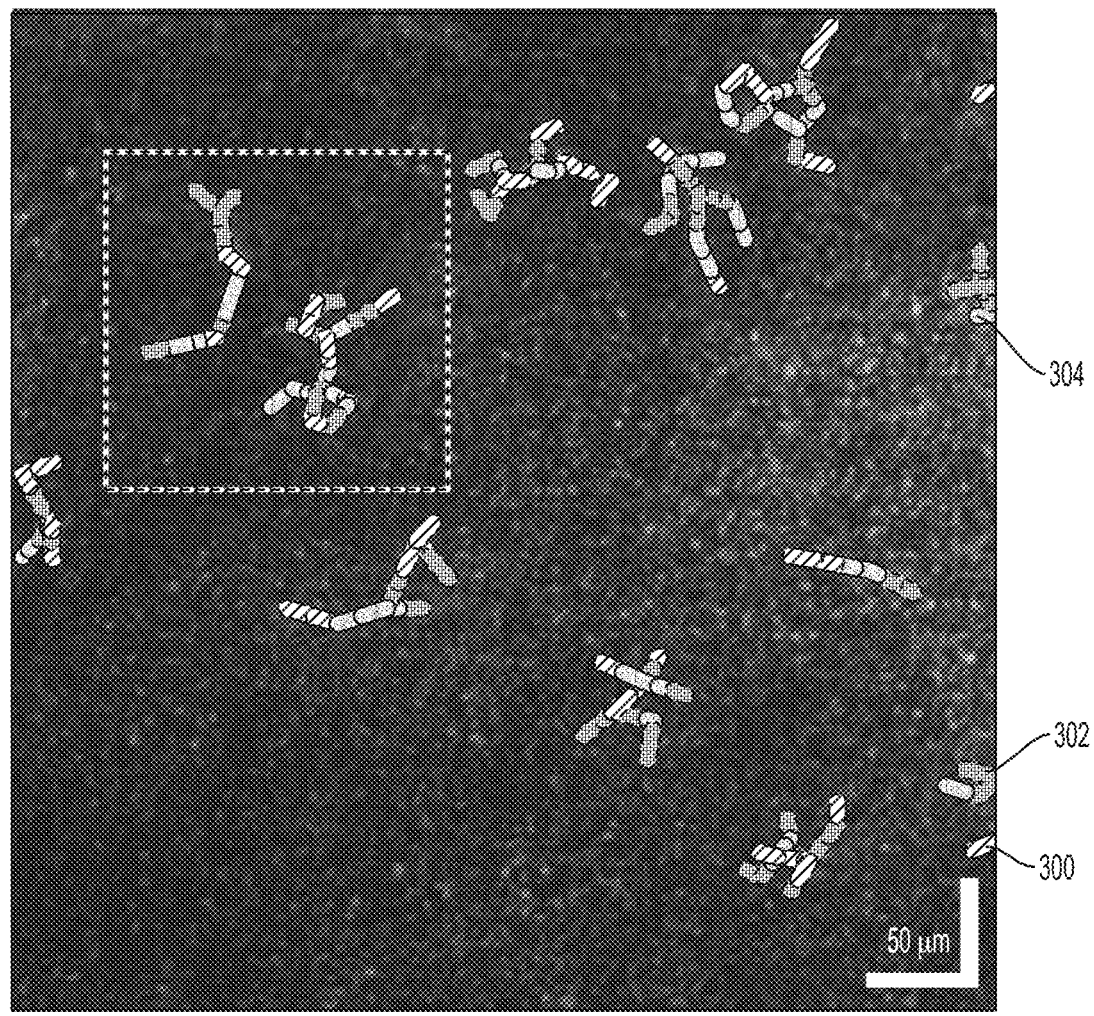
FIGS. 42A-F provide time lapsed AO-OCT imaging test results for slow temporal dynamics of microglial and ganglion cells.
Figure 42B:
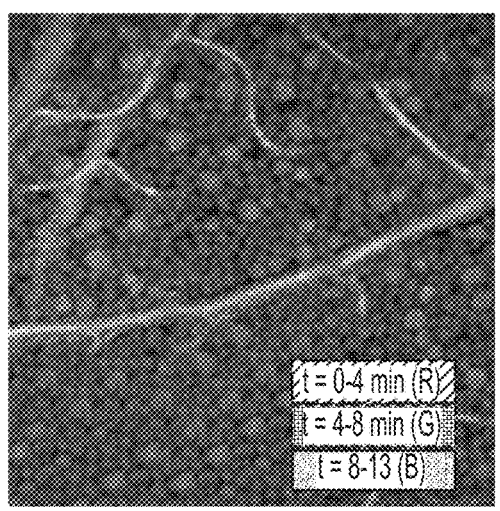

FIG. 42A shows composite en face images of microglial cells and FIG. 42B shows GCL somas constructed by assigning each RGB channel to an image acquired at a different time point as defined in FIG. 42B. Thus the different pixels in the images indicate time-lapsed changes. The red channel is shown as segments 300. The green channel is shown as segments 302. The blue channel is shown as segments 304.

Figure 42C:
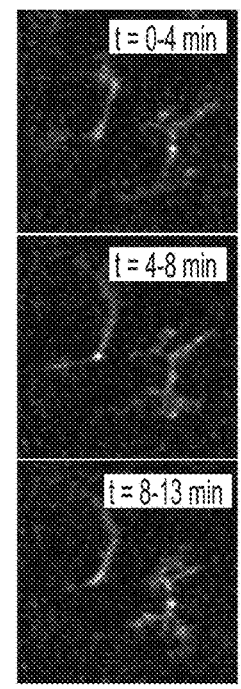
Figure 42D:
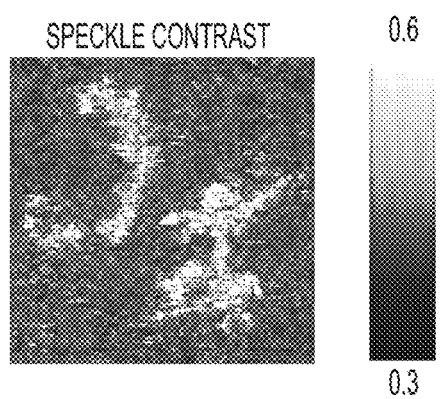

FIG. 42C provides a magnified view of two microglial cells enclosed in the box of FIG. 42A and color channels (i.e., time points) displayed separately further substantiates the movement of microglial somas and processes. FIG. 42D shows the cell motion in FIG. 42C quantified using the defined temporal speckle contrast metric. Composite en face images of FIG. 42E (microglial cells) and FIG. 42F (GCL somas) are constructed in the same way as FIGS. 42A and 42B except over a much longer time interval of one year as defined in FIG. 42F. All images were acquired at 12° temporal to the fovea.

Color changes over the course of several minutes in pixels associated with microglial somas and processes indicate extremely subtle movements of these cells (see FIG. 42A). These changes are particularly striking in the cell processes, consistent with the view that microglial cells are continuously probing their local microenvironment even when they appear to be "at rest." These changes are substantiated by a direct view of the time lapsed images presented sequentially in FIG. 42C and quantifying them with the defined speckle contrast metric. The metric clearly shows that changes are confined to the microglial soma and processes (see FIG. 42D). These dynamics, now observable in the living human retina, are consistent with previous ex vivo and in vivo experiments on fluorescence-labeled microglia in mice.

Figure 42E:
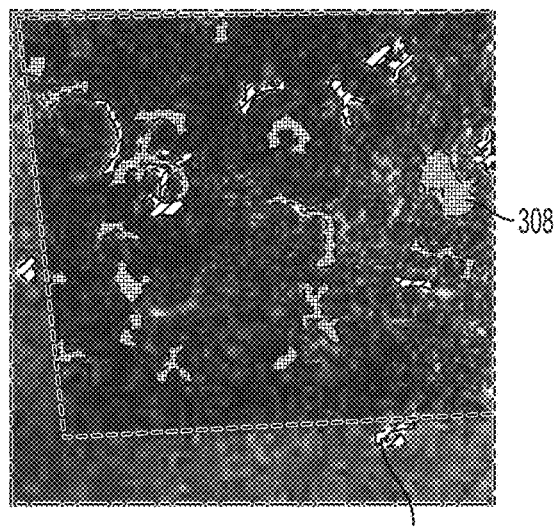

In contrast to these subtle changes that occur in microglial cells over minutes, vast changes occur over the time scale of a year (see FIG. 42E). Microglial cells in this patch of retina are completely rearranged, revealing them to be highly active at this time scale. This degree of activity is consistent with the scavenger role played by microglial cells. Being macrophages, the cells are believed to migrate across and through the retina, and as they have been implicated in the pathogenesis of numerous retinal diseases their numbers are believed to fluctuate as a function of retinal health. Using AO-OCT as described herein, these temporal changes can now be measured.

Figure 42F:
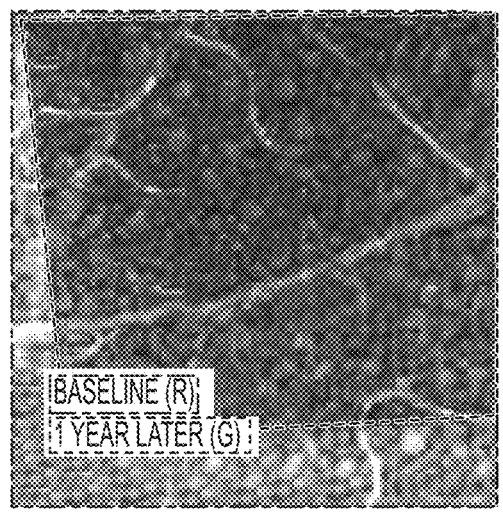

FIGS. 42B and 42F depict the application of the same method to the depth of the GCL layer within the same AO-OCT volumes. These images reveal no detectable changes in the GC layer over either minutes or one year. The method according to the present disclosure therefore indicates that the cellular composition of the GC layer is highly stable over these time scales.

Thus, the above-described embodiment provides a non-invasive method based on AO-OCT and novel post processing that can measure both structure and function of individual cells in the living human retina. The method was successfully applied to quantifying the temporal dynamics of the inner retinal layers (NFL, GCL, and IPL) and of individual cell types that are highly translucent (GCL somas and microglial cells). These results indicate that the method is highly sensitive and potentially capable of mapping functional aspects of neural circuitry in the living human retina and detecting the earliest cellular changes associated with disease onset.

Referring now to another embodiment of the disclosure relating to cone photoreceptor classification in the living human eye from photostimulation-induced phase dynamics, it should be understood that vision begins when photoreceptors capture photons and hyperpolarize. All photoreceptors respond to light, but response magnitude to a specific light depends on the photopigments contained in their outer segments (OSs). In most humans, each cone contains and is classified by one of three photopigments with different spectral sensitivities. The spatial arrangement and spectral sensitivities of these cone types fundamentally limit color vision. Most color vision anomalies are caused by absence or dysfunction of one or more cone types; these deficits can either be genetically inherited or acquired from disease or aging.

Human color vision has been extensively studied for centuries, but the placement of photoreceptors at the back of the eye has impeded direct physiological investigation. The proportions of cone types have been inferred using indirect and noninvasive methods such as psychophysics and electroretinography (ERG), but these methods lack the resolution to assess spatial arrangement of cone types and its variation across the retina. Direct ophthalmic imaging methods have recently been enhanced by the use of adaptive optics (AO) to correct ocular aberrations, permitting imaging of individual photoreceptors and bringing the study of color vision to the cellular scale. The trichromatic cone mosaic has been successfully mapped using AO-enhanced retinal densitometry to selectively bleach particular photopigments. However, a variety of factors necessitate high bleach levels by multiple light sources and repeated measurements to attain an adequate signal. These include low (≤0.4 log unit) and varied optical densities of cones, interference noise within cones, background noise from other reflective retinal tissue, and the similarity of M and L cone spectral sensitivity functions. These factors result in long experiments (ranging between 3-9 hours and 5 days) and uncertainties of 3.6%±1.6% in classification (average±SD of uncertainty of 20 eyes reported in four AO retinal densitometry studies). These shortcomings have limited the use of AO-enhanced retinal densitometry in color vision studies.

By contrast, the present approach uses nanometer-scale optical path length changes (ΔOPL) occurring inside photoreceptors during photoactivation—photoreceptor response to light—to identify cone spectral types with unprecedented sensitivity, accuracy, and efficiency. It achieves dramatically smaller uncertainties (<0.02%) compared to AO retinal densitometry and with notably shorter data acquisition times. The method achieves repeatability errors of 0.2-0.37%, which may capture classification performance better than uncertainty does but has not been reported in the classification literature. The method includes measuring the ΔOPL signature of cones in terms of an equivalent phase change by combining AO and phase-sensitive optical coherence tomography (AO-OCT). This combination yields sufficient resolution to reveal individual cone reflections in 3D and sufficient phase sensitivity to detect optical path length changes as small as 5 nm. The rapid image acquisition sampled phase at 3 KHz, permitting assessment and quantification of extremely transient phototransduction-related dynamics.

For this study, the AO-OCT system used a single light source, a superluminescent diode with central wavelength of 790 nm and bandwidth of 42 nm, for AO-OCT imaging and wavefront sensing. Nominal axial resolution of the system in retinal tissue (n=1.38) was 4.7 µm with depth sampling at 0.98 µm per pixel. The AO system consisted of a custom Shack-Hartman wavefront sensor and a deformable mirror (DM97; ALPAO) that dynamically measured and corrected ocular aberrations across a 6.7-mm pupil of the subject's eye. This resulted in a diffraction-limited lateral resolution of 2.4 µm. Image detection was based on a custom quad-spectrometer that was used in its 4-camera mode that acquired A-scans at 1 MHz and laterally sampled the retina at 1 µm/pixel. The data stream from the AO-OCT system was processed and displayed real time to provide direct feedback. The system delivered <430 µW of power to the eye.

Figures 43A, 43B:
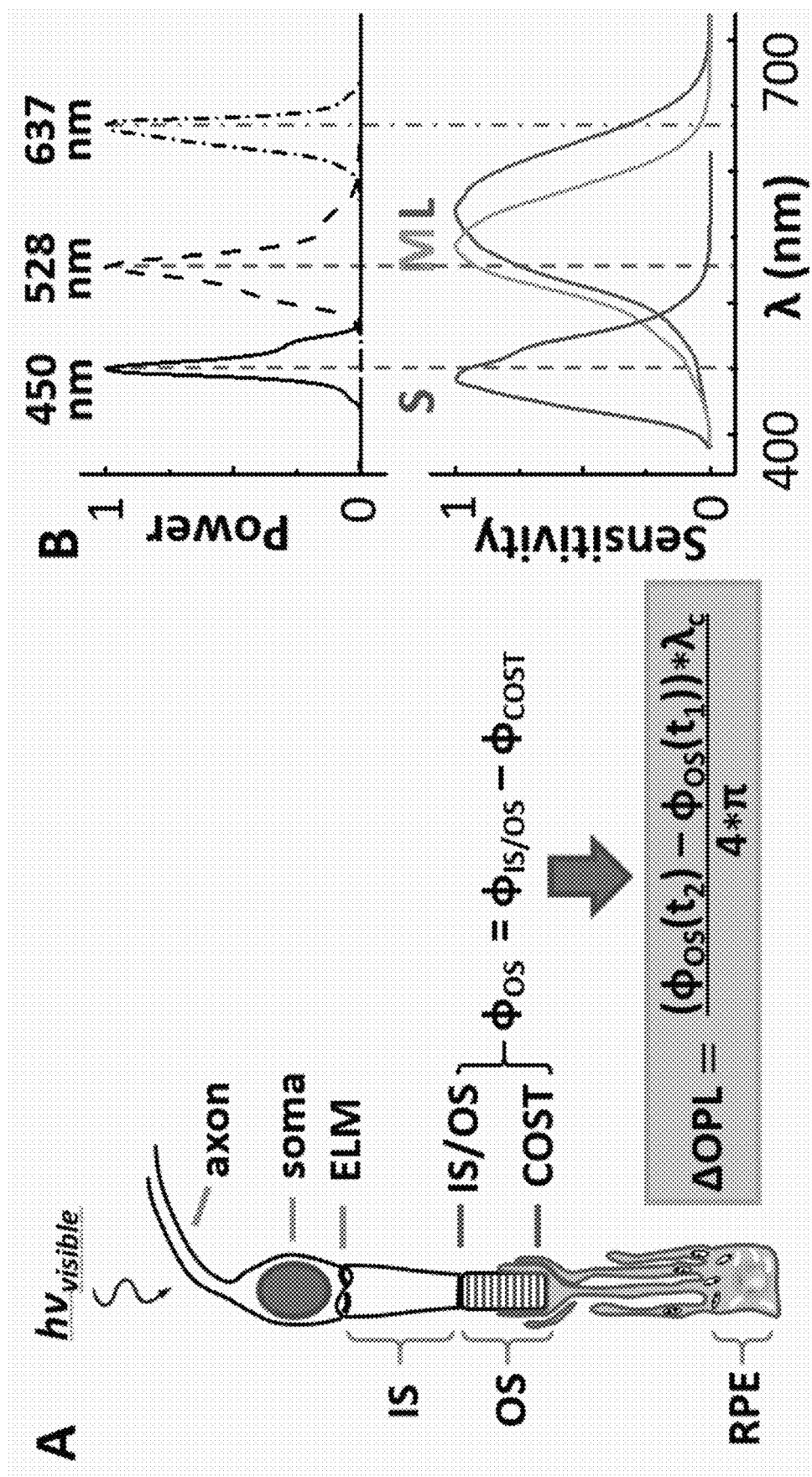
FIG. 43A is a schematic depicting the axon, soma, inner segment (IS) and OS of a cone cell, and the underlying retinal pigment epithelium (RPE) cell that ensheathes it.
FIG. 43B depicts a normalized spectra of the three light sources that stimulate the cones are shown with the normalized sensitivity functions of the three cone types that are sensitive to short—(S), medium—(M), and long—(L) wavelength light (31)

Three fiber-based LED sources (LEDMOD455, LED-MOD528, and LEDMOD625 from Omicron-Laserage, Germany) with spectra of (max±half width half height) 450±8 nm, 528±12 nm, and 637±12 nm, respectively, were used for stimulating cone photoreceptors. Light from the sources were combined and co-aligned with the AO-OCT imaging beam using dichroic beam splitters. Light from the sources formed a 7 mm beam at the eye pupil and illuminated a 2° retinal patch. Source spectra are shown in FIGS. 43A-B. These three wavelengths were selected as they cover a wide range of absorption efficiencies of the three cone types with normalized absorption efficiencies of S=0.96, 0.02, and 0; M=0.09, 0.92 and 0.04; and L=0.05, 0.75 and 0.3 for wavelengths of 450 nm, 528 nm and 637 nm, respectively. Ordering the absorption efficiencies by wavelength, it is determined that S>M>L (450 nm), M>L>S (528 nm), and S>M>L (637 nm). Maximum power at the cornea as measured with a spectrally broadband power meter (OPHIR NOVA II with PD300-BB-50 mW detector) was 220 µW (450 nm LED), 95 µW (528 nm LED), and 320 µW (637 nm LED). Timing uncertainty of the LED flash onset was (±SD) ±0.6 ms relative to the AO-OCT image acquisition. Rise and fall times of the LED flashes were 4 is (10% to 90% of flash's steady value), thus producing a pristine top hat profile.

The combined energy of the AO-OCT beam (<430 µW) and light stimulation flash (95 µW to 320 µW depending on source) were within safe limits established by the American National Standards Institute. The proportion of photopigment bleached by the stimulus was estimated using Equation 6 from Rushton and Henry, where p is the proportion of unbleached photopigment, I is the retinal illuminance, $Q_e$ is a constant that denotes the flash energy required to bleach p from 1 to $e^{-1}$, and $t_0$ is the time constant of pigment regeneration. Rushton and Henry estimated $Q_e$ and $t_0$ to be $2.4 \times 10^6$ td-sec and 120 sec. In this use, it was assumed that the photopigment was initially unbleached and approximated the spectral content of the stimulus source by its center wavelength.

$$-\frac{dp}{dt} = \frac{Ip}{Q_e} - \frac{1-p}{t_0}. \tag{6}$$

Both slow and fast temporal changes in the optical path length of cone OSs were extracted from the registered AO-OCT volumes. First, the phase difference, $\varphi_{OS}$, between the IS/OS and COST reflections of each A-line of the volume was computed as given by Equation 7

$$I_{OS} = I_{ISOS} I^*_{COST}, \varphi_{OS} = \angle I_{OS}. \tag{7}$$

where $I_{ISOS}$ and $I_{COST}$ are reflections in complex form containing intensity and phase. Both were averaged over a ±5 pixel (±5 µm) depth nominally centered on the reflection peaks in order to improve accuracy of the phase measurement. To extract the slow dynamics of the cones (which extended over seconds), 2D response maps were computed as the phase difference, $\Delta\varphi_{OS}^{(k,i)}$, between each volume and pre-stimulus volume of the same video:

$$\Delta I_{OS}^{(k,i)} = I_{OS}^{(k)} I_{OS}^{(i)*}, \Delta\varphi_{OS}^{(k,i)} = \angle \Delta I_{OS}^{(k,i)}. \tag{8}$$

where k is the index of all the volumes and i is the index of the subset that were acquired pre-stimulus. To improve signal to noise and number of cones tracked, all phase differences were referenced to the average of the pre-stimulus volumes:

$$\Delta I_{OS}^{(k,pre)} = \sum_{i=1}^{N} \frac{I_{OS}^{(k)} I_{OS}^{(i)*}}{N}, \Delta\varphi_{OS}^{(k,pre)} = \angle \Delta I_{OS}^{(k,pre)}. \tag{9}$$

Here N is the total number of pre-stimulus volumes. Next, non-cone pixels were removed from the response maps, $\Delta I_{OS}^{(k,pre)}$, by thresholding pixel amplitudes and then averaging over all non-zero pixels to obtain a single response value. Thus each video generated a single 1D response trace consisting of 50 measurements (one per volume) spaced every 0.1 s. Traces were averaged over videos, converted to phase ($\overline{\Delta\varphi_{OS}}$) unwrapped if necessary, and finally converted to OPL as given by $$\Delta OPL_{OS} = \overline{\Delta\varphi_{OS}} \frac{\lambda}{4\pi}. \tag{10}$$

The present study used the slow dynamics of the cones to classify cone spectral type but with a slight modification to the extraction protocol. Instead of averaging the response over the entire volume, the study computed a separated average over the aperture of each cone. Cones apertures were identified from en face intensity images using a semi-automatic algorithm.

To extract faster dynamics than the 10 Hz volume rate could resolve (but at the expense of classifying cones), the present study averaged the response over each fast B-scan instead of each volume, in this way increasing our temporal resolution from 0.1 Hz to 3 KHz. To capture the fast dynamics that occurred within milliseconds of the flash onset, the study further analyzed only the B-scans in the volume with the flash and the volume that preceded it. Thus Equation (7) was reduced to just these two volumes. 1D traces of the phase response were obtained by ordering all B-scan responses by their B-scan index in the volume. This approach to extract fast dynamics is based on two assumptions: (1) cones remain temporally stable during acquisition of the pre-stimulus volume, i.e., up to 100 ms, and (2) all B-scans contain the same distribution of S, M, and L cones. While the latter might not hold for a single video, it will when many videos are averaged as was done in this study.

In AO-OCT, cone OSs are characterized by a bright reflection at each tip as shown in FIG. 43A. In FIG. 43A the cone cell is stimulated with a visible flash during AO-OCT imaging and the resulting phase and OPL changes are defined mathematically as shown. The phase difference, $\phi_{OS}$, is between the two bright reflections at opposing ends of the cone OS, which are labeled as IS/OS and COST (cone OS tip). The resolution of the apparatus was 2.4×2.4×4.7 μm3 (width×length×depth), sufficient to resolve these reflections in all three dimensions. Most AO-OCT volume images were acquired at 3.7° temporal to the fovea. The three subjects were free of ocular disease; one of the three was a deuteranope. Brief flashes of visible light (2-10 ms) of different intensities and spectra (see FIG. 43B) were delivered to the retina during image acquisition. Fast and slow dynamics of the cones' phase response were subsequently extracted from the images (FIG. 43A) using B-scan (0.33 ms) and volume (0.1 s) sampling, respectively. The phase responses of cones were first characterized under different illuminant intensities and spectra, then the relationship between these phase changes and the three cone spectral types was established, and finally this relationship was used to classify and map cones in our three subjects.

Results and Discussion

Exp 1—Characterizing the Phase Response of Cones to Light Stimulation: Temporal Properties and Energy Dependence.

Figures 44A, 44B, 44C, 44D:
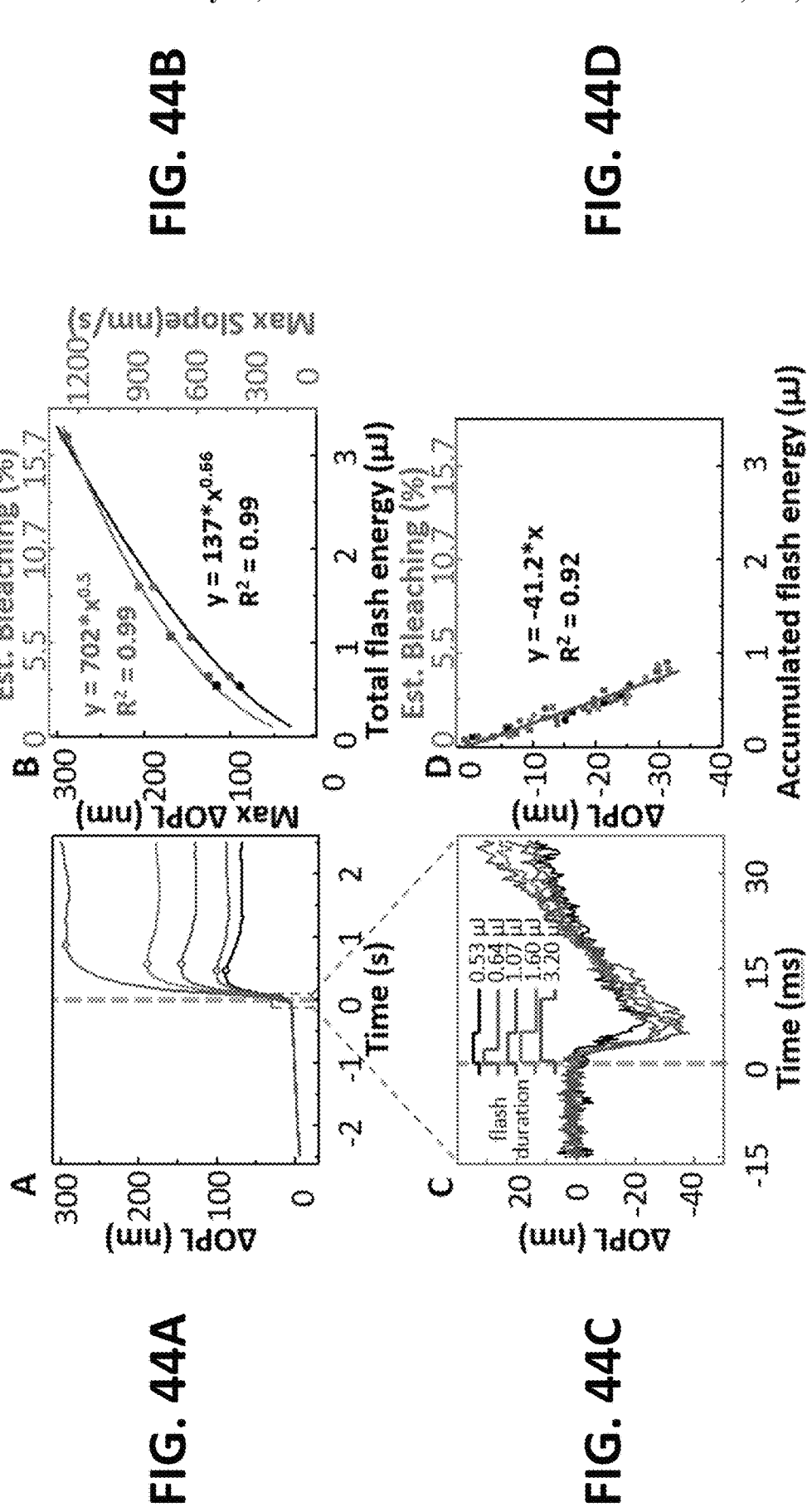
FIG. 44A is a graph showing the average responses of 1,094 cone cells sampled at the 10 Hz volume rate for flash energies over a six-fold range and averaged over 10 videos to improve signal-to-noise, wherein phase response was referenced to the average of the pre-stimulus volumes.
FIG. 44B is a graph showing the maximum $\Delta$OPL and maximum slope of $\Delta$OPL in FIG. 44A plotted against the total flash energy and the predicted percent of photopigment bleaching (top secondary axis), wherein solid curves represent best power fits.
FIG. 44C is a graph of the average fast response of cone cells as analyzed on a per B-scan basis over the single volume during which flash stimulation occurred, wherein the standard deviation of the pre-stimulus signal was measured at 2.4 nm, which corresponds to the noise floor.
FIG. 44D is a graph of $\Delta$OPL during the downward portion of the traces in FIG. 44C plotted against accumulated flash energy and corresponding predicted percent of photopigment bleaching, wherein the solid line represents best linear fit.
Figures 45A, 45B, 45C, 45D:
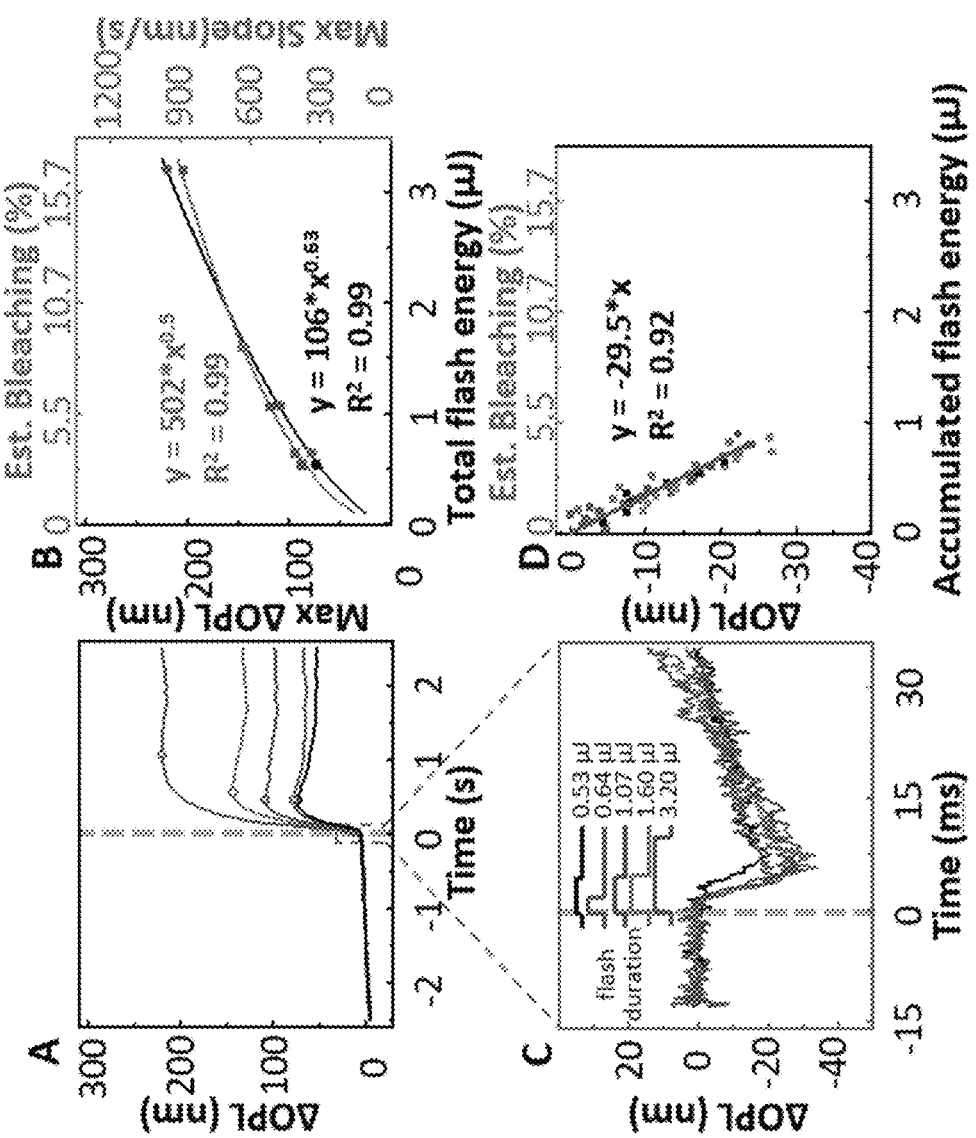
FIG. 45A is a graph showing the average responses of 1,224 cone cells sampled at the 10 Hz volume rate for flash energies over a six-fold range and averaged over 10 videos to improve signal-to-noise, wherein the phase response was referenced to the average of the pre-stimulus volumes.
FIG. 45B is a graph of the maximum $\Delta$OPL and maximum slope of $\Delta$OPL in FIG. 45A plotted against the total flash energy and the predicted percent of photopigment bleaching (top secondary axis), wherein the solid curves represent best power fits.
FIG. 45C is a graph of the average fast response of cone cells as analyzed on a per B-scan basis over the single volume during which flash stimulation occurred, wherein the standard deviation of the pre-stimulus signal was measured at 2.4 nm, which corresponds to the system noise floor.
FIG. 45D is a graph of ΔOPL during the downward portion of the trace in FIG. 45C plotted against accumulated flash energy level and corresponding predicted percent of photopigment bleaching, wherein the solid line represents best linear fit.

The phase response of cones to brief flashes of 637-nm light over a six-fold energy range were assessed. The experiment first quantified the slow dynamics of the cones' response (0.1 to 2.5 s) by averaging ΔOPL across all cones within each volume (~1,100 cones), yielding the mean cone response at the 10 Hz volume acquisition rate. FIGS. 44A and 45A show the averaged traces for the two normal subjects. Phase response of cones is biphasic with amplitude increasing with flash energy in Subject #1 (FIG. 44A) and Subject #2 (FIG. 45A). The dashed gray lines at 0 s in FIGS. 44A, 45A and 44C, 45C represent the 637 nm stimulus onset. Regardless of flash energy, ΔOPL rapidly increased immediately after stimulation, reached a peak after 0.3-0.5 s, then slightly dipped and plateaued for the remainder of the measurement period. The experiment quantified the energy effects using the height of the plateau (peak value) and rate of the rapid increase (maximum slope) of ΔOPL, which are plotted against energy and estimated bleach level in FIGS. 44B and 45B. These data are well fit by power functions of flash energy (E): E0.66 [peak] and E0.5 [max slope] (FIG. 44B) and E0.63 [peak] and E0.5 [max slope] (FIG. 45B). These plots illustrate two important points: First, the asymptotic behavior of ΔOPL (peak and plateau) is strongly energy dependent and consistent with at least one earlier report. This association is taken advantage of in the present cone-classification method as most of the power for differentiating responses to different lights is contained in the peak and plateau. Second, contrary to the same earlier report, the experiment found that the rate of rapid increase of ΔOPL is also energy dependent, indicating that increased stimulus accelerates the underlying physiology.

To assess the fast dynamics of ΔOPL that occurred within milliseconds of flash onset, the experiment examined individual B-scans from the volume containing the light flash. This yielded a sampling interval of 0.33 ms instead of the 100 ms volume-sampling interval, trading signal-to-noise ratio for a 300-fold increase in temporal resolution. Results are shown in FIGS. 44C and 45C for the two subjects. At this scale and resolution, an initial rapid decrease in ΔOPL was followed by a gradual larger increase corresponding to the start of the slow dynamics observed in FIGS. 44A and 45A. To characterize the fast dynamics prior to onset of the slow dynamics (which begin near the response minimum), FIGS. 44D and 45D plot only the downward portion of the response versus accumulated flash energy. The accumulated flash energy is the portion of the total flash energy that illuminates the retina prior to the AO-OCT measurement. Both downward portions exhibit a linear relation with 7.7 nm (Subject #1) and 5.5 nm (Subject #2) decreases in ΔOPL per 1% bleach. Key specifies energy level at eye and flash duration of stimulation. Note in FIG. 44D that the 0.64 μJ, 1.60 μJ, and 3.20 μJ flashes were of the same 320 μW intensity; the 0.53 μJ and 1.07 μJ flashes were 107 μW and 213 μW, respectively.

Collectively, the AO-OCT results reveal two distinct dynamics in the cone ΔOPL caused by brief flashes of light: (1) an initial decrease that is brief, small, and varies linearly with bleach level is followed by (2) an increase that is much longer and larger and varies nonlinearly with bleach level.

Only a few studies report fast dynamics in the cone phase response to flash stimuli in the living human eye. Using AO flood imaging systems, Jonnal et al. and Bedggood et al. inferred physiological dynamics of cones as early as a few milliseconds after flash onset, though neither were able to discern the direction and magnitude of the change as the present disclosure has. More recently, Hillman et al. used full field SS-OCT to measure a similar biphasic response with initial reduction in ΔOPL. However, they did not analyze the fast dynamics, likely because their relatively coarse measurement sampling (6 ms) and long flash duration (50 ms) would have masked the fast dynamic properties.

The time scale and linear behavior of the fast response are consistent with the photoactivation of photopigment molecules—the first step of the phototransduction cascade that occurs within ~0.5 ms of photon absorption and is linearly proportional to bleach level. The time of minimum ΔOPL (averaged over our two subjects) never lagged the flash offset by more than 1.2 ms. This maximum lag time falls within the measurement error of the present disclosure (±SD=±0.6 ms), implying that the fast dynamics of the response are confined to the flash interval. This in turn suggests that these fast changes in ΔOPL originate from changes in refractive index and/or physical length that are specifically associated with activation onset, as cone photopigments are believed to remain active for several tens of milliseconds. Other potential causes may exist for the fast response that are influenced by sustained photopigment activation, such as amplification stages involving transducin and phosphodiesterase.

The slow phase of the response is easier to detect but harder to attribute. Maximum $\Delta$OPL occurred 0.3-0.5 s after the flash, a duration longer than activation and deactivation of phototransduction combined. This maximum phase change is therefore probably dominated by indirect effects of transduction. Osmotic swelling of the OS is one possibility; it was hypothesized by Jonnal et al. to explain dynamics on a similar time scale to that of the present disclosure. A model of osmotic swelling was recently used to explain $\Delta$OPL changes in mouse rods exposed to light flashes, albeit over much longer time and larger magnitude scales. The slow dynamics measured in the present experiment appear consistent with those reported by Hillmann et al.; however, they found no effect of flash energy on maximum slope, whereas the present experiment found it to increase with flash energy. This energy dependence and the finding that the maximum increase rate of $\Delta$OPL occurs very early in the slow dynamic process (~20 ms) are both consistent with the energy dependence and temporal scale of transducin and phosphodiesterase activation, so both are possible contributors.

More specifically, in this experiment it was found that for the slow response the maximum rate of its initial increase (maximum slope of $\Delta$OPL) depended strongly on energy level and was well fit by a power function of flash energy: $E^{0.5}$ (see FIGS. 44B and 45B). However, the temporal sampling of this period of rapid $\Delta$OPL increase using volume-average responses was relatively coarse (~5 volume samples over the ~0.5 s increase).

To assess more accurately this portion of the response, the volumes at the level of B-scans were reanalyzed. This yielded a sampling interval of 0.33 ms instead of the 100 ms volume sampling interval, a 300-fold increase in temporal resolution. Although individual B-scans were of course noisier than the volume average, it was found that the relationship between $\Delta$OPL from B-scans and time was fit well by a log function at each flash energy level (see FIG. 57); in turn, the relationship between the maximum slopes of these log functions and flash energy followed a $E^{0.5}$ power law (FIG. 57F for both subjects), the same as for the initial, coarser volume sampling. However, using the fast B-scan method the maximum slope occurred right at the beginning of the logarithmic fit region, only ~20 ms after flash onset (see FIG. 57), indicating that some component of the underlying physiology must be highly active very early in the slow dynamic process.

In FIGS. 57A-F, red curves represent best logarithmic fits of the response immediately after stimulus onset. The dashed gray lines at 0 s in FIGS. 57A-57E represent the 637 nm stimulus onset. FIG. 57F shows maximum slope of $\Delta$OPL in FIGS. 57A-57E plotted against the total flash energy. Also shown are results for Subject #2. Solid curves represent best power fits.

In general, the present results demonstrate a strong association of cone $\Delta$OPL with flash energy, both in the rate of the initial transient and in the sustained response. This implies that the absorption efficiencies of cones influence $\Delta$OPL. It is therefore hypothesized that cones with different absorption efficiencies—arising for example from differences in spectral sensitivity (S, M, and L cones)—would have different $\Delta$OPL responses to the same light.

Exp 2—Phase Response of Cones Reveals Cone Spectral Type.

In this experiment, the hypothesis was tested by measuring the slow dynamics of individual cones in two normal subjects after stimulating with light flashes of three different spectra (see FIG. 43B), thereby manipulating the absorption efficiencies of the three cone types. To classify cones, the experiment grouped the traces into three classes with a k-mean cluster algorithm that made use of all available information in each trace, and subsequently assigned cone groups to spectral classes based on expected spectral sensitivities to each stimulus wavelength. FIGS. 46A-K summarizes the phase responses of cones to the three different stimuli. The left column and associated histograms show the individual responses of the entire cell population, the left-middle column shows the individual responses grouped by color based on the results of the k-mean classification algorithm, and the right-middle column depicts the mean responses within each of the three color groups.

Figures 46A, 46B, 46C:
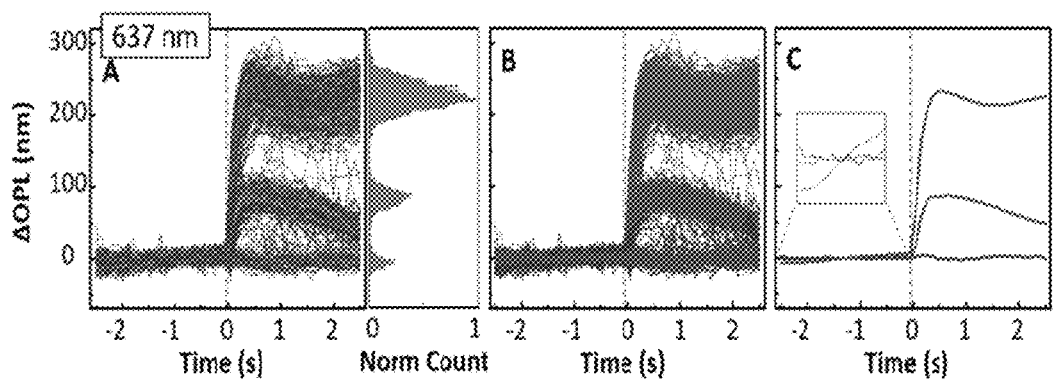
FIGS. 46A-C are response traces for individual cones for stimulation at 637 nm and 1.6 µJ.
Figures 46D, 46E, 46F:
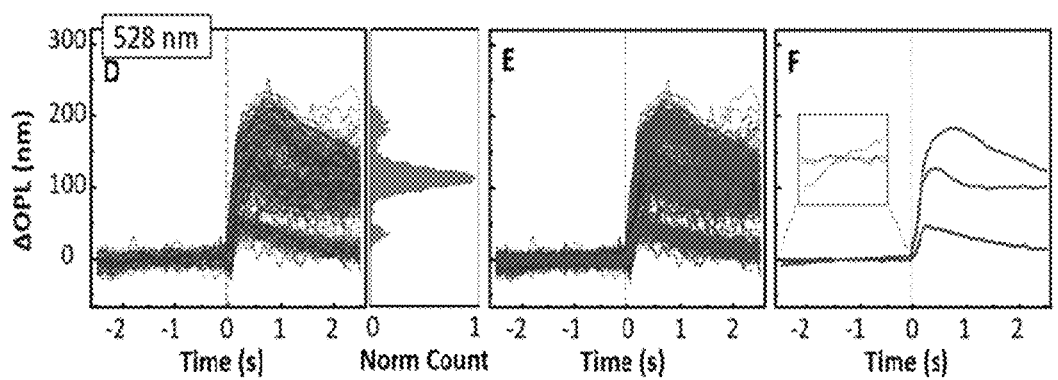
FIGS. 46D-F are response traces for individual cones for stimulation at 528 nm and 0.5 µJ.
Figures 46G, 46H, 46I:
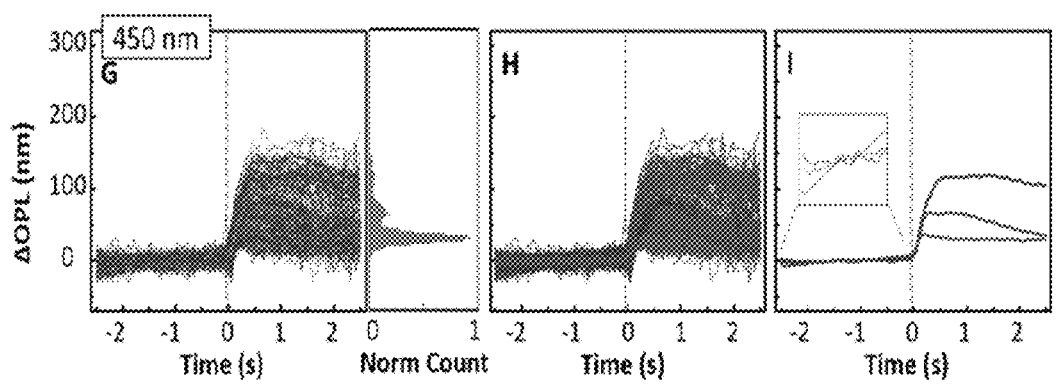
FIGS. 46G-I are response traces for individual cones for stimulation at 450 nm and 1.0 µJ.
Figure 46K:
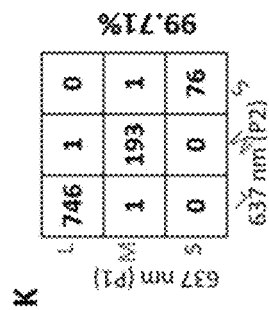
FIG. 46K depicts the repeatability error quantified by comparing classification results of two independent subsets of videos (P1 and P2) obtained with the 637 nm stimulus, wherein each subset contains 7 videos.

Phase response of cones varies with cone type (S, M, and L) and wavelength of the stimulus in Subject #1. The dashed gray line at 0 s represents the 5-ms stimulus flash. Response traces of individual cones are shown for stimulation at 637 nm and 1.6 µJ (FIGS. 46A-C), stimulation at 528 nm and 0.5 µJ (FIGS. 46D-F), and stimulation at 450 nm light and 1.0 µJ (FIGS. 46G-I). Individual traces of 1,094 cone cells are randomly colored. Histogram of normalized cone count is shown for 0.6-1.0 s after flash. Average standard deviation of individual S and M cone traces prior to stimulation was measured at 5 nm, which corresponds to the system noise floor. L cones were excluded from the analysis because their slight sensitivity to the imaging wavelength would have biased the measurement. Phase response was referenced to the average of the pre-stimulus volumes (see FIGS. 46B, 46E and 46H). Cone responses in FIGS. 46A, 46D and 46G are colored red (L), green (M), or blue (S) based on the k-mean classification and expected spectral sensitivity of each cone type to the stimulus wavelength. To quantify the agreement of the present method to classify cones, three confusion matrices were constructed that show the number of cones that were classified as S, M, or L by one stimulus (450 nm, 528 nm, or 637 nm) and as S, M, or L by another stimulus (450 nm, 528 nm, or 637 nm). Percent agreement is shown to the right of each matrix. FIG. 46K shows the repeatability error was quantified by comparing classification results of two independent subsets of videos (P1 and P2) obtained with the 637 nm stimulus. Each subset contains 7 videos.

As evident in FIG. 46A (637 nm stimulus), $\Delta$OPL for the vast majority of cones increased after the flash, reaching a peak ~0.5 s after stimulus onset. Critically, the phase traces appear to form a trimodal distribution. As the spectral sensitivities of the three standard cone types to a 637-nm stimulus obey the ordinal relation L>M>S (see FIG. 43B), the experiment assumed (the hypothesis) that the three response groups of large, intermediate, and small $\Delta$OPL changes correspond to L, M, and S cones, respectively. The experiment therefore assigned the three groups to cone spectral classes accordingly. This classification resulted in the color coded traces (red, green, and blue for L, M, and S cones) shown in FIG. 46B. FIG. 46C is the group average of these three cone classes. The experiment also observed three distinct groups of responses to the 528 nm stimulus (FIG. 46D), albeit less separated. At this wavelength (528 nm), the spectral sensitivity relation of the three cone types obeys M>L>S. The experiment again classified the cone responses into three groups and color coded them accordingly, as shown in FIG. 46E for individual cones and FIG. 46F for group averages. Results from the 450 nm stimulus are shown in FIGS. 46G, H and I. The similar responses of M and L cones to this last stimulus was expected given their close spectral sensitivities at short wavelengths (see FIG. 43B). Nevertheless, some M and L separation is still evident in the figure histogram, and the experiment was able to classify the cone responses into three groups. A distinct advantage of the 450 nm and 528 nm stimuli over 637 nm is that both generate positive responses from all cone types, allowing functional cones to be distinguished from potential non-absorbing or non-functioning ones.

More specifically, it was expected that more complex stimulation involving multiple flashes of different spectra, energies, and/or time durations during the same video will provide even greater separation of the cone responses as was achieved in this experiment. This will improve classification accuracy and may be particularly beneficial in separating more complicated cone responses that one anticipates seeing in aging and diseased retina.

To illustrate how classification can be improved using the data that was already acquired, the averaged cone traces obtained with light flashes of 450 nm, 528 nm, and 637 nm on subject S2 were sequentially combined (see FIGS. 47A-K). Thus, the original 50 measurements per cone per AO-OCT video was increased to a maximum of 150. PCA was then reapplied and their first and second principal components were plotted.

Figures 47A, 47B, 47C:
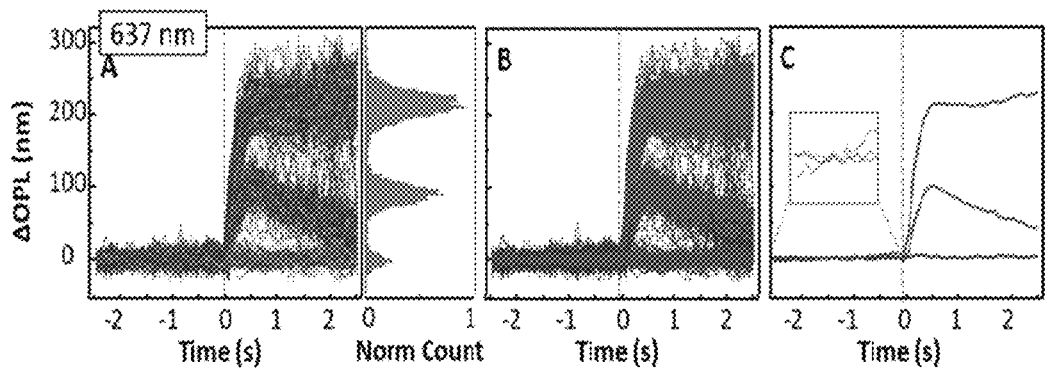
FIGS. 47A-C are response traces for individual cones for stimulation at 637 nm and 1.6 µJ.
Figures 47D, 47E, 47F:
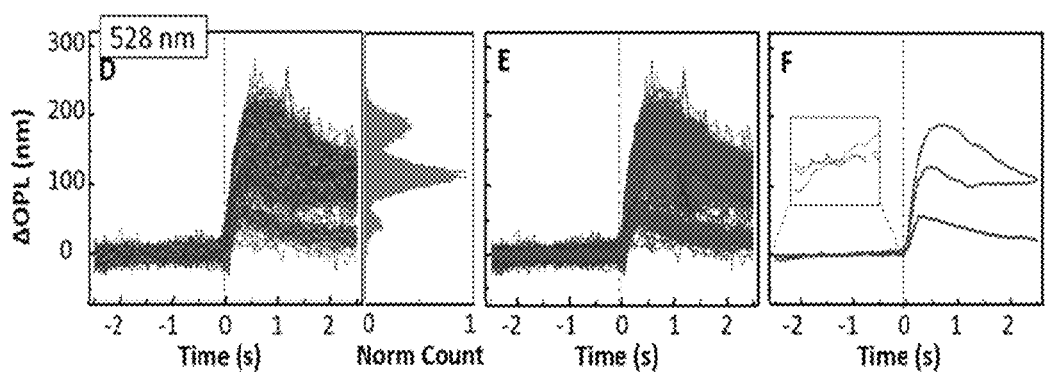
FIGS. 47D-F are response traces for individual cones for stimulation at 528 nm and 0.5 µJ.
Figures 47G, 47H, 47I:
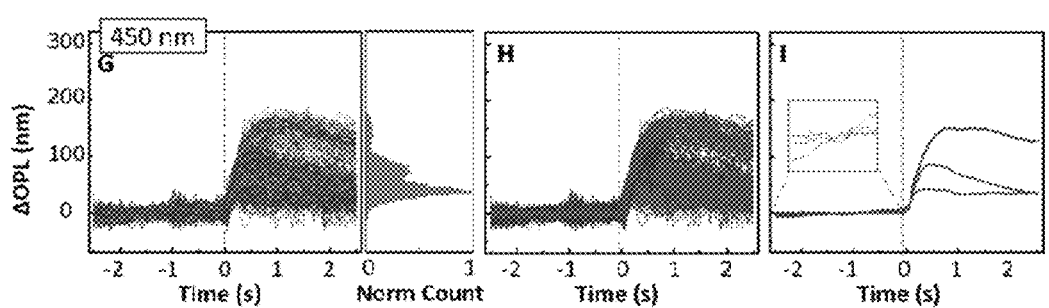
FIGS. 47G-I are response traces for individual cones for stimulation at 450 nm and 1.0 µJ.

The dashed gray line at 0 s represents the 5-ms stimulus flash. Response traces of individual cones are shown for stimulation at 637 nm and 1.6 µJ (FIGS. 47A-C), stimulation at 528 nm and 0.5 µJ (FIGS. 47D-F), and stimulation at 450 nm and 1.0 µJ (FIGS. 47G-I). Individual traces of 1,224 cone cells are randomly colored. Histogram of normalized cone count is shown for 0.6-1.0 s after flash. Average standard deviation of individual S- and M-cone traces prior to stimulation was measured at 5 nm, which corresponds to the system noise floor. L cones were excluded from the analysis because their slight sensitivity to the imaging wavelength would have biased the measurement. Phase response was referenced to the average of the pre-stimulus volumes in FIGS. 47B, 47E and 47H. Cone responses in FIGS. 47A, 47D and 47G are colored red (L), green (M), or blue (S) based on the k-mean classification and expected spectral sensitivity of each cone type to the stimulus wavelength (see FIGS. 47C, 47F and 47I). Average responses of the grouped traces are shown in FIGS. 47B, 47E and 47H. To quantify the agreement of the present method to classify cones, three confusion matrices are shown in FIG. 47J that tabulate the number of cones that were classified as S, M, or L by one stimulus (450 nm, 528 nm, or 637 nm) and as S, M, or L by another stimulus (450 nm, 528 nm, or 637 nm). Percent agreement is shown to the right of each matrix. Finally, FIG. 47K depicts the repeatability error quantified by comparing classification results of two independent subsets of videos (P1 and P2) obtained with the 637 nm stimulus. Each subset contains 7 videos.

Figures 53A, 53B:
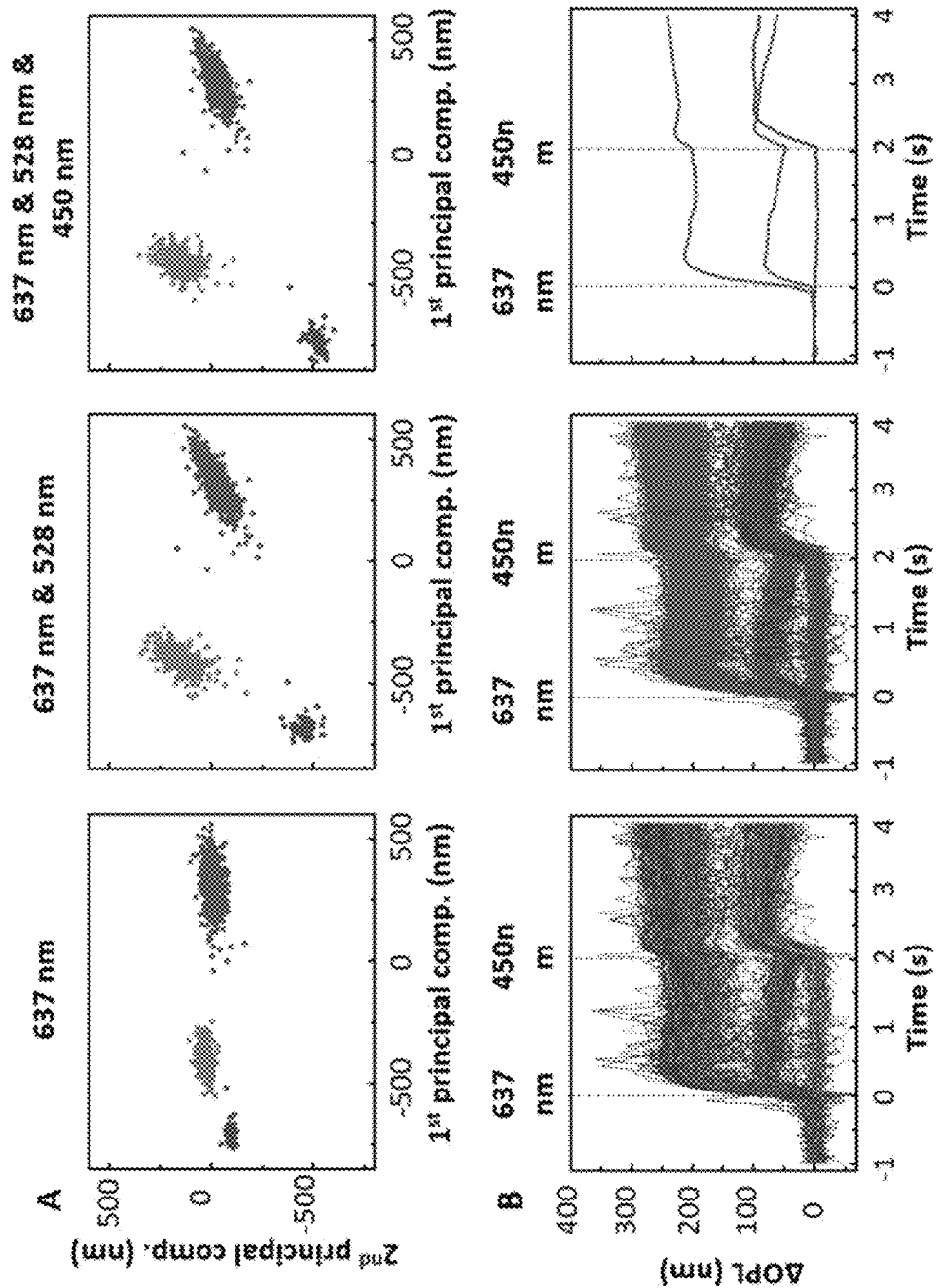
FIG. 53A depicts classification accuracy improvement by leveraging the response of multiple wavelengths of stimuli: 637 nm, 528 nm+637 nm, and 450 nm+528 nm+637 nm.
FIG. 53B depicts phase response of cones variations with cone type (S, M, and L) to a 637 nm-450 nm dual flash sequence in a subject with normal color vision.

FIGS. 53A-B shows the response distribution of 1,052 cones for three combinations of stimulation: (1) 637 nm, (2) 528 nm plus 637 nm, and (3) 450 nm plus 528 nm plus 637 nm. As shown, classification accuracy improves by leveraging the response of multiple wavelengths of stimuli: 637 nm, 528 nm+637 nm, and 450 nm+528 nm+637 nm. Response traces were obtained from FIGS. 47A-K. Cones in the three plots were identified as S, M, and L based on the K-mean classification of cones in the three-wavelength case. Phase response of cones varies with cone type (S, M, and L) to a 637 nm-450 nm dual flash sequence in Subject #1. The dashed gray lines at 0 s and 2 s represent 5-ms stimulus flashes at 637 nm and 450 nm wavelengths, respectively. Individual response traces of 1,049 cone cells are randomly colored. Phase response was referenced to the average of the pre-stimulus volumes. Cone responses in (left) are colored red (L), green (M), or blue (S) based on the k-mean classification and expected spectral sensitivity of each cone type to the two stimulus wavelengths (right). Average responses of the grouped traces in (middle).

The first two principal components captured 97%, 96%, and 93% of the variance, respectively. To facilitate comparison, all cones in the three plots were classified according to the three-stimuli case, which is expected to provide the most accurate classification. As evident in the figure, the addition of the second stimulus (528 nm) increased the separation of the three cone clusters along the $2^{nd}$ principal component axis, in particular the separation between the S and M clusters. The addition of the third stimulus (450 nm) provided further incremental separation that again is most evident between the S and M clusters. For this example, classification applied to the one-, two-, and three-stimuli cases yielded identical classification. The only exception was one S cone that was misidentified as an M cone for the 637 nm stimulus case.

An additional benefit of combining different spectral stimuli is to test for the functional response of all cone types. This can avoid ambiguity between S, M, and L cones and possible non-absorbing or non-responding cones, and can be done efficiently by sequentially flashing the different spectra in the same video acquisition. To illustrate, FIG. 53B shows the response of cones to a 637 nm flash followed 2 s later by a 450 nm flash. As evident in the traces, L and M cones responded to both 637 nm and 450 nm flashes, S-cones responded to only the 450 nm flash, and no non-responding or non-absorbing cones were detected.

Figure 46J:
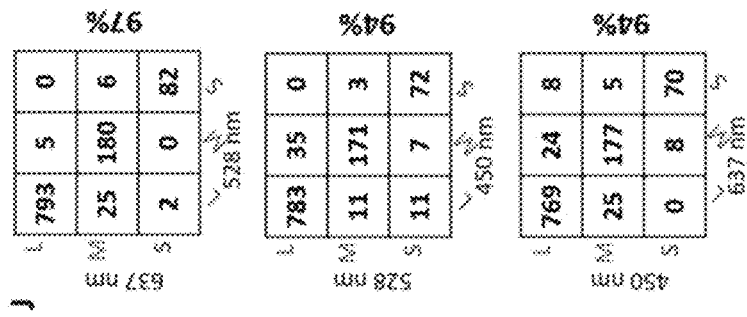
FIG. 46J depicts the percent agreement of each matrix to the left of FIG. 46J.

To further test the hypothesis that the three response groups of cones correspond to the three spectral types of cones, the experiment performed a cross-comparison analysis of the classification results of FIGS. 46A-K. FIG. 46J summarizes the comparison using confusion matrices and shows that individual cones were consistently classified as S, M, or L cones regardless of stimulus wavelength. Agreement between stimuli at 637 nm and 528 nm, 637 nm and 450 nm, and 528 nm and 450 nm are 97%, 94% and 94%, respectively. The small fraction of cones that were classified differently when stimulated with different wavelengths (i.e., non-diagonal components of the agreement matrices) were typically those cones that had lower signal-to-noise ratios in the AO-OCT images. Similar results were obtained from the other normal subject (see FIG. 47J). In general, the strong agreement in classification between the different stimuli supports our hypothesis and demonstrates that the results are highly repeatable even when different spectral stimuli are used.

The experiment also observed a distinct change in OPL before the stimulus (see FIGS. 46C, F and I and FIGS. 47C, F and I). The ΔOPL baseline traces of L cones show a slow (~5.9 nm/s) but significant increase. This is likely due to excitation by the 790 nm AO-OCT imaging source since L cones are more sensitive at 790 nm than M and S cones. While unintended, the classification likely benefited from this increase as it further distinguished L cones from the other two types. A similar benefit also occurs with flashes of higher energy.

This trend is shown in FIGS. 48A-E. While Experiment 2 demonstrated the influence of stimulus wavelength on classification error, the stimulus energy could also be a key influencing factor. To investigate, cones were classified using the Experiment 1 data that was acquired of the same cone photoreceptors, but at five different energy levels of the 637 nm stimulus (0.53, 0.64, 1.07, 1.6, and 3.2 µJ). The resulting ΔOPL cone traces are shown in FIGS. 48A-E.

Figures 48A, 48B, 48C, 48D, 48E:
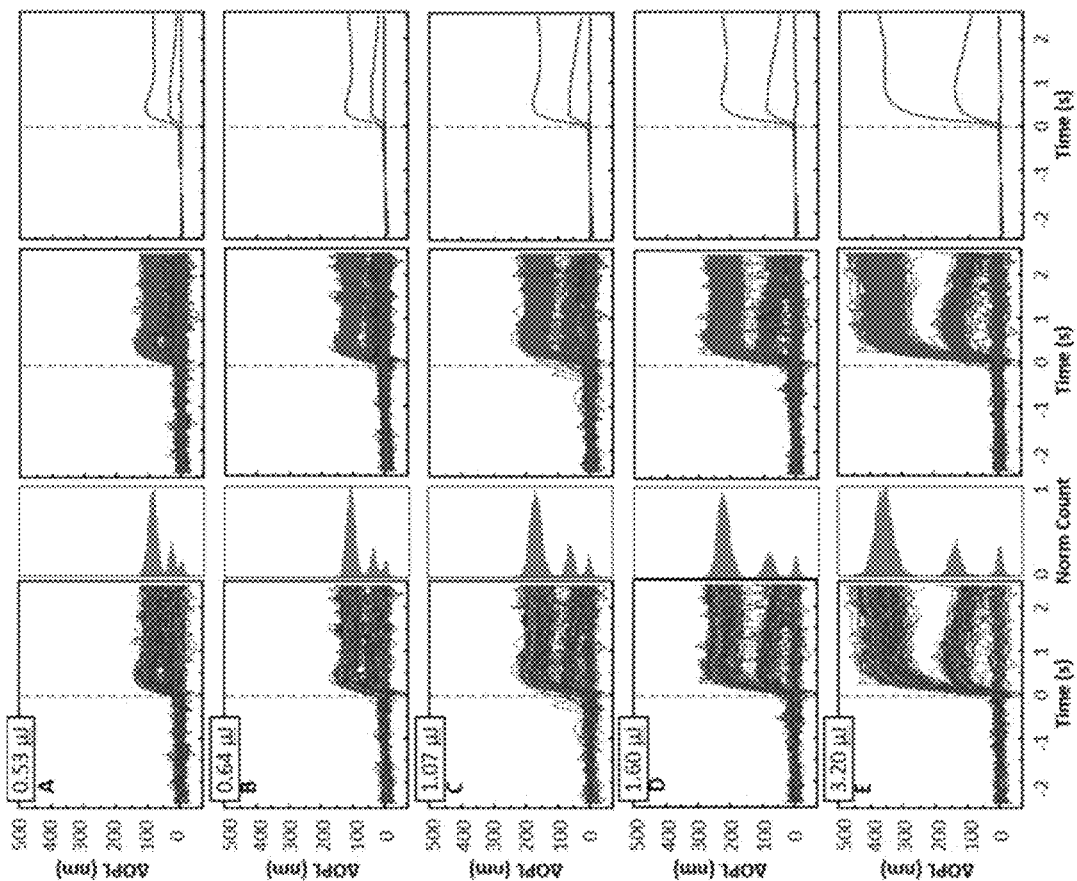
FIGS. 48A-E are response traces of individual cones for stimulus energy level of 0.53 µJ, 0.64 µJ, 1.07 µJ, 1.60 µJ, and 3.20 µJ, respectively, all at a wavelength of 637 nm.
Figure 48G:
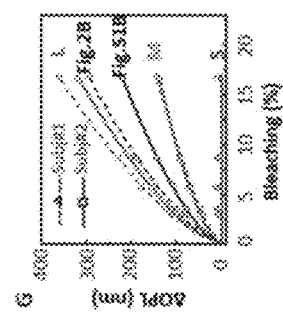
FIG. 48G is a graph of the average phase response of cones weighted by distribution of type (S, M and L)
Figure 48F:
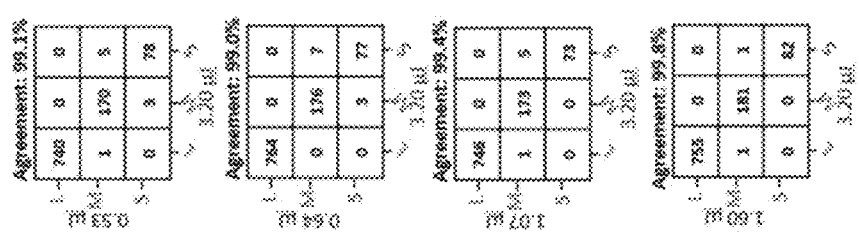
FIG. 48F depicts confusion matrices showing the number of cones that were classified as S, M or L by one stimulus (0.53, 0.64, 1.07, or 1.60 µJ) and as S, M, or L by the maximum energy stimulus (3.20 µJ)

The dashed gray line at 0 s represents the stimulus flash. Individual traces of ~1,000 cone cells are randomly colored. Histogram of normalized cone count is shown for 0.6-1.0 s after flash. Phase response was referenced to the average of the pre-stimulus volumes (second column from left). Cone responses in leftmost column are colored red (L), green (M), or blue (S) based on the k-mean classification and expected spectral sensitivity of each cone type to the stimulus wavelength (third column from left). Average responses of the grouped traces in the second column from left. FIG. 48F includes four confusion matrices showing the number of cones that were classified as S, M, or L by one stimulus (0.53, 0.64, 1.07, or 1.60 µJ) and as S, M, or L by the maximum energy stimulus (3.20 µJ). FIG. 48G provides average phase response of cones weighted by distribution of type (S, M, and L). Black and colored traces of ΔOPL denote the average and type-specific response of cones in Subject #1 and Subject #2. Colored traces for Subject #1 are shown in FIG. 48A-E; colored traces for Subject #2 are from the cone data used in FIGS. 45A-B. Black traces for Subject #1 and Subject #2 are from FIGS. 44B and 45B, respectively.

As evident, separation between the different cone classes increases as a function of the stimulus energy, thus suggesting that higher energy levels improve classification. To quantify this effect, the FIG. 48F confusion matrices show agreement between each stimulus energy level (0.53, 0.64, 1.07, and 1.6 µJ) and the largest (3.2 µJ). The smallest agreement (99.1% and 99.0%) occurs with the two smallest energy levels (0.53 and 0.64 µJ); the largest agreement (99.8%) occurs with the second largest energy level (1.6 µJ). For the latter, only two of 1,020 cones are classified differently, a disagreement of only 0.2% that is likely more attributable to classification with the lower energy level.

Finally, the experiment mapped cone types. The experiment used the 637 nm classification results—which gave the best separation of cone responses—to identify the spectral type of each cone in the en face intensity maps for the two normal subjects (see FIGS. 49A, B, D and E) and to compute the relative proportions of the three cone types. The proportion of S cones was 7.7% for both subjects, which is consistent with the 7% estimated histologically (38) at 3.7° temporal retina. The L:M ratios of the two subjects were 3.8 and 1.7, differing by more than a factor of two but falling within the normal range. It is poorly understood how the proportion of these cone populations varies across the retina. While the present study focused on the classification of cones at a single retinal location near the fovea, the present method can be readily applied elsewhere. The following description demonstrates this application and the notable variation in cone proportions observed across the macula.

Figure 54:
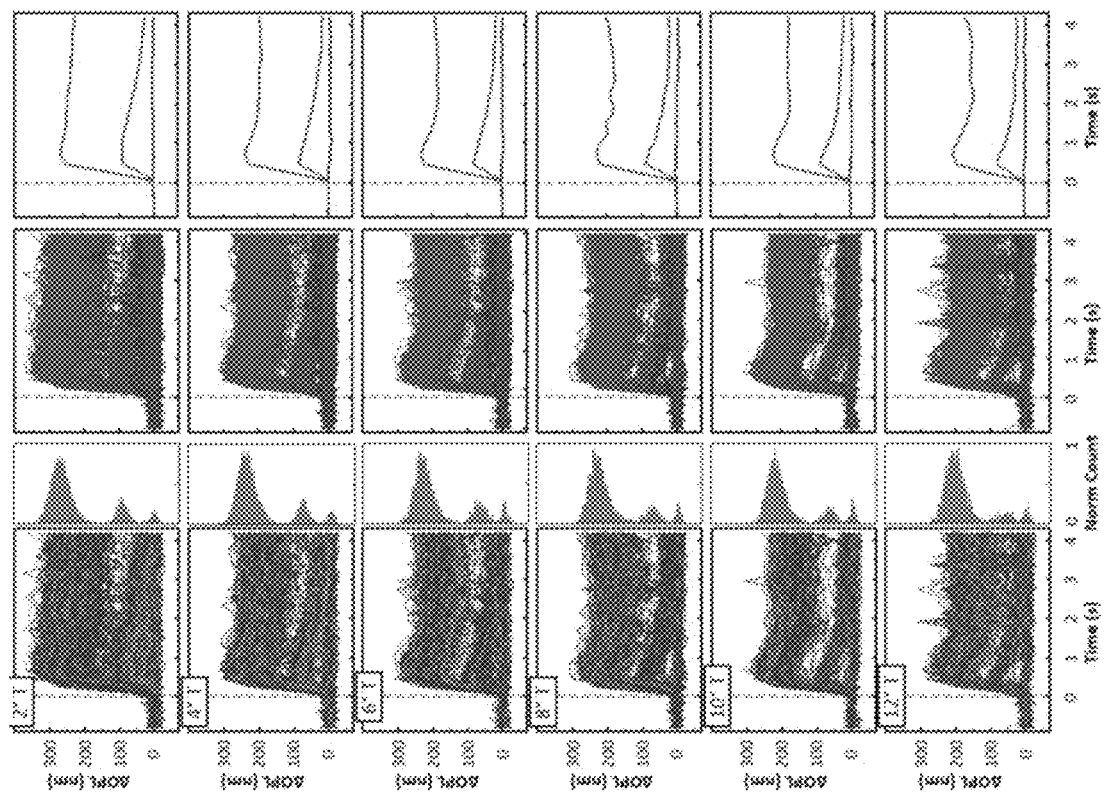
FIG. 54 depicts phase response of cones for a range of retinal eccentricities in a subject.

The present study focused on the classification of cones at a single retinal location so as to facilitate inter-subject comparison. However, the method can be readily applied to other retinal locations. To demonstrate, cones were classified at six different retinal eccentricities (2°-12°) in a single subject using 637 nm light flashes and five 1.3°×1° volume videos per location, which were acquired at 4.7 volumes/s. Stimulus was applied 1 s into the videos. The resulting ΔOPL time series are shown in FIG. 54 and cone mapping and proportion results in FIGS. 55A-H. As shown in FIG. 54, separation of the different cone types is evident at all retinal eccentricities. The dashed gray line at 0 s represents the location of the 637-nm stimulus flash of 1.6 µJ. Retinal eccentricity is separated by row: 2°, 4°, 6°, 8°, 10°, and 12° temporal to the fovea (left column). Individual traces of cone cells are randomly colored. Histogram of normalized cone count is shown for 0.6-1.0 s after flash. Phase response was referenced to the average of the pre-stimulus volumes (middle column). Cone responses in left column are colored red (L), green (M), or blue (S) based on the k-mean classification and expected spectral sensitivity of each cone type to the stimulus wavelength (right column). Average responses of the grouped traces in the middle column.

Interestingly, the averaged groups exhibit remarkably similar responses across eccentricities despite variations in cone morphology that influence their ability to capture and absorb light. For example, cone aperture size increases and photopigment capacity decreases with increasing eccentricity.

Figures 55A, 55B, 55C, 55D, 55E, 55F:
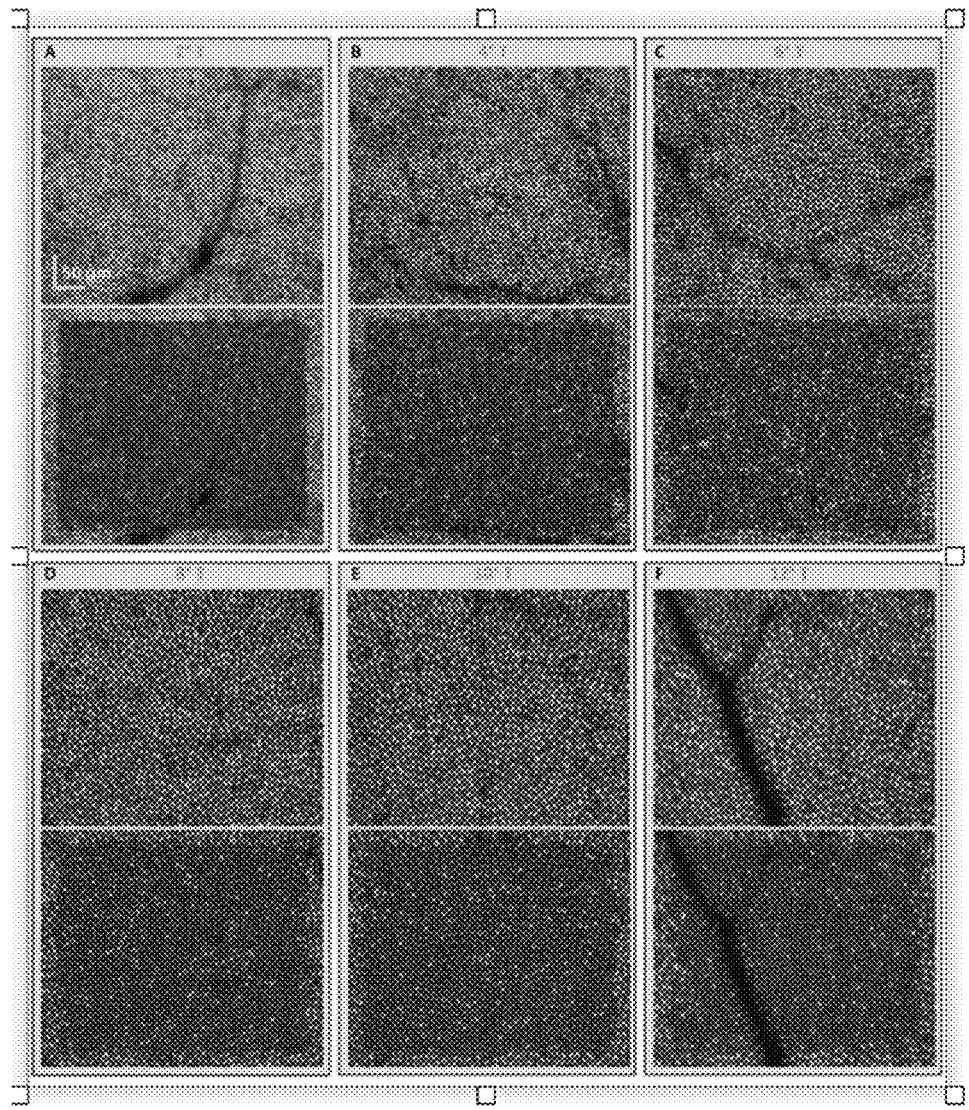
FIGS. 55A-F are mappings of the trichromatic cone mosaic at a range of retinal eccentricities.
Figure 55H:
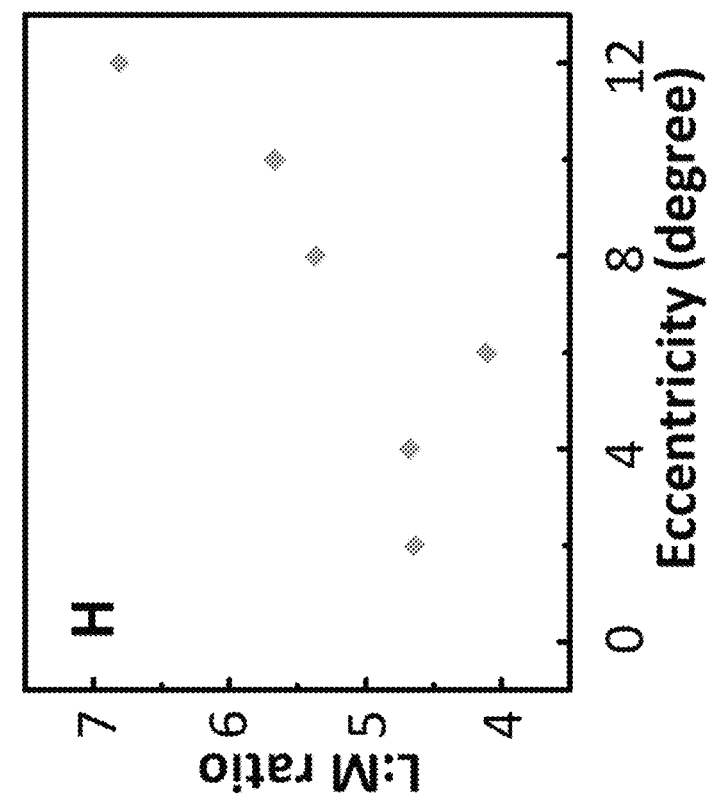
FIG. 55H is a graph of L:M cone ratio.
Figure 55G:
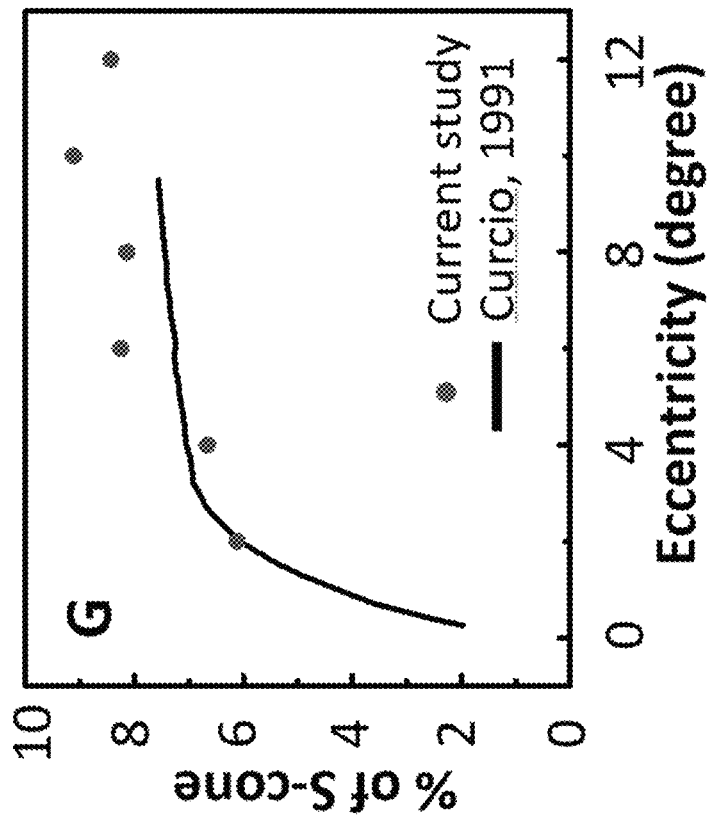
FIG. 55G is a graph of S-cone percentages compared to reported histology for different retinal locations.

Referring now to FIGS. 55A-H, mappings the trichromatic cone mosaic at a range of retinal eccentricities is shown. Six locations were mapped along the temporal horizontal meridian of Subject #1. Intensity images and corresponding trichromatic mapping are shown together for comparison. Cones were classified using the 637 nm stimulus and color coded using S=blue, M=green, and L=red to depict cone type. Note that some cones near the image edge were inadvertently not stimulated due to vignetting of the light flash in the stimulus channel; cones along the edge were therefore not classified. Also note that the intensity images are axial projections through the cone OS, extending 7 microns above the IS/OS reflection peak to 7 microns below the COST reflection peak. Thus, the mottled appearance apparent between cones at the larger retinal eccentricities is likely attributed to rod OS tips (ROST), as previously described. Presumably ROST could be used (in conjunction with a corresponding IS/OS reflection) to study the phase response of rods to light stimulation. This remains future work. FIG. 55G shows retinal dependencies of percentage of S-cones compared to reported histology and FIG. 55H shows the L:M cone ratio.

FIG. 55G shows that the proportion of S cones increases nearly monotonically with retinal eccentricity from 2° to 12°, while FIG. 55H shows the L:M ratio is relatively stable from 2° to 6° and then increases up to 12°. Over this range, the L:M ratio varied by 70%. Little has been reported on how the proportion of these cone populations change with retinal eccentricity, and no reports are known using in vivo imaging methods. S cones have been histologically mapped by distinguishing S from M and L cones based on morphological differences. The present in vivo measurements agree with this histology (see FIG. 55G). However, similar histology fails to distinguish M and L cones due to their similar morphologies. More complex histological processing based on messenger RNA has been used to infer an L:M ratio in excised human retina and found it to increase with retinal eccentricity. However psychophysical studies of color-normal subjects found either no effect of eccentricity or a non-systematic one on estimated L:M ratio. The increase observed in this single subject is consistent with histology rather than psychophysics.

Current AO retinal densitometry classifies cones in a relatively small ~0.5° diameter area. Classifying cones over a larger retinal area would better capture local inhomogeneities in the spatial properties of the trichromatic mosaic and provide more accurate measurement of the geometric arrangement of each type and their potential clustering. In this study, sizes up to 1.3°×1° were used (see FIGS. 54 and 55A-H), resulting in more than a 5-fold increase in the total number of cones classified. This increase was achieved by trading off AO-OCT volume rate for increased FOV, and even larger gains are expected when this tradeoff is optimized.

Exp 2—Cone Classification Error.

Figures 50A, 50B:
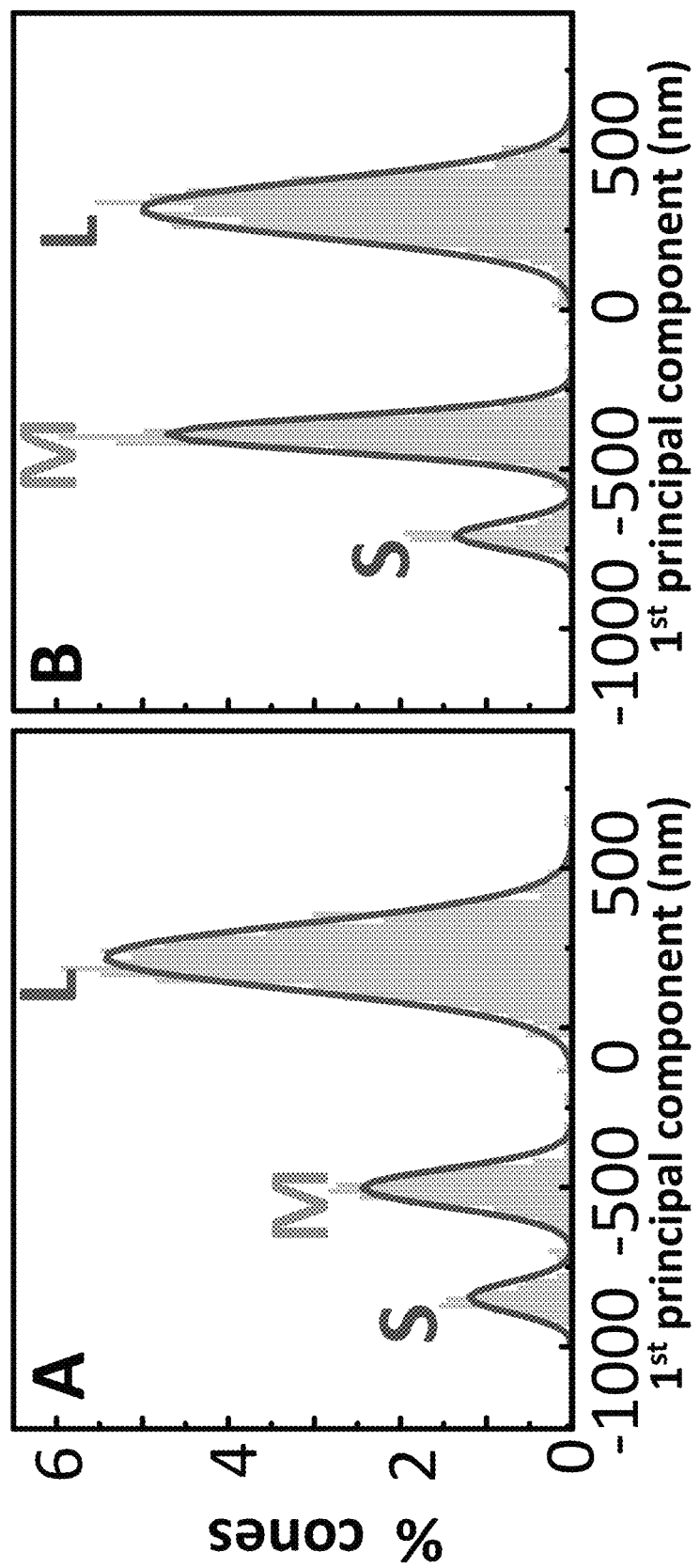
FIGS. 50A-B are graphs of distributions of principal components of ΔOPL traces for the two color-normal subjects as obtained from FIGS. 46A and 47A using the 637 nm stimulus.

Roorda and Williams estimated the uncertainty of their retinal densitometric method by fitting Gaussian models to the two response groups of cones (M and L) that they observed and defining the measurement uncertainty as the area of overlap of the two Gaussians. The present disclosure could not directly apply their method—based on fitting 1D Gaussians to two cone types—to the datasets because all three cone types (S, M, and L) were included and the measurements extended across 50 dimensions (50 measurements per cone per AO-OCT video), all of which were used by the k-mean classification algorithm. The experiment reduced the 50 dimensions using principal component analysis (PCA), and then applied their uncertainty analysis to the first principal component of our 637 nm responses. This analysis overestimates the classification uncertainty of our method relative to theirs because (1) less information was used to analyze than to classify, and (2) S cone assignment error contributed to the present uncertainty. FIGS. 50A-B shows the distribution of the first principal component of the traces in FIG. 46A and FIG. 47A with Gaussian fits for the three clusters included. The overlap between the three Gaussians is <0.02% for both subjects, indicating cone classification uncertainty <0.02% by the criterion of Roorda and Williams. 95% confidence intervals are 0.002-0.100% (Subject #1) and 0.003%-0.076% (Subject #2), which reflect the reliability of the present uncertainty estimates. The present uncertainty (0.02%) is 180-fold better than the 3.6%±1.6% for AO retinal densitometry. This exceedingly small uncertainty supports the contention that the present disclosure provides a highly sensitive method for classifying cones provided the stimulus wavelength (637 nm) effectively separates cone responses.

Figures 56A, 56B:
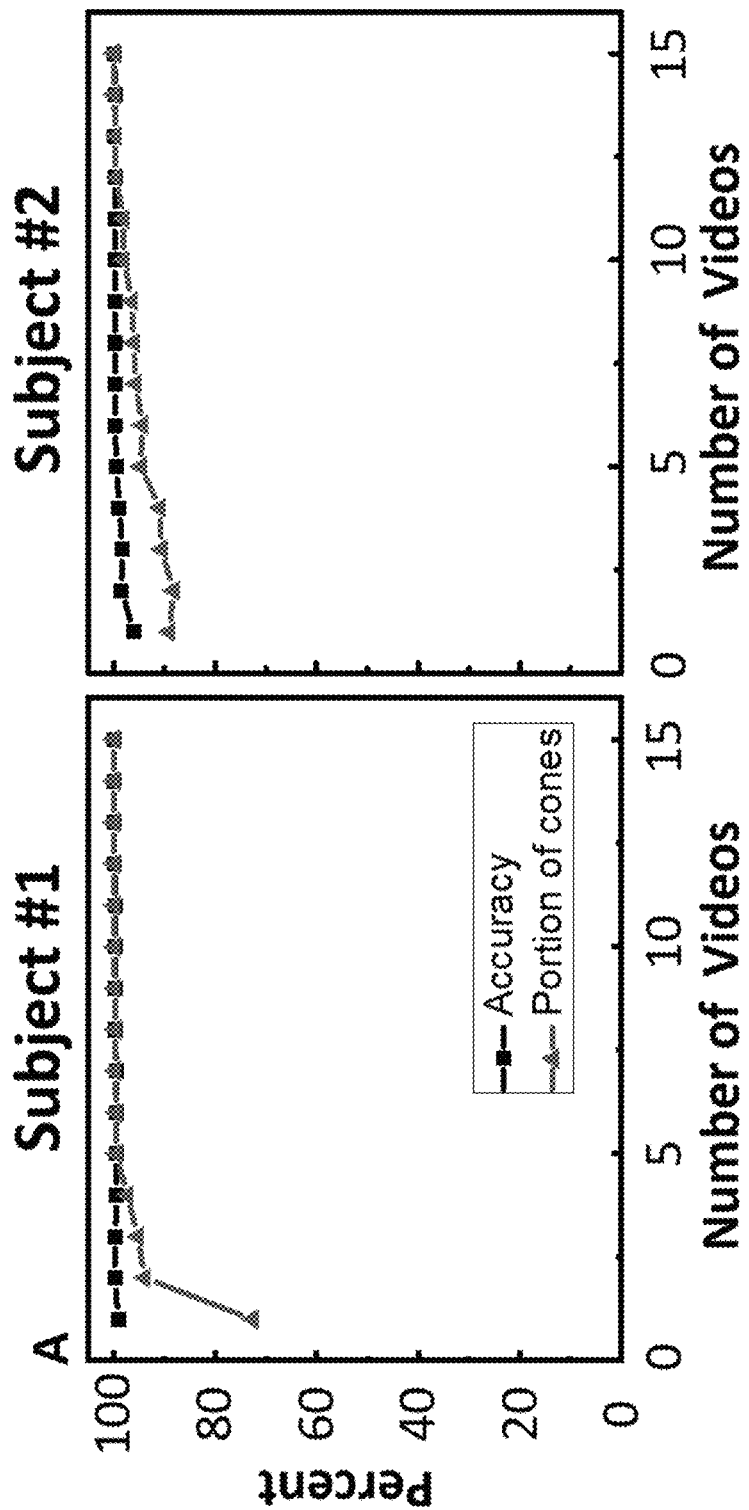
FIG. 56A is a graph depicting classification accuracy and portion of cones for one subject as they relate to the number of videos used, wherein each video consisted of 50 volumes that were acquired in 5 seconds.
FIG. 56B is a graph depicting classification accuracy and portion of cones for another subject as they relate to the number of videos used, wherein each video consisted of 50 volumes that were acquired in 5 seconds.

The error fitting method of Roorda and Williams allowed the present method to compare its performance to others, but a disadvantage is its insensitivity to cone outliers. To better capture this effect, three different repeatability studies were performed to determine repeatability of the present cone classification method. For the first, the present study divided the 15 videos acquired with the 637 nm stimulus in Experiment 2 into two sets (7 videos each), classified cones independently with the two video sets, and compared the results. As shown in the 637 vs 637 nm confusion matrices of FIGS. 46K and 49K, the repeatability errors are 0.29% and 0.37%, respectively. Of course, smaller errors would be expected if all 15 videos had been used. For the second, the present study classified cones in Experiment 1 using the two largest energy levels of the stimulus (10 videos each). As shown in the 1.60 vs 3.20 µJ confusion matrix of FIG. 48F, the repeatability error is 0.2%. For the third, the analysis discussed below shows the repeatability error to classify cones decreases with the number of 5-s videos acquired. For example, FIGS. 56A-B shows errors of 2.5% (1 video), 0.36% (7 videos), and 0.27% (10 videos) when averaged over both subjects. The 0.27% and 0.36% are consistent with the other repeatability results (0.2%, 0.29%, and 0.37%) using the same number of videos, 7 and 10. This error is an order of magnitude larger than the uncertainty error from Gaussian fitting (0.02%), indicating cone outliers are likely present in the data though the number must be exceedingly small as only 1 out of every 270-500 cones was identified differently.

The present AO-OCT method typically used 15 5-second videos to classify the cones of a given patch of retina. The videos were acquired in about 30 minutes, including the delay between videos to allow the cone photopigment to regenerate. Because a shorter acquisition time is often more practical, this study was interested in examining empirically the tradeoff between classification performance and the number of videos acquired. FIGS. 56A-B shows the results, summarizing performance as a function of the number of 5-second videos used. Performance was quantified in terms of classification precision and percentage of cones classified relative to the classification results using all videos, i.e., 15. As shown, high precision (96% to 99%) can be obtained with just one video (5 seconds acquisition time).

Unlike precision, percentage of cones classified is sensitive to eye motion during video acquisition as motion can prevent some cones in the patch from being properly imaged. It was found in two color-normal subjects that 2 to 3 videos were required to classify >90% of cones in the patch compared to what was classified using all 15 videos. Of course, for each subject, the amount of eye movement will determine the number of videos needed to achieve the same percentage. It should be noted that some color vision metrics, such as S:M:L ratio, are unaffected by randomly missed cones and thus for these metrics classification accuracy sets the number of videos required, not percentage of cones classified.

The average cone response of the two normal subjects (see FIGS. 44B and 45B) demonstrates that $\Delta$OPL correlates with the stimulus energy level. The $\Delta$OPL magnitudes of the two subjects, however, are notably different as evident by plotting the FIG. 44B and FIG. 45B curves on the same graph (see FIG. 48G, black curves). Mathematically, one would expect the average cone response to be a linear sum of the three cone type responses weighted by their fraction of the total cone population. To assess which factor (cone type response or population fraction) is responsible for the observed difference in average cone response of our two subjects, the $\Delta$OPL response of each cone type was extracted at each stimulus energy level and for each subject (see FIGS. 48A-E for subject #1) and then plotted them against energy in FIG. 48G. As shown in FIG. 48G, S and M cones in subject #1 responded almost identically to S and M cones in subject #2 (curves of the same color overlap). L cones also responded similarly in the two subjects, though somewhat greater (12.8% larger) in subject #1. This larger L-cone response of subject #1, if applied to subject #2 using a linear relation, would increase subject #2's average cone response by about 11.8%, which represents a significant portion of the 29.3% difference measured in the average cone responses of the two subjects (difference between black curves). Furthermore, subject #1 has a 2.2-fold larger number of L cones compared to subject #2 (L:M ratios of 3.8 and 1.7, respectively). This larger fractional population of L cones, if applied to subject #2 using the linear relation, would increase subject #2's average cone response by about 11.6%, which also represents a significant portion of the 29.3% difference in the average cone responses of the two subjects. It was concluded from this simple analysis that differences in both the cone type responses and cone fractional populations exist and contribute significantly to the differences in the average cone response of the two subjects.

Exp 2-Cone Classification in a Deuteranope.

Figures 51A, 51B, 51C, 51D:
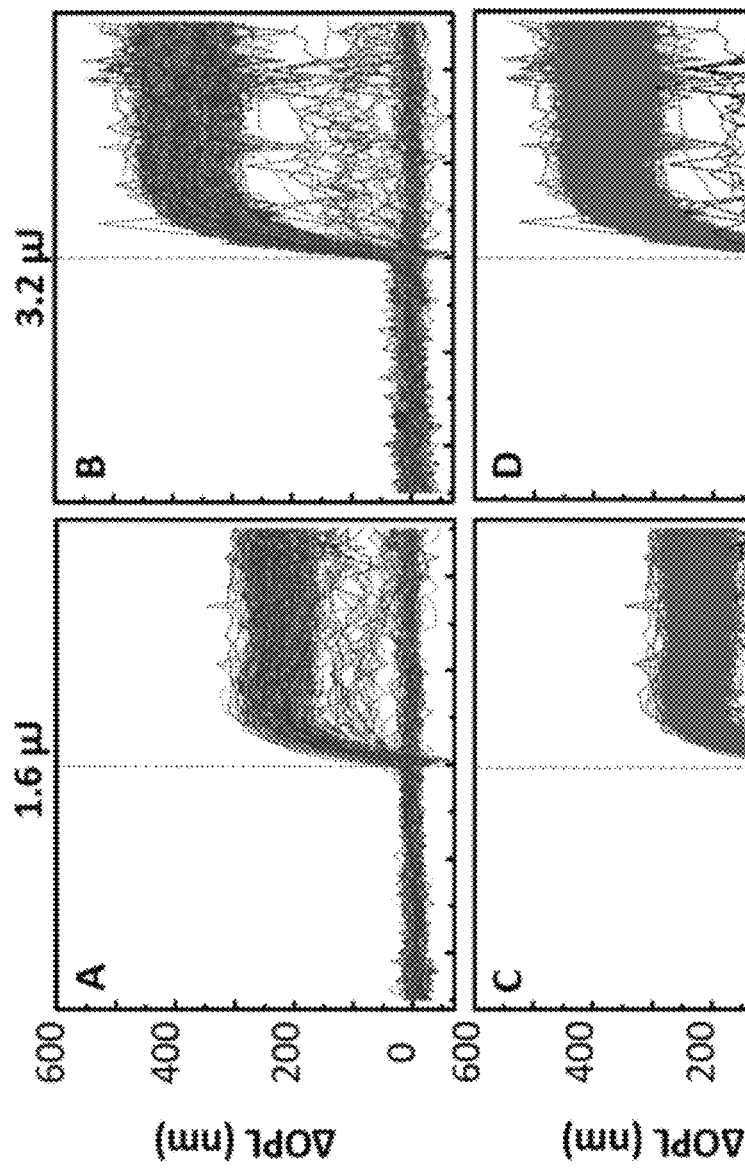
FIGS. 51A-B are response traces of cones in a deuteranope (subject with a specific color vision anomaly in which M cones are missing) for stimulus energy levels of 1.6 µJ and 3.2 µJ, respectively, both at a wavelength of 637 nm.
FIGS. 51C-D are graphs of the phase responses of FIGS. 51A-B, respectively, referenced to the average of the pre-stimulus volumes.
Figure 52J:
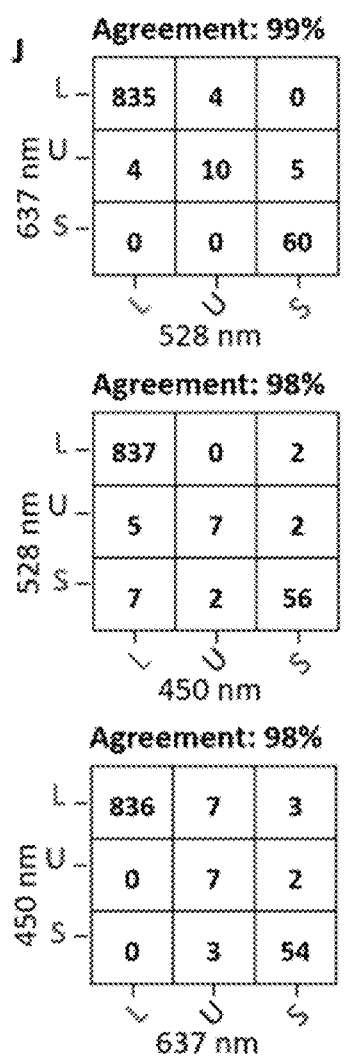
FIG. 52J shows the number of cones that were classified as S, M, or L by one of the three stimuli (450, 528, or 637 nm) to the left of FIG. 52J and as S, M, or L by another of the three stimuli (450, 528, or 637 nm), wherein percentage agreement is shown to the right of each matrix.

To test for classification differences in color blindness, the experiment analyzed the cones of a deuteranope. Signal traces of individual cones for the 637 nm stimuli are shown in FIGS. 51A and 52A and separate mainly into two groups.

Their responses are consistent with those of S and L cones from the two color-normal subjects, and the lack of a third group is expected given the absence of M cones in deuteranopia.

Phase response of cones varies with cone type (S, M, and Unidentified (U)) and stimulus strength in the deuternope. The dashed gray line at 0 s in FIGS. 51A-D represents the location of the 637-nm stimulus flash with (left column) 1.6 µJ and (right column) 3.2 µJ. Response traces of individual cones are randomly colored. Phase response was referenced to the average of the pre-stimulus volumes (see FIGS. 51C-D). Cone responses in FIGS. 51A-B are colored red (L), green (M), or black (U) based on the k-mean classification of traces in FIG. 51A and expected spectral sensitivity of each cone type to the stimulus wavelength. The traces of FIGS. 51A and 51C are average of 15 videos, while those of FIGS. 51B and 51D are average of 6 videos, thus contributing to the larger variance apparent in FIGS. 51B and 51D.

Visualizing in PCA space (the first three principal components), two distinct clusters are indeed present and overlap with those of S and L cones of the two color-normal subjects. However, a third non-distinct cluster (not observed in either of the two normal subjects) is also apparent, being sparsely populated, diffuse, and extending into the other two clusters. Surprisingly, the response of cones in this third cluster increased little compared to the other two clusters when the stimulus energy was doubled as shown in FIGS. 51A-D. Cones in this third cluster also did not respond as expected of S, M, or L cones at 450 nm and 528 nm (see FIGS. 52A-J): in particular, this third cluster responded more strongly than the others at both of these wavelengths. The experiment labeled cones of this third cluster as 'unidentified' (U) because their responses do not resemble those of typical S, M, or L cones as understood. Some of these U cones might be misclassified S or L cones. However, their enhanced responses to short-wavelength light suggest that many of them are of a distinct cone type, albeit undetermined. In terms of proportions, the S cone proportion (6.5%) is lower than that of our two normal subjects, but falls within the normal range. The L cone proportion is large (91.4%), consistent with deuteranopia. Only 2.1% of cones are classified as unknown (U). Note that this proportion falls below the uncertainty of retinal densitometry methods (~3.6%) and would probably not have been detected. While questions remain about these unidentified cones, the preponderance of cones in this patch respond as expected. The experiment found strong agreement (≥98%) between classifications made using the three wavelengths (See FIG. 52J).

The experiment mapped the trichromatic cone mosaic of the deuteranope using the 637 nm classification results of FIGS. 51A-D. FIGS. 49A-F is a mapping of the trichromatic cone mosaic of the three subjects. En face intensity images show the cone mosaics at 3.7° retinal eccentricity as projected through their OSs. Images are shown on a log scale. The dark holes in the mosaic of the deuternope are marked by red arrows and suggestive of missing cone OSs. The holes reflect little light (the 22 marked holes are 35±10 times dimmer than their brightest neighboring cone) and show no evidence of waveguiding (no punctated reflection at hole center). Cone density of the deuternope is 17,587 cones/mm2 and falls in the normal range for this retinal eccentricity (see FIGS. 49D-F). The cone mosaics from FIGS. 49A-C are color coded based on cone classification using the 637 nm stimulus results in FIGS. 46A, 47A and 52A (S=blue, M=green, L=red, and Unidentified=yellow).

L cones clearly dominate the mosaic with a sparse intermingling of S and unidentified cones (see FIG. 49F color map). Unlike the two color normal subjects—whose cone mosaics are essentially contiguous (see FIGS. 49A and B)—the deuteranope's mosaic is distinctly mottled with dark holes indicative of missing cone OSs (red arrows in FIG. 49C). It was noticed that these holes often coincide with a bright punctate reflection near the expected location of the ellipsoid and myoid interface of the cone's inner segment. It was recently discovered the same reflectance oddity in subjects with retinitis pigmentosa and hypothesized that cones with this pattern are undergoing cell death (Lassoued et al., ARVO Abstract #2924407, 2018).

Carroll et al. have reported an interesting correlation between genotype and cone phenotype in red-green color blindness with two dichromatic subjects. Their proposed model suggests that the cone mosaic of a dichromat with a single L/M gene should be complete. Genetic analysis of the present deuteranope performed in the Neitz laboratories at the University of Washington detected only L-opsin genes (no M-opsin genes), and sequencing showed no heterozygosity at any of the spectral tuning sites. MassArray analysis confirmed that the subject is a single L gene deuteranope. Thus the present deuteranope does not support the model of Carroll et al. given the observed (sporadic) gaps in his cone mosaic. This disagreement illustrates the power of the present imaging method to elucidate phenotype information pertinent for testing these models.

The present disclosure provides a highly efficient and accurate method for classifying cones in the living human eye by taking advantage of their phase response to light. Cones were classified based on their slow response, but it is expected that their fast response will also carry useful information as it also covaries with stimulus energy and is initiated by photoactivation of photopigment. These responses straddle the phototransduction cascade, thus their combined use should provide even more power for distinguishing cones. This study was also limited to the reflections of the cone OS. Reflections from all major cone components (IS, OS, soma, and axon) can now be observed. Use of these additional reflections opens up the exciting possibility to spatially resolve dynamics across the entire cone cell, enabling a more detailed view of how photoreceptors respond in vivo.

Method Subjects.

Two color-normal subjects aged 22 (subject #2) and 52 (subject #1) and one deuteranope aged 26 (Subject #3) participated in the study. All subjects were male and had best corrected visual acuity of 20/20 or better and a spherical equivalent refraction between 0 and −2.5 diopters. Subjects were free of ocular disease. Eye lengths ranged from 23.27 to 25.40 mm as measured with the IOLMaster (Zeiss), and were used to scale the retinal images from degrees to millimeters. Color vision phenotype of the subjects was assessed using the Rayleigh match (HMC Anomaloskop), the Farnsworth-Munsell D-15, and pseudoisochromatic plates (Ishihara and Hardy-Rand-Rittler). Subjects #1 and #2 met the accepted criteria for normal color vision; Subject #3 met that for deuteranopia.

Experiment Design.

The subject's eye was cyclopleged and dilated with tropicamide 0.5% and aligned to the Indiana AO-OCT system. System focus was placed at the photoreceptor layer to maximize sharpness of the cone mosaic. AO-OCT volumes were acquired in all the subjects at ~3.7° temporal to the fovea and at six additional locations (2°, 4°, 6°, 8°, 10°, and 12° temporal to the fovea) in one of the subjects.

Each AO-OCT video consisted of 25 or 50 volumes (0.8°×1° or 1.3°×1.5° FOV) that were acquired in 5 s (at either 4.7 or 10.2 volumes/s). Halfway through the video acquisition, a 2° FOV brief flash (2-10 ms; 0.53-3.20 µJ) of visible stimulus was applied to the retina being imaged, thus providing 2.5 s baseline and 2.5 s response of each cone in the volume. Three fiber-based LED light sources provided the stimulation with central wavelengths of 450 nm, 527 nm, and 638 nm. Video acquisition with light stimulation was repeated 5, 10, or 15 times for the same retinal patch. Between video acquisitions, the subject remained in darkness to allow cone photopigment to regenerate. The present experiment empirically found 90 s was sufficient to prevent influence from preceding video acquisitions.

Two experiments were conducted. Experiment 1 characterized the cone phase response to 637 nm light flashes of increasing energy 0.53, 0.64, 1.07, 1.60, and 3.20 µJ, which were estimated to bleach 3%, 3.6%, 5.7%, 8.7%, and 16.7% of the L:M cone photopigment, respectively. Ten 0.8°×1° volume videos of the ~3.7° retinal location were acquired at 10.2 volumes/s for each energy level. Experiment 2 characterized the cone phase response to light flashes of three different spectra that were estimated to bleach 1.1% (450 nm), 9.9% (528 nm), and 8.7% (637 nm) of the L:M photopigment (43). Fifteen 0.8°×1° volume videos of the ~3.7° retinal location were acquired at 10.2 volumes/s. Postprocessing of AO-OCT Volumes.

Volumes were reconstructed; dewarped to correct nonlinearities in the fast-axis scan pattern; and registered in three dimensions to correct eye motion artifacts using a custom 3D strip-wise registration algorithm. Registration entailed selecting one volume as a reference based on good image quality and minimum eye motion artifact. All volumes collected at the same retinal location were registered to this reference regardless of stimulus protocol. Using a common reference allowed us to compare changes in the same cones under different stimulus conditions. Temporal changes in the OPL of the cone OSs were extracted from the registered AO-OCT volumes using the complex form of the signal.

The connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An ophthalmoscopy method, comprising:
providing an adaptive optics optical coherence tomography (AO-OCT) system;
imaging retinal locations of a living subject using the AO-OCT system;
for each retinal location, acquiring AO-OCT video using the AO-OCT system focused at a retinal depth at which cells are to be imaged;
registering volumes in three dimensions;
averaging registered volumes across time points spaced such that natural motion of soma organelles enhances contrast between somas in retinal cells;
using spatial coordinates of the somas to determine soma stack depth, density and diameter; and
determining cell density measurements.

2. The method of claim 1, wherein the cells to be imaged are ganglion cells in the retinal ganglion cell (RGC) layer.

3. The method of claim 1, wherein the retinal locations included locations across a posterior pole of a human eye.

4. The method of claim 1, wherein using spatial coordinates of the somas includes determining at least one of soma size, density, reflectance and cell type.

5. An ophthalmoscopy method, comprising:
segmenting contributions of RPE cells from rod outer segment tips;
averaging a registered RPE signal across time points spaced such that natural motion of cell organelles enhances cell contrast; and
characterizing a three-dimensional reflectance profile of individual RPE cells.

6. The method of claim 5, wherein characterizing a three-dimensional reflectance profile of individual RPE cells comprises characterizing a contribution of rod outer segment tips, RPE cell packing geometry, and a spatial relation to overlying cone photoreceptors.

7. An ophthalmoscopy system, comprising:
an optical coherence tomography camera equipped with adaptive optics;
a controller comprising
registration software to correct eye motion to sub-cellular accuracy for stabilizing and tracking of cells in 4D,
a parallel computing module for real-time reconstruction and display of retinal volumes, and
at least one algorithm for visualizing and quantifying cells and cellular structures, including extracting biomarkers that reflect cell morphology and physiology.

8. A method for observing ganglion cells in a living human eye, comprising:
using an adaptive optics optical coherence tomography (AO-OCT) system to image a volume of a retinal patch including a ganglion cell layer (GCL);
using 3D subcellular image registration to correct for eye motion, including digitally dissecting the imaged volume; and
using organelle motility inside GCL somas to increase cell contrast.

9. The method of claim 8, wherein a 3D resolution of the AO-OCT system is at least 2.4×2.4×4.7 µm³ in retinal tissue.

10. The method of claim 8, wherein using organelle motility includes averaging images of the digitally dissected imaged volume to reduce speckle noise of the images.

11. The method of claim 10, wherein averaging images includes averaging images from more than 100 volumes of the retinal patch to increase clarity of the GCL somas.

12. The method of claim 8, wherein the GCL somas are one of stacked on each other, laying beneath a nerve fiber layer (NFL), or aggregated at a foveal rim of a macula.

13. The method of claim 8, wherein the volume covers a 1.5°×1.5° field of view of a retina.

14. The method of claim 8, wherein using 3D subcellular image registration includes obtaining videos of the volume over a time period and generating cross-sectional scans of the volume by sampling the video.

15. A system for observing ganglion cells in a living human eye, comprising:
an adaptive optics optical coherence tomography (AO-OCT) system configured to image a volume of a retinal patch including a ganglion cell layer (GCL); and
an image post-processor configured to provide 3D subcellular image registration to correct for eye motion, including by digitally dissecting the imaged volume;
the image post-processor being further configured to use organelle motility inside GCL somas to increase cell contrast.

16. The system of claim 15, wherein a 3D resolution of the AO-OCT system is at least 2.4×2.4×4.7 µm³ in retinal tissue.

17. The system of claim 15, wherein the image post-processor is configured to average images of the digitally dissected imaged volume to reduce speckle noise of the images.

18. The system of claim 17, wherein the image post-processor averages images from more than 100 volumes of the retinal patch to increase clarity of the GCL somas.

19. The system of claim 15, wherein the GCL somas are one of stacked on each other, laying beneath a nerve fiber layer (NFL), or aggregated at a foveal rim of a macula.

20. The system of claim 15, wherein the volume covers a 1.5°×1.5° field of view of a retina.

21. The system of claim 15, wherein the 3D subcellular image registration includes obtaining videos of the volume over a time period and generating cross-sectional scans of the volume by sampling the video.

22. A method of classifying cone photoreceptors in the living human eye from photostimulation-induced phase dynamics, comprising:
measuring optical path length changes occurring inside cone photoreceptors during photoactivation to identify cone spectral types;
wherein measuring optical path length changes includes measuring optical path length changes in terms of an equivalent phase change by combining adaptive optics (AO) and phase sensitive optical coherence tomography (OCT) to reveal individual cone reflections in 3D.

23. The method of claim 22, further comprising using a single superluminescent diode with a central wavelength of about 790 nm and a bandwidth of about 42 nm for AO-OCT imaging.

24. The method of claim 22, further comprising using three fiber-based LED sources with spectra of 450±8 nm, 528±12 nm, and 637±12 nm, respectively, for stimulating cone photoreceptors.

25. The method of claim 24, further comprising estimating a proportion of photopigment bleached by the stimulation of the cone photoreceptors according to the equation:

$$-\frac{dp}{dt} = \frac{Ip}{Q_e} - \frac{1-p}{t_0}$$

wherein p is the proportion of unbleached photopigment, I is the retinal illuminance, $Q_e$ is a constant that denotes the flash energy required to bleach p from 1 to $e^{-1}$, and $t_0$ is the time constant of pigment regeneration.

26. The method of claim 22, further comprising classifying cone spectral type using slow dynamics of the cone photoreceptors by computing an average response for each cone.

27. The method of claim 22, further comprising classifying cone spectral type using fast dynamics of the cone photoreceptors by computing an average response over individual B-scans from a volume containing light stimulation for each cone.

28. A method for measuring temporal dynamics of cells, comprising:
using an adaptive optics optical coherence tomography (AO-OCT) system operated at a center wavelength of about 790 nm to acquire volume videos at a location temporal to a fovea;
registering the volume videos to a reference volume to reduce motion artifacts;
characterizing fast temporal dynamics using an auto-correlation analysis to determine time constants for at least one of a nerve fiber layer, a ganglion cell layer and an inner plexiform layer; and
characterizing slow temporal dynamics using temporal speckle contrast on pixels of the volume videos, wherein the temporal speckle contrast includes determining a standard deviation of a reflectance amplitude and dividing the standard deviation by a mean of the reflectance amplitude.

* * * * *